US011690516B2

(12) United States Patent
Podoleanu et al.

(10) Patent No.: US 11,690,516 B2
(45) Date of Patent: Jul. 4, 2023

(54) OPTICAL COHERENCE TOMOGRAPHY (OCT) APPARATUS AND OCT METHOD FOR AXIAL TRACKING AND FLATTENING

(71) Applicant: University of Kent, Canterbury (GB)

(72) Inventors: Adrian Podoleanu, Canterbury (GB); Manuel Marques, Herne Bay (GB); Adrian Bradu, Faversham (GB); Adrian Fernandez Uceda, Canterbury (GB)

(73) Assignee: University of Kent, Canterbury (GB)

( * ) Notice: Subject to any disclaimer, the term of this patent is extended or adjusted under 35 U.S.C. 154(b) by 216 days.

(21) Appl. No.: 16/951,442

(22) Filed: Nov. 18, 2020

(65) Prior Publication Data
US 2021/0145285 A1    May 20, 2021

(30) Foreign Application Priority Data

Nov. 19, 2019 (GB) ...................... 1916825

(51) Int. Cl.
| | | |
|---|---|---|
| *A61B 5/00* | (2006.01) | |
| *G01B 9/02091* | (2022.01) | |
| *A61B 5/16* | (2006.01) | |
| *G01B 9/02055* | (2022.01) | |
| *G01B 9/02* | (2022.01) | |

(52) U.S. Cl.
CPC .......... *A61B 5/0066* (2013.01); *A61B 5/0082* (2013.01); *A61B 5/163* (2017.08); *A61B 5/7257* (2013.01); *G01B 9/02077* (2013.01); *G01B 9/02088* (2013.01); *G01B 9/02091* (2013.01)

(58) Field of Classification Search
CPC ..... A61B 5/0066; A61B 5/0082; A61B 5/163; A61B 5/7257; G01B 9/02077; G01B 9/02088; G01B 9/02091
See application file for complete search history.

(56) References Cited

U.S. PATENT DOCUMENTS

| 9,383,187 B2 | 7/2016 | Podoleanu et al. | |
|---|---|---|---|
| 10,760,893 B2 | 9/2020 | Podoleanu et al. | |
| 2008/0074617 A1* | 3/2008 | Podoleanu ......... | G01B 9/02091 351/221 |
| 2008/0170204 A1* | 7/2008 | Podoleanu ......... | G01B 9/02028 356/516 |
| 2012/0013849 A1 | 1/2012 | Podoleanu et al. | |

(Continued)

OTHER PUBLICATIONS

A. Gh. Podoleanu, Optical coherence tomography, Journal of Microscopy, Oct. 18, 2011, 11 pgs.

(Continued)

*Primary Examiner* — Dominic J Bologna
(74) *Attorney, Agent, or Firm* — Dinsmore & Shohl LLP

(57) ABSTRACT

The present specification relates to Master-Slave (MS) interferometry for sensing the axial position of an object subject to optical coherence tomography (OCT) imaging, and to MS-OCT applied to curved and axially moving objects. The methods and apparatuses allow producing OCT signals from selected depths within the object irrespective of its axial position in respect to the imaging system. Images are obtained for curved objects that are flattened along a layer of interest in the object, images that are used to provide OCT angiography images less disturbed by axial movement or lateral scanning.

20 Claims, 29 Drawing Sheets

(56) References Cited

U.S. PATENT DOCUMENTS

2015/0292860 A1* 10/2015 Podoleanu ......... G01B 9/02004
356/451
2017/0138721 A1* 5/2017 Podoleanu ......... G01B 9/02027

OTHER PUBLICATIONS

Adrian Bradu, et al., Recovering distance information in speclial domain interferometry, Scientific Reports, May 10, 2018, 16 pgs.

Sylvian Rivet, et al., Complex master slave interferometry, Optic Express, Feb. 4, 2016, vol. 24, No. 3, 20 pgs.

Marques, M.J., et al., Complex master-slave for long axial range swept-source optical coherence tomography, Kent Academic Repository, OSA Continuum, Dec. 15, 2018, vol. 1. No. 4, 10 pgs.

Capps, Arlie, et al., Correction of eye-motion artifacts in AO-OCT data sets, Proceedings of Spie, Feb. 11, 2011, 8 pgs.

Boy Braaf, Real-time eye motion correction in phase-resolved OCT angiography with tracking SLO, Biomedical Optics Express, Dec. 5, 2012, 15 pgs.

Shuichi Makita, et al., Optical coherence angiography, Optics Express, vol. 14, No. 17, Jun. 16, 2006, 20 pgs.

Michael Pircher, et al., Simultaneous SLO/OCT imaging of the human retina with axial eye motion correction, Optics Express, vol. 15, No. 25, Oct. 2, 2007, 11 pgs.

Michael Pircher, et al., In vivo investigation of human cone photoreceptors with SLO/OCT in combination with 3D motion correction on a cellular level, Optics Express, vol. 18, No. 13, Apr. 7, 2010, 10 pgs.

Tingwei Zhang, et al., Improving visible light OCT of the human retina with rapid spectral shaping and axial tracking, Biomedical Optics Express Research Article, vol. 10, No. 6, Jun. 1, 2019, 14 pgs.

S. Caujolle, et al., Speckle variance OCT for depth resolved assessment of the viability of bovine embryos, Biomedical Optics Express Research Article, vol. 8, No. 11, Nov. 1, 2017, 12 pgs.

Iwona Gorczynska, et al., Comparison of amplitude-decorrelation, specklevariance and phase-variance OCT angiography methods for imaging the human retina and choroid, Biomedical Optics Express, vol. 7, No. 3, Dec. 14, 2015, 32 pgs.

Rivet et al., "Complex master slave interferometry", Opt. Express 24, 2885-2904 (2016), doi: 10.1364/OE.24.002885.

Marques et al. "Complex master-slave for long axial range swept-source optical coherence tomography," OSA Continuum 1, 1251-1259 (2018), https://doi.org/10.1364/OSAC.1.001251.

Uribe-Patarroyo et al., "Robust wavenumber and dispersion calibration for Fourier-domain optical coherence tomography," Opt. Express 26, 9081-9094 (2018), https://doi.org/10.1364/OE.26.009081.

* cited by examiner

OPTICAL COHERENCE TOMOGRAPHY (OCT) APPARATUS AND OCT METHOD FOR AXIAL TRACKING AND FLATTENING

CROSS REFERENCE TO RELATED APPLICATIONS

The present specification claims priority to GB Patent Application No. 1916825.1 filed 19 Nov. 2019 and entitled "Optical Coherence Tomography (OCT) apparatus and OCT method for axial tracking and flattening," the entirety of which is incorporated by reference herein.

FIELD

The present specification relates to Master-Slave (MS) interferometry and optical coherence tomography (OCT) embodiments and methods for non-mechanical correction of axial movements of on object during imaging. The present specification also provides embodiments and methods for the flattening of en-face OCT images along different contours following orientation of internal subsurface layers in the object being imaged. By flattening the OCT images and reducing effects of movements, better interpretation of OCT images is obtained, allowing display of differences between images, that can be used to show temporal variations, such as for movement of fluids (angiography) and of tissue (heart). The methods and apparatuses allow producing OCT signals from selected depths within the object under study, irrespective of its axial position in respect to the imaging system and irrespective of its curvature.

BACKGROUND

Spectral domain (SD)-interferometry and SD-OCT are technologies based on processing the electrical signal proportional to the intensity modulation of the optical spectrum of the interference signal (channeled spectrum) produced between optical signal from an object under investigation and a local optical reference signal. For each channeled spectrum acquired, SD-OCT produces a depth reflectivity profile, called an A-scan. OCT can produce images with different orientations, such as: (i) cross section (B-scan OCT) images of an object, i.e. a two dimensional (2D) image in the plane (lateral coordinate, axial coordinate) and (ii) en-face (C-scan OCT) images of the object, i.e. 2D maps in the plane (horizontal lateral coordinate, vertical lateral coordinate).

SUMMARY

Modern OCT techniques rely on SD methods which can be implemented in two formats, as described in the article "Optical coherence tomography", by A. Podoleanu, published in Journal of Microscopy, 2012 doi: 10.1111/j.1365-2818.2012.03619.x, based on: (i) a spectrometer or (ii) a tunable laser or a swept source.

In prior art, a spectral domain OCT system consists mainly (FIG. 1) in a two arms interferometer, 1, and a decoder, 2, to obtain depth resolved information from an object 3 and deliver a signal 40 as an A-scan (a reflectivity profile in depth). In one arm, the interferometer sends light towards the object 3 and receives light back from the object 3, along an object path. In the other arm, light travels along a reference path. The light from the object path and from the reference path interferes. Due to interference, the optical spectrum 10' at the interferometer output is channeled (modulated) and the density of spectrum modulation depends on the optical path difference (OPD) between the object path length and reference path length. The decoder 2 produces an electrical signal 20 due to the intensity variation of the channeled spectrum (CS) 10'. The electrical signal 20 is also modulated (channeled). For brevity, in continuation we will refer to the signal 20 as the channeled spectrum, although in reality this is the electrical counterpart of the optical channeled spectrum. Usually, the A-scan is obtained by a processor, 6", operating based on a Fourier transform (FT), usually a fast FT (FFT), of the electrical signal 20 produced by the decoder 2. In practice, the signal delivered by decoder 2 is along the time coordinate that is not necessarily in linear correspondence to the wavenumber or optical frequency. Due to the nonlinear dependence of periodicity of modulation versus the wavenumber combined with the dispersion in the interferometer 1, the signal 20 is chirped. As consequence, if a FFT is applied to the signal 20, for a single scattering center along depth, the reflectivity profile exhibits an A-scan peak that is wider than it should be. Therefore, the prior art based on a FFT suffers from nonlinear representation of the optical spectrum along the time coordinate and requires resampling of data before applying the FT operation. In prior art, a FT can only provide reliable results if data is resampled in such a way that it is reorganized in equal frequency slots. This problem is widely recognized in the OCT practice, as documented in the paper: "Recovering distance information in spectral domain interferometry, Sci Rep 8, 15445 (2018) https://doi.org/10.1038/s41598-018-33821-0 by A. Bradu, N. M. Israelsen, M. Maria, M. J. Marques, S. Rivet, T. Feuchter, O. Bang, A. Podoleanu. Different hardware and software methods have been reported to alleviate the problem of spectral data not organized linearly along the wavenumber coordinate.

To eliminate the need of data resampling, Master Slave interferometry and OCT method were proposed that replaces the FT with multiple comparative measurements, as disclosed in the document D1, by A. Podoleanu, A. Bradu, "Method and Apparatus for Processing the Signal in Spectral Domain Interferometry and Method and Apparatus for Spectral Optical Domain Coherence Tomography", U.S. Pat. No. 9,383,187 B2. In addition, the Master/Slave method allows production of multiple depths en-face (C-scan) OCT images simultaneously. As seen in FIG. 2, (and in more detail in FIG. 3) a Master/Slave (MS) apparatus uses a different processor than 6", a processor 6', operating on Master/Slave method, that incorporates several MS-calculators $41(q)$ and a storage, 5', of channeled spectra called masks, obtained for model objects. The MS-calculator $41(q)$, by its operation, compares the shape of the channeled spectrum signal 20 at the output of the decoder 2, with that of a reference stored version $50(q)$ in the storage 5 and therefore they have been referred to in the MS literature as comparators. When the two shapes are similar, a maximum is delivered at the output. The mask $50(q)$, where q is the mask index, is in fact the electrical signal 20, of a channeled spectrum obtained when a model object was used (a mirror, instead of the object 3), placed at an optical path difference (OPD) in the OCT interferometer as explained more below. For an axial resolution of the OCT system δ, OPD/2=depth=qδ. The MS protocol as explained in D1, returns a complex signal $40(q)$, from each depth given by q, out of the defining depth slots qδ (where q=1, 2, Q), a separate signal from each depth. For simplicity, from now on we will refer to indices q as referring to distance or depth or OPD, due to the proportionality relation between q on one hand and depth and OPD on the other hand.

This operation distinguishes the MS method from the FT conventional method that provides all depth points of the A-scan in one FT step, i.e. all amplitudes, from all depths in a single delivery of signal by performing a FT calculation.

A more detailed diagram of the MS-OCT according to prior art is shown in FIG. 3, where the interferometer 1 is made up of a beam-splitter, 12, a reference mirror 13, an interface optics 11 that conveys light towards the object subject to tests or imaging, 3. The interface optics 11 contains two orthogonal lateral (transversal) scanners, a fast, line scanner 110 and a slow frame scanner 111, according to technology known in the art (galvo-scanners, resonant scanners, electrooptic modulators, acousto-optic deflectors). A single mirror can also be used with the function of a fast and slow scanner according to means known in the art. The object path extends from the beamsplitter 12 until the object 3 and the reference path from the beamsplitter 12 till the reference mirror 13.

The decoder block of the channeled spectrum, 2, translates the modulation of the channeled spectrum at the interferometer output into an electrical signal, 20, and uses two blocks, an optical source 21 and a detector device, or in short, a reader 22.

For a spectrometer-based OCT configuration, the source 21 is a broadband source 210 and the reader 22 is a spectrometer, 220. For a swept source OCT configuration, the optical source 21 is a narrow tunable laser 211 and the reader 22 is a fast photodetector, 221. At each spectrum reading by the decoder 2, a trigger signal 23 is sent to the MS-processor 6'. For each such event, the Q masks from storage of masks 5' are used to produce outputs $40(q)$.

The prior art reports on configurations driven by a broadband source with a spectrometer as reader, are usually denominated as spectral domain OCT, while configurations using a swept source and a photodetector are usually denominated as Fourier domain OCT, or swept source OCT. In spectral domain OCT, the spectral reading process is initiated via trigger 23 generated by the camera in the spectrometer 220. In swept source OCT, the trigger 23 is generated by the swept source 211 for each sweeping (laser tuning). There are also reports using the terminology the other way around (spectral or Fourier). In what follows, we will refer to both types of configurations as spectral domain (SD) OCT for brevity.

In opposition to the prior art of FT-OCT in FIG. 1, the prior art MS-OCT method has opened the avenue of a different type of processing, in parallel, where information from all depths is output in parallel, but along different signals (outputs), as shown in detail in FIG. 3.

To obtain all Q points of the A-scan, in FIG. 3, Q MS-calculators $41(q)$ are used, in a compounded comparator block, 4', using Q masks $50(q)$, stored in the storage block, 5'. The MS method allows direct parallel production of Q reflectivity values in depth in the object 3. This means that by using signals from all MS-calculators using masks of indices q=1, 2, . . . Q, en-face OCT images from Q different depths in the object 3 can be produced on the fly, while the beam is laterally scanned. Also, for each lateral (x,y) pixel, addressed by the lateral scanners, 110, 111, spectral scan r, all Q points $40(q)$ of the A-scan, are delivered by the Q MS-calculators $41(q)$.

Typical en-face scans, a 2D en-face C-scan and a 1D reflectivity profile along a transversal coordinate (T-scan) are shown in FIG. 4(a) while a typical 1D reflectivity profile along depth (A-scan) is shown in FIG. 4(b) in line with scanning terminology used in OCT for both FFT and MS processing.

The electrical signal $I_{x,y}$, 20, of the decoder, 2, can be represented as a 1D array, $I_{x,y}=\{I_{x,y}(1), \ldots, I_{x,y}(m), \ldots, I_{x,y}(M)\}$, for m=1 to M, a vector of M components for each lateral pixel (x,y), where each component $I_{x,y}(m)$, $20(m)$, corresponds to a resolved pixel, m, in the spectral domain. The minimum number M of resolvable pixels is determined by the number of pixels in the linear camera used in the spectrometer 220 or by the number of distinguishable linewidths within the tuning bandwidth (where the linewidth is inverse proportional to the instantaneous coherence length of the swept source 211). Given a sweeping time interval, the number of temporal windows within the sweeping time determined by the digitizer should equal or be larger than M. For N distinguishable OPD values, at least M=2N sampling points in the spectrum are needed. For each lateral pixel (x,y), at least one spectral sweep is needed. For a normal raster scanning, let us consider H lateral pixels along the horizontal $(x_1,y_v), (x_2, y_v), \ldots (x_r, y_v), \ldots (x_H, y_v)$ within a T-scan lateral scan at a fixed vertical coordinate, $y_v$. For V lines, a number of R=HV spectral scans are needed, i.e. of either camera readings when using a spectrometer or sweeps when using a swept source. We will refer in what follows to the index r=1, 2 . . . R as the index of spectral scan events. The channeled spectrum 20 delivered by the decoder 2 is for each lateral pixel (x,y), $I_{x,y}$ (1, 2, . . . m . . . M), where index m is along the spectral coordinate (wavenumber or optical frequency). An index r can be associated to each lateral pixel (x,y), $I_{x,y}(m)=I_r(m)$.

A possible implementation of comparators (MS-calculators) $41(q)$ is via correlation in wavenumber=0. As disclosed in the patent document D1 mentioned above, the two signals are multiplied and an average over the wavenumber coordinate is calculated. If the two signals present similar channeled spectrum modulation versus the spectral coordinate (wavenumber), then a maximum is obtained. If the modulations are dissimilar (inasmuch as the signals are considered orthogonal), then vanishingly small signal results. This is similar to what generally is understood by correlation used in recognizing similarities, with the difference here that correlation does not need to be calculated over the whole range of lags, but for a wavenumber lag=0 only. Approximately, the $41(q)$ MS-calculators are like product operators followed by lowpass filters and rectifiers. The compound comparator 4' uses Q MS-calculators $41(q)$ to produce signals $40(q)$, each of an output amplitude $A_{x,y}(q)$, representing a reflectance value from a depth represented by the mask index q in the object 3, for each lateral pixel (x,y) in the two lateral directions across the object 3.

As described in document D1, the MS procedure operates in two stages:

Master stage: an object model is used, such as a mirror or a lens plus a mirror (in case the system is to be used on retina) and Q channeled spectra are acquired and deposited in a storage of masks. The masks are acquired for a set Q, of OPD values in the OCT interferometer. The Q masks can also be calculated from a reduced number of experimental channeled spectra measurements as explained in the document D2, U.S. Pat. No. 10/760,893 by A. Podoleanu, S. Rivet, A. Bradu, M. Maria, "Apparatus and Methond for Processing the Signal in Master Slave Interferometry and Apparatus and Method for Master Slave Optical Coherence Tomography with any Number of Sampled Depths". Only a few experimental spectra are needed, minimum two, to calculate two functions, g and h that are then used to calculate any number of masks, for any OPD values. Function g incorporates the channeled spectrum chirp that comes from reading the spectrometer 220 or due to nonlinear sweeping of the swept source 211. Function h incorporates the chirp of the channeled spectrum due to dispersion in the interferometer. The masks inferred can be presented in complex form, therefore subsequent reports on the method referred to Complex Master Slave, such as in S. Rivet, M. Maria, A. Bradu, T. Feuchter, L. Leick, A. Podoleanu, "Complex master slave interferometry", Opt. Express 24, 2885-2904 (2016), doi: 10.1364/OE.24.002885 and in the paper by M. J. Marques, S. Rivet, A. Bradu, A. Podoleanu, Complex master-slave for long axial range swept-source optical coherence tomography, OSA Continuum 1, 1251-1259 (2018), https://doi.org/10.1364/OSAC.1.001251. For the scope of this disclosure, we will refer to the prior art technology of Master Slave and Complex Master Slave, as to the Master Slave method (MS) and systems.

Slave stage: the object to be investigated replaces the model object and channeled spectra acquired are compared with the set of Q masks in the storage, for each mask, a separate MS-calculator delivers a reflectivity value 40($q$) at the OPD (depth) value for which the respective mask 50($q$) was either calculated or measured. In this way, Q reflectivity values are delivered from Q points in depth. As a MS-calculator is used for each mask, i.e. for each depth, the MS method is ideally suited to generate a T-scan profile or a C-scan image for each mask used, at constant depth. A-scans can also be produced, as shown in FIG. 4(*b*) by using Q masks.

We distinguish two types of OCT applications: (i) Retina imaging, where the object 3 is the tissue investigated, the retina, behind the eye lens 3', of the eye, when rays pivot through the eye pupil to fan over the back of the eye; (ii) For organs and tissue subject to surgery, skin, eye anterior chamber, for industrial applications and objects of art investigation, the object 3 means the sample itself. Also, the model object in D1 used to acquire masks and in D2 used to acquire a few channeled spectra to calculate all masks, is a lens plus a mirror for retina imaging, while for skin, eye anterior chamber and industrial applications, the model object is a mirror only.

In the case of the eye, because the anterior part of the eye moves together with the object 3, sensing axial movement can be performed using reflections from the cornea, 3', to correct for the axial movement of the part imaged of the object, that is the retina 3. In the case of the eye, 3 and 3' are on the same optical axis. The present specification also covers the case where 3' is away from the optical axis along which the optical apparatus acquires images, as further disclosed below and so different from area imaged of the object, 3. In separating tissue vibration or deformation from its bulk axial movement, areas 3 and 3' should be different. When correction should eliminate the effects of both local vibration or deformation together with that of axial bulk movement, 3 and 3' are the same.

In what follows, the notions of OPD and depths in the object under investigation will be used interchangeably. When referring to a mirror, such as that used by the model object, for OCT applied to skin, or to the mirror in the assembly of model object for the eye, where a lens is also used to mimic the eye lens, reference will be made to OPD, as it does not make sense to refer to a depth to a single layer object. However, different points in depth in the object, each correspond to an aggregated OPD length made from the OPD parts measured in air plus the double of the depth value in the object (tissue).

In the prior art of MS-OCT, the MS-processor 6' contains a storage of Q masks and the same number of Q MS-calculators are used. For the scope of the embodiments described herein, during the processing, as explained further below, a fewer number Q of MS-calculators will be used than the number of calculated or stored masks, N. This is required in order to establish a safe margin for the set of Q masks used to cover the object thickness, within the wider axial range covered by the object due to its axial movements, or due to its curvature.

Imaging the eye, heart or other organs during surgery, which are examples of non-stationary objects, is affected by movement. En-face OCT cuts are prone to distortion and fragmentation due to movement of the object. When the surface is curved, extra fragmentation of en-face OCT image takes place and when combined with movement, makes the interpretation of en-face views difficult. As the optical beam coming out of the imaging interferometer 1 is scanned laterally, curvature of the object may be interpreted as surface "moving away", i.e. an effect that may be treated similar to effects due to axial movement.

As the SD-OCT technology is very often used for imaging non-stationary objects, methods and techniques were developed to axially track their position.

In the prior art, to compensate for the axial movement of the object, three solutions have been proposed: (PA) Post-acquisition methods relying on images only, i.e. software based only, (PA-S) post-acquisition methods employing information on axial position from a sensor, where the information from the sensor is applied to the volume of images acquired and (RTT) real time tracking, where signal from a sensor is used in real time to correct for the image acquisition.

An example of PA methods is given in the paper by Arlie G. Capps, Robert J. Zawadzki, Qiang Yang, David W. Arathorn, Curtis R. Vogel, Bernd Hamann, and John S. Werner "Correction of eye-motion artifacts in AO-OCT data sets", Proc. SPIE 7885, Ophthalmic Technologies XXI, 78850D (11 Feb. 2011); doi:10.1117/12.874376, where a software compensation method is proposed. In this approach, the effects of axial displacement are reduced through a correlation between A-scans of two adjacent B-scans. This allows to estimate the axial motion artefacts. Nonetheless, no accurate information of the displacement is calculated, this is an only an estimation, and no compensation between A-scans inside the same B-scan is proposed.

Another example of PA methods is that proposed in the paper by Braaf B, Vienola K V, Sheehy C K, et al. "Real-time eye motion correction in phase-resolved OCT angiography with tracking SLO", Biomed Opt Express, 2013, 4(1):51-65. doi:10.1364/BOE.4.000051. This has proposed a set of algorithms for the correction of the axial displacement in post-processing between different B-scans. While this has the advantage of not needing extra acquisition, it does not correct for axial displacements inside the same B-scan and it depends on considering a uniform layer over which everything relates to, not depicting accurately the topography and only conserving the relationship between layers.

An example of PA-S method is that in the paper by S. Makita, Y. Hong, M. Yamanari, T. Yatagai, and Y. Yasuno, "Optical coherence angiography," Opt. Express 14, 7821-7840 (2006). doi: 10.1364/OE.14.007821], a software approach is proposed where the axial displacement between A-scans is calculated through the Doppler shift in the blood vessels, i.e. post acquisition based on data from such sensor. A correlation-based algorithm is applied for axial correction of B-scans.

Reports on RTT employ two interferometers. A first interferometer is used to image a region of interest within the sample while a second interferometer is used as a sensor to detect the axial position of the object and dynamically alter the reference arm length of the first interferometer to keep the region of interest imaged by the first interferometer spatially locked along the axis. Usually the two interferometers operate at different wavelengths. This technique is efficient but prone to introducing artefacts due to latency of mechanically moving parts in the reference arm of the first interferometer. An example of RTT was presented in paper by M. Pircher, B. Baumann, E. Götzinger, H. Sattmann, and C. Hitzenberger, "Simultaneous SLO/OCT imaging of the human retina with axial eye motion correction," Opt. Express 15, 16922-16932 (2007). doi:10.1364/OE.15.016922. A SD based partial coherence interferometer is focused on the cornea and incorporated with an imaging OCT system to accurately sense the axial displacements of the eye. In this way, axial tracking is achieved as shown schematically in FIG. 5. Two different optical sources, 21a and 21b are used for two interferometers, imaging interferometer (a) and sensing interferometer (b). Both interferometers (a) and (b) share the splitter 12c. Splitter 12a separates the beam from source 21a into two, towards the object 3 via splitter 12c and the reference mirror 13a in the imaging interferometer (a).

Sensing interferometer (b) uses splitter 12b and the reference mirror 13b. Processor 6"a, using FFT, delivers an A-scan of the channeled spectrum signal 20b. Reader 22b delivers channeled spectrum 20b to a FFT processor 6"b, producing an A-scan that mainly contains a single peak along the OPD coordinate, detecting in this way the axial position of the cornea 3. The information on the axial position sensed by sensing interferometer (b) controls a fast translation stage (voice coil) 77 in the interferometer (a), to compensate the OPD in the imaging interferometer (a) in accordance to variation of the axial position of the object sensed by interferometer (b).

While this is one of the most common approaches to correct for the axial motion, it requires that the voice coil translation stage has a resolution in its position at least equal to the axial resolution of the OCT. Moreover, there is an electrical latency between the start of the movement and the actual acquisition process. Additionally, the stage has to have all vibrations compensated. Lastly, the translation stage 77 will always have inertia, which introduces an error in the compensation that exceeds an axial resolution interval, $\delta$.

In the paper by M. Pircher, E. Götzinger, H. Sattmann, R. Leitgeb, and C. Hitzenberger, "In vivo investigation of human cone photoreceptors with SLO/OCT in combination with 3D motion correction on a cellular level," Opt. Express 18, 13935-13944 (2010). doi: 10.1364/OE.18.013935, an improvement over their previous setup is introduced in which the voice coil translation stage for depth tracking, 77 and mirror 13a in FIG. 5 are replaced with a rapid scanning optical delay line. Whilst being one of the fastest and most accurate systems reported, it still relies on mechanical correction, so with latency in its response.

Another example of RTT is presented in the paper by T. Zhang, A. Kho, and V. Srinivasan, "Improving visible light OCT of the human retina with rapid spectral shaping and axial tracking," Biomed. Opt. Express 10, 2918-2931 (2019). doi:10.1364/BOE.10.002918, where a system is proposed based on an additional laser focused on the cornea, tracking the axial displacement, as in Pircher et al (2007) mentioned above, using a linear translation stage for the motion compensation. An algorithm was presented that allows to calculate the cornea position without applying FFT, reducing the latency in the software calculation, improving the compensation. Nonetheless, since it still requires a mechanical translation stage with electrical response delay and inertia, there are still limitations to the accuracy and speed of the compensation.

Therefore, there is a need for faster tracking and correction methods, preferably, non-mechanical for less latency in their correcting feedback.

A problem with the set-ups sensing the cornea axial movement to compensate for the axial displacement of the retina is that pulsatile blood in the retina may displace the retina tissue significantly. Compensating the head, or the whole eye axial bulk movements by using signal from the cornea will not compensate for the pulsatile movement of the retina. In addition, when the eye looks off axis at a large angle, there is an angle between the eye axis and the direction of the optical axis of the imaging system. This means that correcting for an axial displacement of the cornea is not the same as for the axial displacement of the retina. Similarly, when measuring the elastic displacement due to the pulsatile blood in vessels and organs, it is essential to measure and evaluate the bulk axial movement, whose effects need to be reduced, without affecting the axial movement due to the pulsatile blood that represents the useful signal.

Therefore, there is a need to make distinction between the axial movement due to bulk displacements of the eye and that due to the pulsatile blood of the retina. There is also a need to make distinction between the overall movement of an organ such as heart and skin due to patient body movement, and the movement exclusively due to an external factor used to initiate elasticity movements, such as an air puff or due to the pulsatile blood, useful in diagnosis of diseases.

Another class of applications of the present disclosure refers to imaging curved targets. Typically, organs, tissue being investigated present curved, non-planar surfaces. For the scope of the disclosure we will refer to all such samples imaged as objects, where the object can be a piece of a material or part of a tissue, or an organ. Due to surface curvature of the object, the en-face (C-scan) images are in most cases fragmented and include other layers in the same sectioned image. For instance, in imaging the retina in a human or animal eye, it is important to produce an en-face image of a targeted layer, such as the ganglion cell layer or the retinal pigment epithelium layer (RPE). Such layers sit at a defined depth from the top of the retina. A simple C-scan in a conventional OCT system will normally intersect several other layers due to the eye curvature, leading to circle like images instead of planar surfaces, i.e. to fragmented images in transversal section. Similarly, in surgery, the tissue is curved, and en-face cuts do not intersect the same subsurface layer, but several layers, so poor guidance is provided to the surgeon. To present an en-face layer containing similar material or structure, not including parts of other layers in depth, supplementary processing is required, including segmentation followed by flattening of surfaces, that take time, hence all performed as post-processing steps.

A more acute issue is in wide-angle lateral imaging of the eye. Over 40 degrees cross section (B-scan) displays not a rectangular image but a U (V)-shaped structure image instead. Correcting or flattening such displayed image or flattening the en-face image becomes a challenge due to excessive eye curvature. Even more problematic is the need of real time en-face flattening when increasing the rate of spectral scanning from hundreds of kHz to multi-MHz. A calculation of an FFT for an M=1024 sampling points require ~1 microsecond time, if processing is needed for chirp or dispersion, time is longer. It would be desirable for real time en-face flattening or for display of a flattened image with minimum delay to perform correction in the time of spectral scanning. For MHz line rate, this would be 1 microsecond, but there are already faster swept sources reported, hence we would need even sub-microsecond correction to perform correction on the fly.

To diagnose disease and display vasculature, such as in OCT angiography (OCTA), it is essential that not only movement is eliminated but that the en-face cuts are made from the same layer. Therefore, the tissue volume is corrected for curvature and en-face images are sliced in the volume afterwards. This is a time expensive operation. Therefore, there is a need to reduce the time between acquisition and display of flattened en-face OCT slices and provide OCTA images quicker, and possibly, better cleaned in terms of their curvature artefacts and axial movements. A similar problem is encountered in surgery, as tissue is curved and diagnosis requires flattened images from specific depths measured from the top of the tissue. Decision time is important in surgery and therefore there is a need for quick display of flattened en-face OCT images to guide the surgeon during surgery.

The dynamics of correction needs to be faster than the axial movement. Micro-saccades in the eye are in the sub-millisecond range.

Lateral scanning is performed in milliseconds to sub-milliseconds, so again, similar demand for dynamic correction to reduce effects of either axial movement or of tissue "walking off" due to the combined effect of lateral scanning and object curvature. Lateral scanning is also in the milliseconds to sub-milliseconds, i.e. even when the object is stationary, if curved, a real time for flattening operation would need to operate in the sub-millisecond range, not possible to be achieved using correctors based on mechanical means.

Therefore, there is a need to compensate for the cumulated effect of bulk axial movement and axial "walking off" due to lateral scanning of curved objects.

Edge Detection

In the OCT practice, edge detection uses thresholding over peaks obtained within A-scans. In conventional OCT, a FFT of the channeled spectrum delivers the A-scan, that represents a one dimensional reflectivity profile over OPD or depth in the object (organ, tissue, material). Then a segmenting line is superposed over the structural B-scan image and its axial position accuracy depends on the strength of signal in the surrounding pixels. Segmented (edge detected) layers are also necessary in the practice of tracking, where the distances up to the axial position of the tracked layer from a reference point are measured and the instantaneous OPD position of the object is altered for compensation of axial movement in the image.

The imaging system presented in FIG. 1 can be used for edge detection purposes. However, as the signal 20 needs to be prepared for FFT in the processing block 6", errors in resampling and dispersion compensation lead to imperfections in the segmented surfaces. If corrected, these take time as they need to be applied for each spectral scan (triggered by the spectrometer 220 or by the swept source 211, depending on the technology used). It would be desirable to infer the axial position without recurring to a FT.

Therefore, there is a need for more efficient segmentation/edge detection methods.

In prior art MS implementations, the number of MS-calculators matches the number of masks. This restricts the versatility of MS processing, faced with real situations, of OCT imaging of moving objects and of curved objects. Dynamic change of axial position of the object due to movement requires dynamic correction of the axial range targeted around new OPD positions. Similarly, during the lateral scan of a curved object, the axial interval range of significant reflectivity values varies from a lateral pixel to next. To cover such situations, an axial range of expected OPD values needs to be reserved or allocated to exceed the object thickness including extended axial intervals to cover the object extension axially due to its curvature. This leads to non-efficient operation in terms of allocation of digital resources that limits the speed of operation.

Therefore, a more versatile signal processing is needed to dynamically adapt the imaging system to axial movement and object curvature in order to optimize digital resources and reduce the time for signal processing.

In a first aspect, the present specification discloses a Master Slave—OCT system equipped with a MS-processor, according to embodiments, that contains an accessible Mask Selector, that allows rapid, dynamic and fast generation of a single mask or of a few masks, on the fly, to be used in the MS protocol, under a control signal applied to a control input.

In a second aspect, a method for dynamic selection of masks from a storage of masks, making use of a unique method that can enable fast provision of a single mask or of a few masks by using an accessible storage block, to perform MS segmentation is disclosed.

In a third aspect, a method for selection and swap of a selected number of Q masks, with indices in a continuous sequence, making use of fast shifts of such sets of Q masks in a Mask Selector block, whose mask indices are slid along a register of N mask indices with N>Q, to perform fast MS axial tracking is disclosed.

In a fourth aspect, devices and methods for flattening tissue are disclosed. Flattening the image section of an object imaged is made in accordance to the axial position of each lateral pixel in the image measured up to a reference layer in the object along the direction of the optical scanning beam. When the object is the retina, the reference layer can be the inner limiting membrane, a distinct layer at the top of the retina, immediately below the vitreous, or the photoreceptor layer or the RPE or any other layer that can be easily distinguished inside the retina. The flattening is performed by producing T-scans of lateral pixels, where from a lateral pixel to the next, the mask used in the MS-processor according to embodiments, is changed (replaced) in accordance to the axial distance at that transversal location from the reference layer measured along the direction of the scanning beam. To obtain en-face views of a layer containing similar structure, from within the curved retina, the en-face cut needs to follow the retina curvature, i.e. all points in the image for all lateral pixels to be obtained from the same depth measured from the top of the retina. For all pixels in an en-face OCT image to correspond to the same layer in the curved retina, prior art moves the A-scans in respect to each other in the priory acquired OCT volume, to align the structure of interest within a flat layer, which is then displayed en-face (process referred as flattening). In other words, pixels in the en-face image correspond to signal returned from suitably corrected OPD values. If FFT was used, A-scans are produced that extend outside the axial range of interest. Then signal from selected depth intervals along the A-scans are used to assemble the en-face OCT volume. Such procedures may take seconds to minutes, not suitable for quick decisions such as in surgery.

According to the embodiments, using the MS protocol, it is not necessary to calculate A-scans, but operate within restricted axial range intervals, with advantage in terms of signal processing. The present specification puts forward a procedure where the mask used for each lateral pixel is changed from a lateral pixel to next according to the OPD value of that lateral pixel. In this way, fewer calculation operations than prior art are needed to generate a single en-face OCT slice, or a few en-face OCT images.

For edge detection (segmentation of contours and surfaces), two sensor embodiments are disclosed based on MS, that in some circumstances can operate faster and are more efficient than using FFTs. There are also situations where for segmentation only, a FFT is faster, hence in another aspect, the present specification refers to a sensor based on FFT to sense the axial distance to instruct the MS processing in creating a corrected image.

To perform flattening, embodiments perform segmentation and sensing of axial position of each lateral pixel using the same channeled spectrum employed in the imaging.

As another possibility, the present specification discloses a solution where a contour (supplied by the user) is manually drawn over the live B-scan that is converted into a distribution of mask indices that can be used by a corrector for flattening.

In a fifth aspect, devices and systems employing a position sensor of axial position using a separate interferometer, to perform edge detection for axial tracking are disclosed. The position sensor monitors the axial position of a reference part of the object. For instance, when the object is the eye, the reference part can be either cornea or retina or the forehead of the patient. For each transversal pixel, r, the position sensor produces a signal containing the information on the axial distance measured up to the reference part of the object. This information is then employed to control the choice of Q<N masks, where the Q masks selected are used by the Master Slave imaging system to produce reflectivity values of pixels corresponding to the depth positions of the Q masks selected.

In a sixth aspect, devices and methods that combine the axial tracking of the object as well as correction of its curvature to provide a flattened image or volume of the object less affected by the axial movements of the object are disclosed.

In a seventh aspect, devices and methods using two sensors for better inference of axial movements affects over the OCT images are disclosed. A $1^{st}$ sensor uses the electrical signal due to the same channeled spectrum signal as that of the imaging interferometer. A $2^{nd}$ sensor uses a different interferometer. The two interferometers use different optical sources and they may acquire signal from the same part or different parts of the object.

In an eighth aspect, devices and methods to produce in quasi real time en-face images of vasculature are disclosed.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

FIG. 7a' shows the segmentation procedure of the sensor in FIG. 7a using MS.

FIG. 7b shows another version of the MS-processor and sensor in FIG. 7a.

FIG. 7b' shows the segmentation procedure of the sensor in FIG. 7b using MS.

FIG. 7c' shows the segmentation procedure of the sensor in FIG. 7c using FFT.

FIG. 12a' shows the edge detection procedure of the sensor in FIG. 12a using MS.

FIG. 12b shows another version of the sensor and MS-processor in FIG. 12a.

FIG. 12b' shows the edge detection procedure of the sensor in FIG. 12b using MS.

FIG. 12c' shows the axial detection procedure of the sensor in FIG. 12c using FFT.

DETAILED DESCRIPTION OF THE PREFERRED EMBODIMENTS

Figure 1:
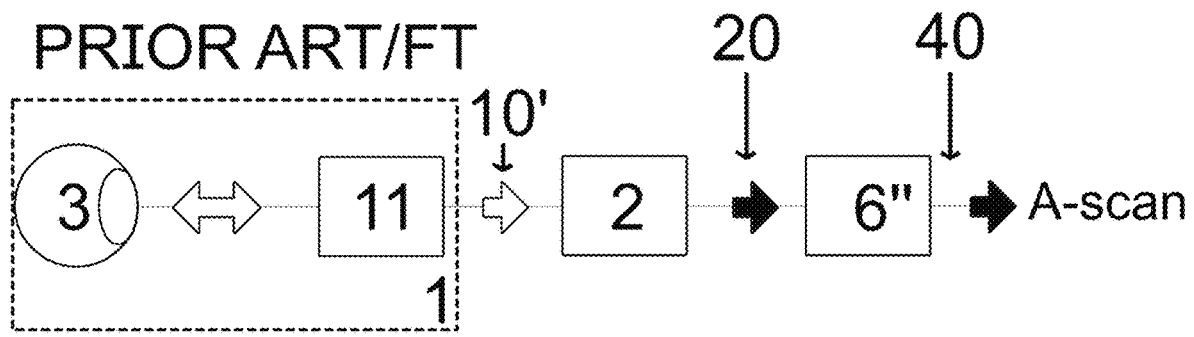
FIG. 1 shows, in diagrammatic form, the main elements of the Fourier Transform based-OCT method according to prior art.
Figure 2:
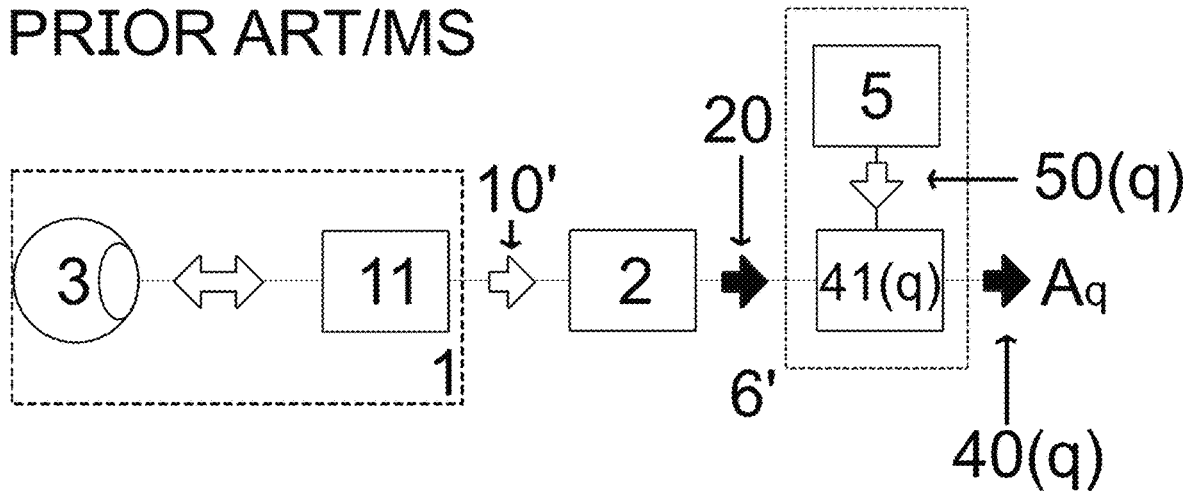
FIG. 2 shows, in diagrammatic form, the main elements of the Master Slave based OCT method according to prior art.

Various features of the embodiments described herein, as well as other objects and advantages attendant thereto, are set forth in the following description and the accompanying drawings in which like reference numerals depict like elements.

The embodiments described herein can be implemented in different versions, using a single or two interferometers.

Figure 6:
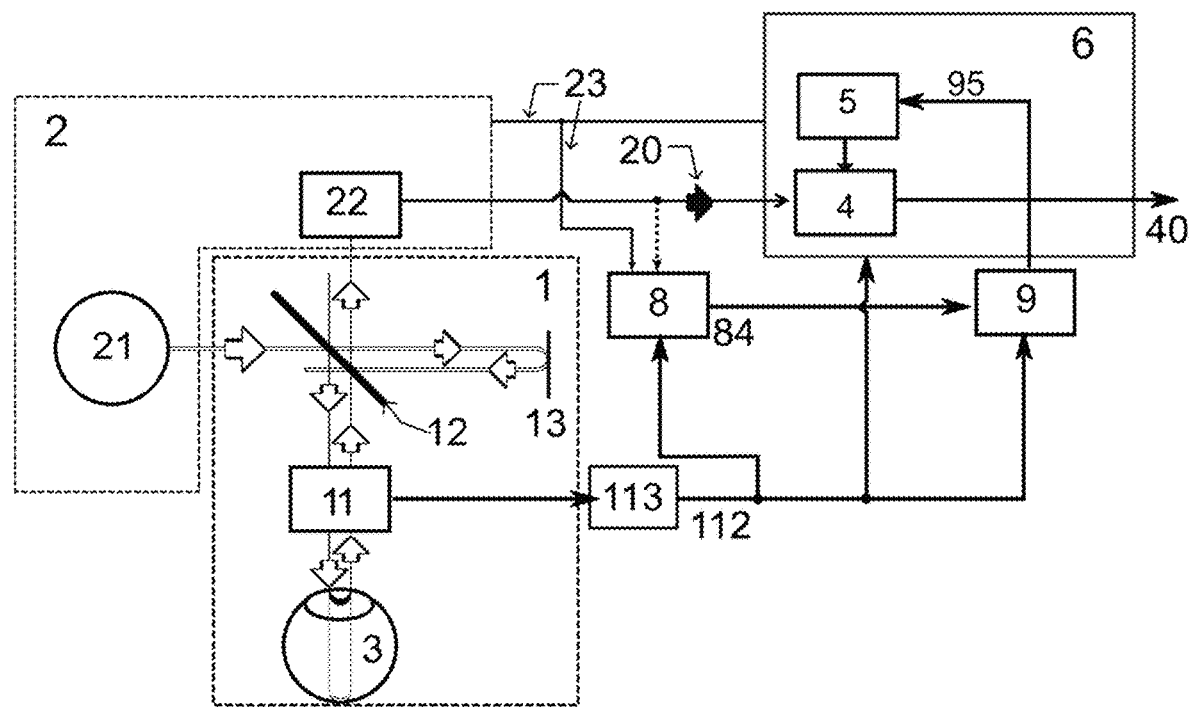
FIG. 6 shows in diagrammatic form, a first embodiment of the apparatus according to the embodiments described herein.

FIG. 6 shows in diagrammatic form, a first embodiment of the apparatus using a single interferometer, referred here as the imaging interferometer, 1 and a decoder 2. This embodiment employs a Master Slave (MS) processor, 6. This consists in a Dynamic MS comparator, 4, a Mask selector 5 and a Corrector 9. The apparatus further comprises a sensor 8 that senses the axial position of each lateral pixel, r, of the object 3 and sends such information along line 84 to be used by the corrector 9. Depending on that information, the corrector 9 controls the operation of the Mask selector 5, using a control input 95. The sensor 8 submits the information 84 on axial distance measured z to the corrector 9, in terms of the index of masks, q. Distance measured $z=q\delta$ is quantified as multiples q of the axial distance resolution interval of the OCT system, $\delta$. The numbers q are integers, with a maximum given by the axial measurable interval divided by $\delta$. The mask to be used by the MS-processor 6 depends on the variation of mask indices delivered by corrector 9, as a difference of mask indices, calculated in respect to a mask index of a reference distance, index difference i, applied to the control input 95 of the Mask selector 5.

The decoder 2 provides a synchro signal, 23, for each spectral scan enabled by the swept source 211 or the spectrometer 220, depending on the technology used, in synchronism with moving the scanned beam from pixel r ro pixel r+1, in a time $t_r$, where r=1, 2, . . . R. For instance, when using a swept source 211 or spectrometer 220 at 100 kHz, $t_r$=0.01 ms. This means that for a triangular signal applied to the fast scanner 110 of period $T_x$=4 ms, on each ramp, in 2 ms, a total of R=200 pixels are scanned along the horizontal axis X. Matching the number of scanned pixels with pixels in the C-scan image H=200 and making the image square, i.e. for V=200 lines, a frame raster of H=V=200 pixels on each ramp takes $t_F$=0.8 s. For a sawtooth signal driving the slow scanner 111, along coordinate Y (vertical), the two frames can be combined to assemble a frame of H=200 and V=400 (by flipping one of them horizontally, according to means known in the art of scanned imaging systems). The frame scanner 111 can also be driven by a stair type of signal, stepping the voltage applied to the frame scanner, to allow on each step to acquire two or more T-scans. Such an operation is presented by the end of the disclosure, to obtain angiography information, i.e. OCTA information.

These calculations give an idea of time available for the different processes, where real time correction would mean correction on the fly, during the spectral scan, i.e. in a time $t_r$, where the information from the sensor 8, utilized by the corrector 9 actuates the Mask selector 5 in real time, Quasi real time would mean correction done with some delay, either within the time of a ramp $T_x/2$ or during the period of the triangle $T_x$, or during the time of a raster $t_F$. The embodiments further presented can be adapted to operate between real time and quasi real time depending on the digital resources allocated for parallel processing. They also allow for post-acquisition, where correction is done long after the acquisition ended, i.e. after the time of a frame $t_F$, employing R memories of mask indices correction data, i, and of R channeled spectra.

Such control of operational modes is performed by a mode switch, 113, synchronized with the lateral scanner 11, that distributes enabling control signals to different blocks, sensor 8, MS-processor 6, corrector 9 and as disclosed below to different memories of signals. Different processes of acquisition, sensing, storage and correction are interleaved in the time between trigger pulses 112 in synchronism with the deflection of the scanners in 11. Processes of acquisition, sensing, storage may be inserted within a $T_x/2$ interval or spread over the whole $T_x$ or over a few $T_x$ intervals, in which case, the trigger 112 is acquired from the driving signal applied to (or from the position sensing of) the fast lateral scanner 110. Processes of sensing and correction may require longer, over the period of a frame, $t_F$, in which case, the trigger 112 is acquired from the driving signal applied to (or from the position sensing of) the slow lateral scanner 111.

Figure 7A:
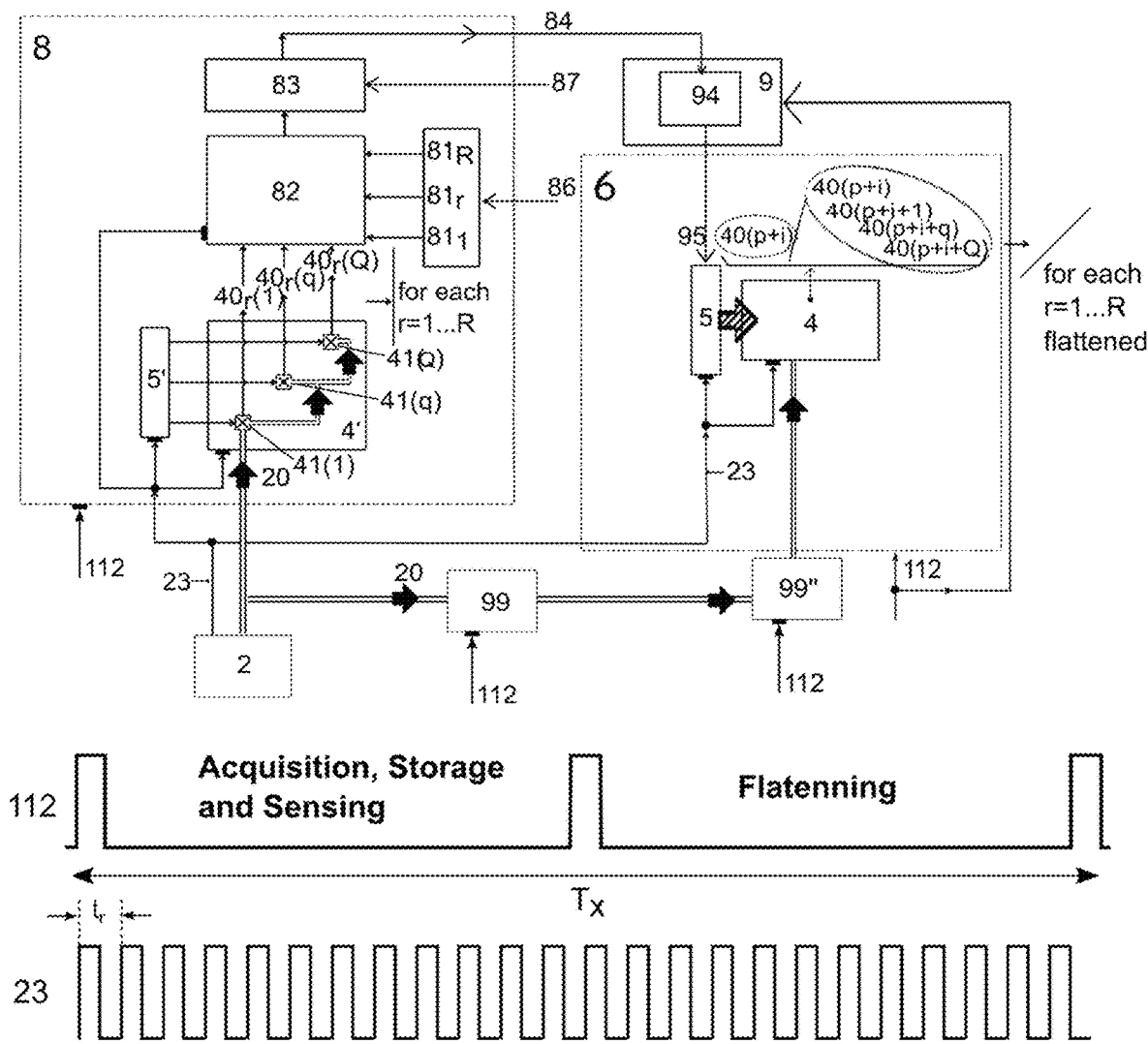
FIG. 7a shows in diagrammatic form details of the sensor and of the MS-processor in FIG. 6 where the sensor employs the same signal as that used for OCT imaging and implements edge detection and segmentation via MS.
Figure 7A:
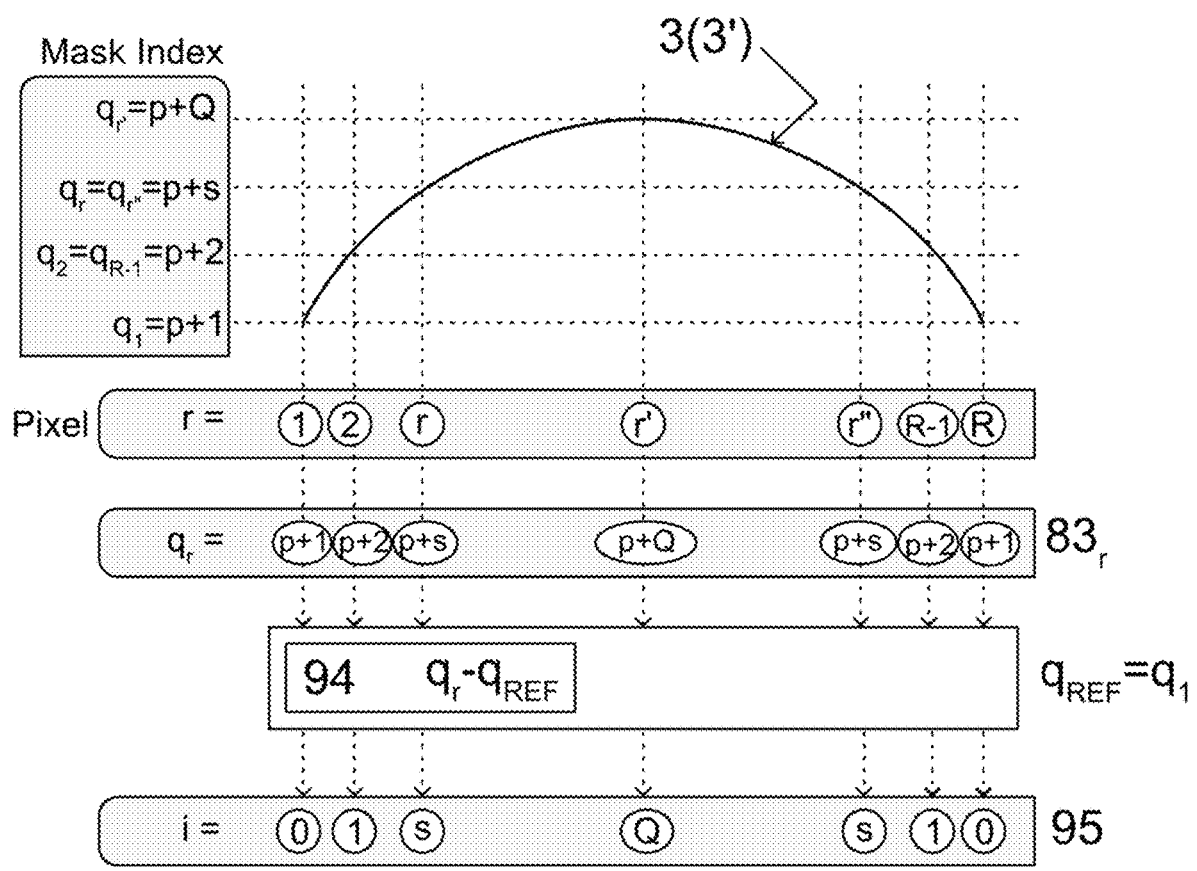
Figure 7B:
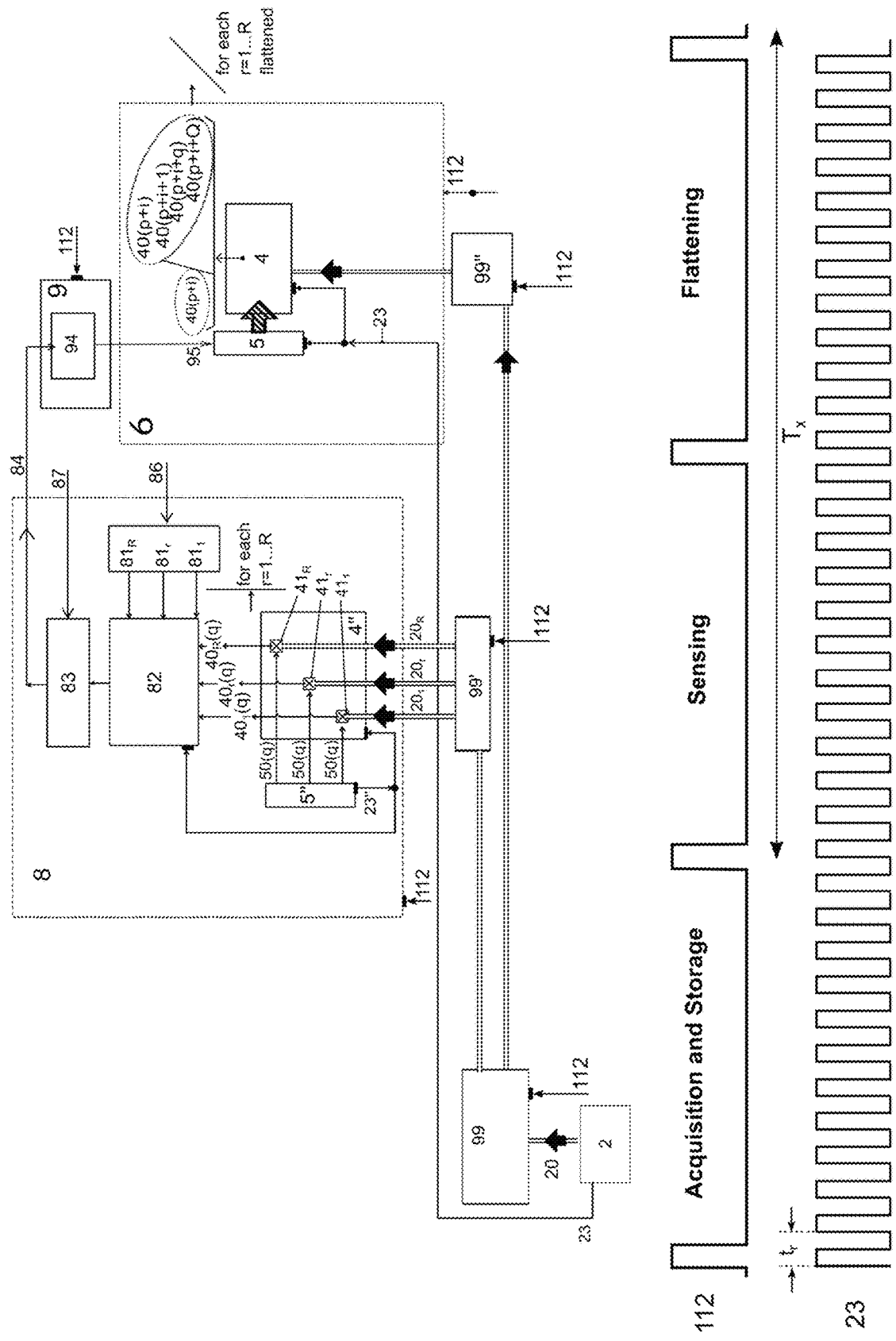
Figure 7B:
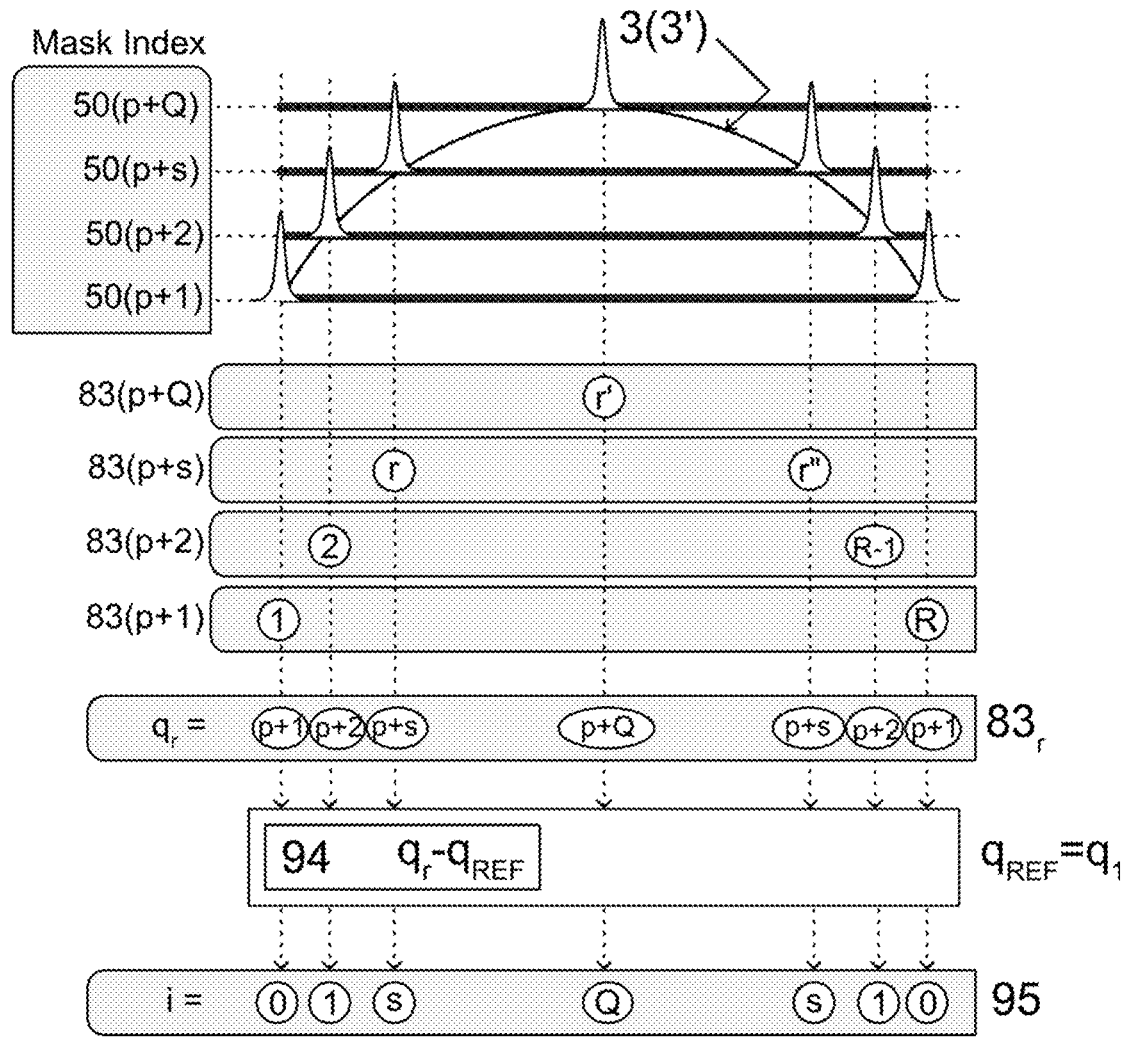
Figure 7C:
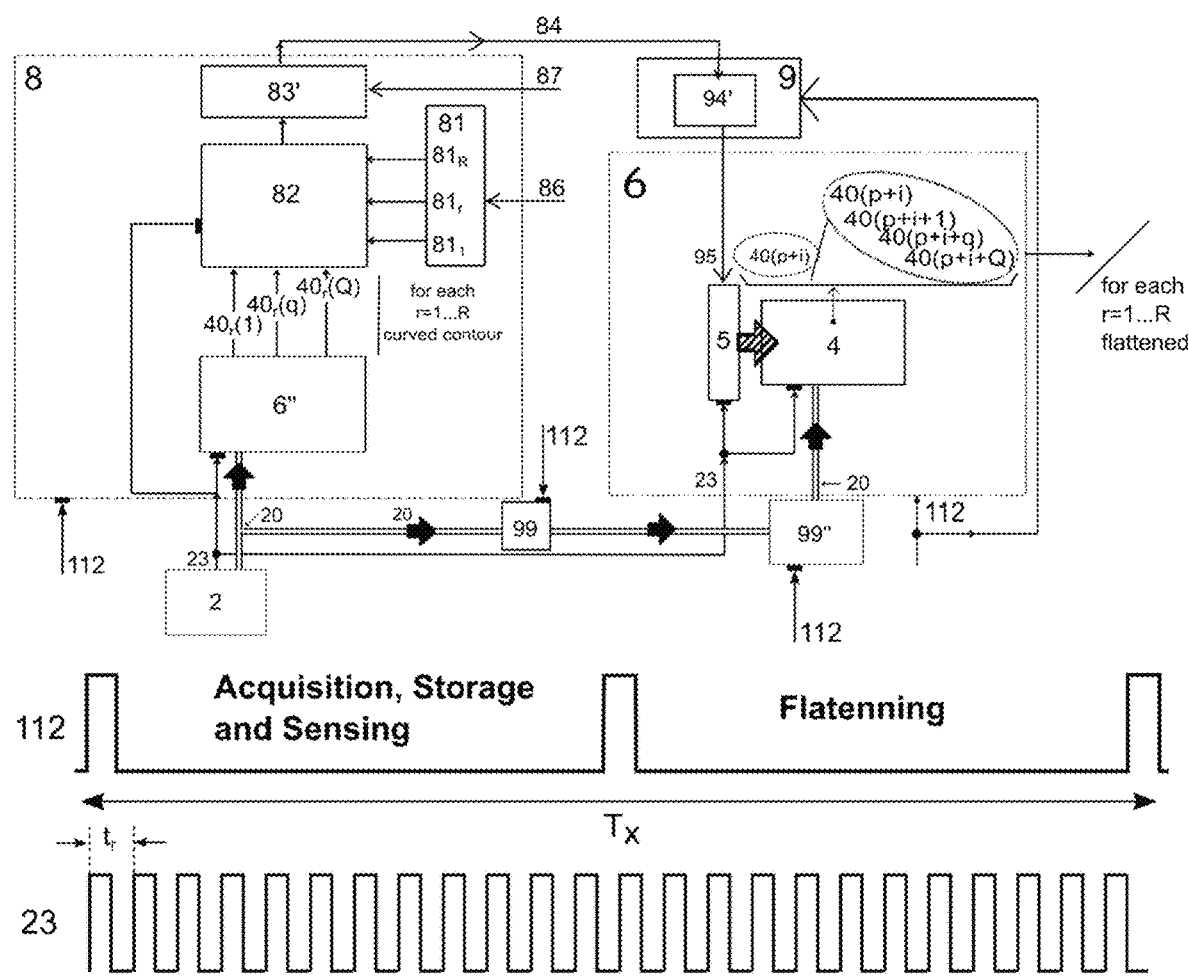
FIG. 7c shows in diagrammatic form another version of the sensor in FIG. 6, that implements edge detection and segmentation via FFT.
Figure 7C:
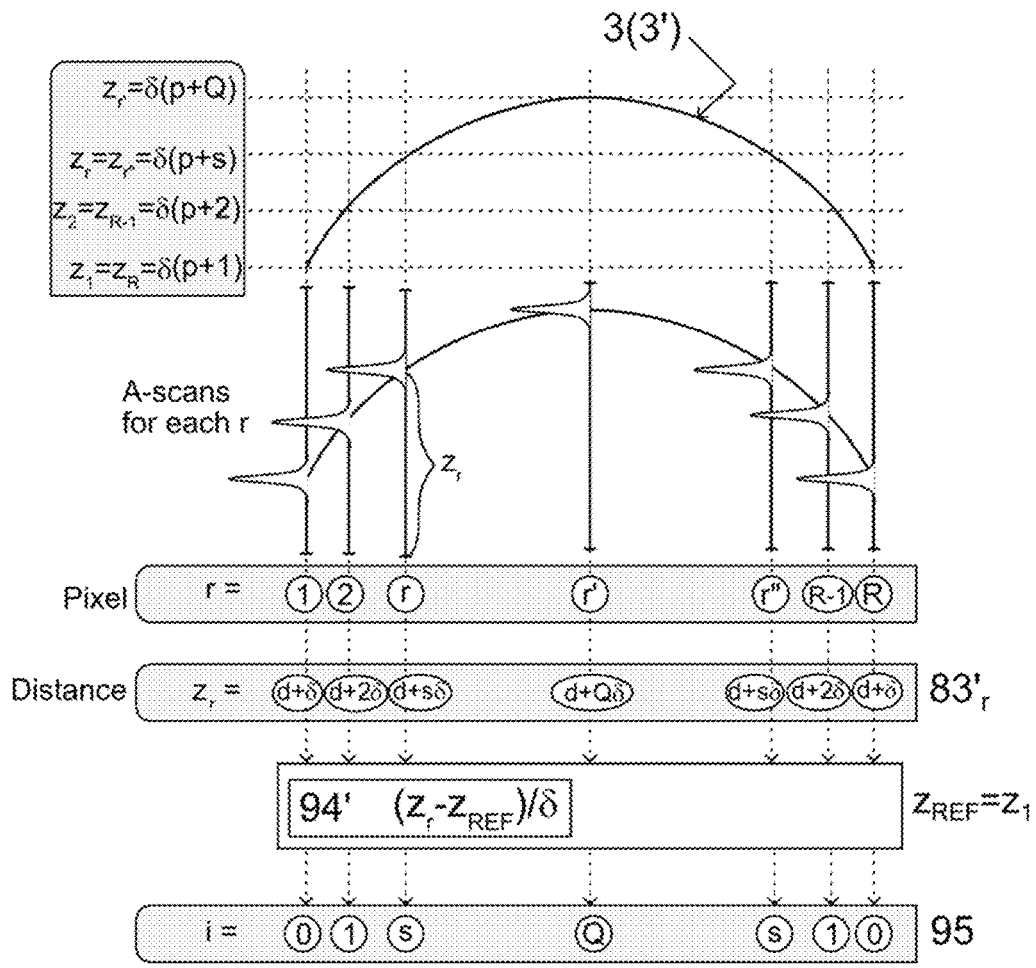
Figure 11:
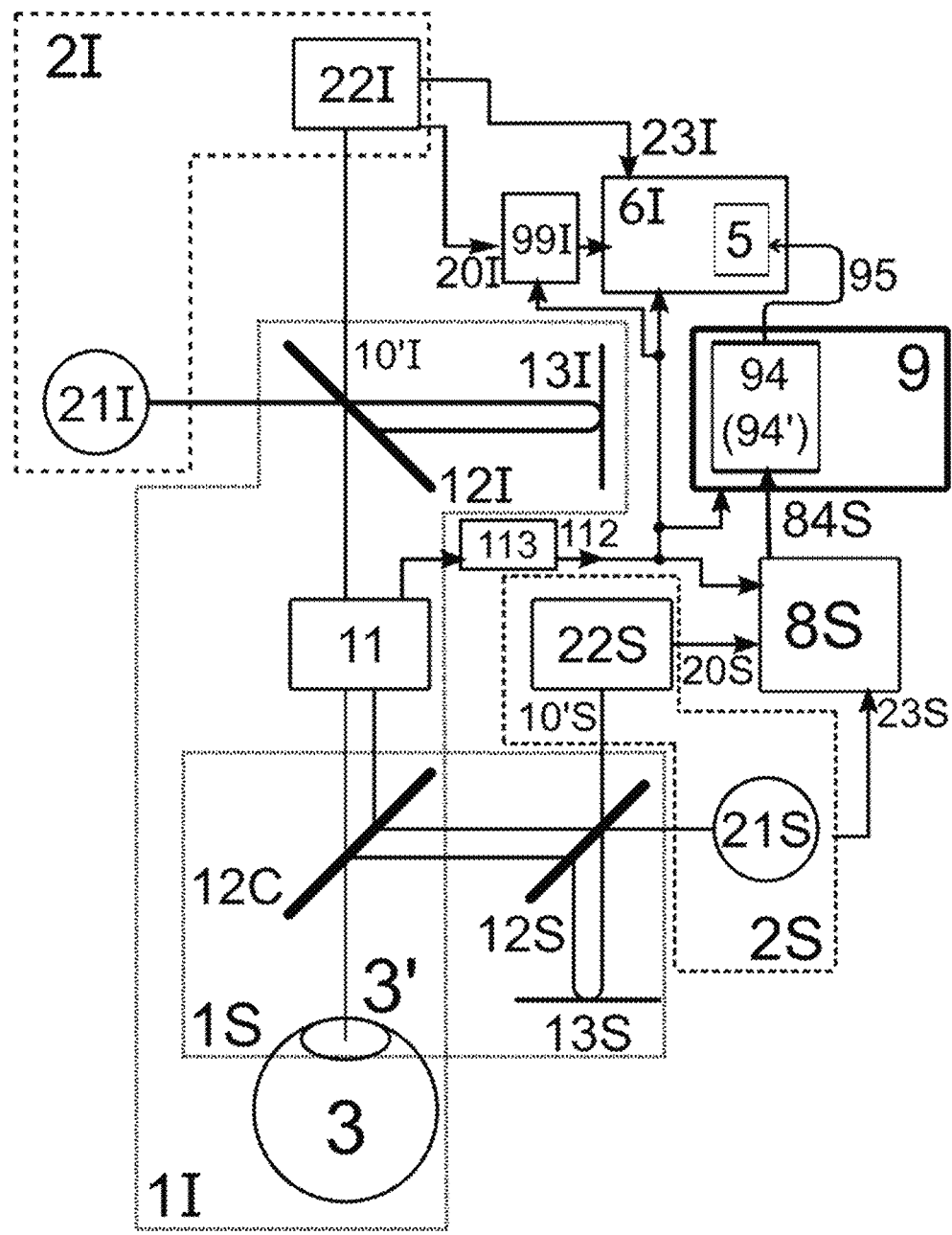
FIG. 11 discloses in diagrammatic form, a second embodiment of an imaging OCT apparatus, where the sensor uses a 2nd interferometer.
Figure 12A:
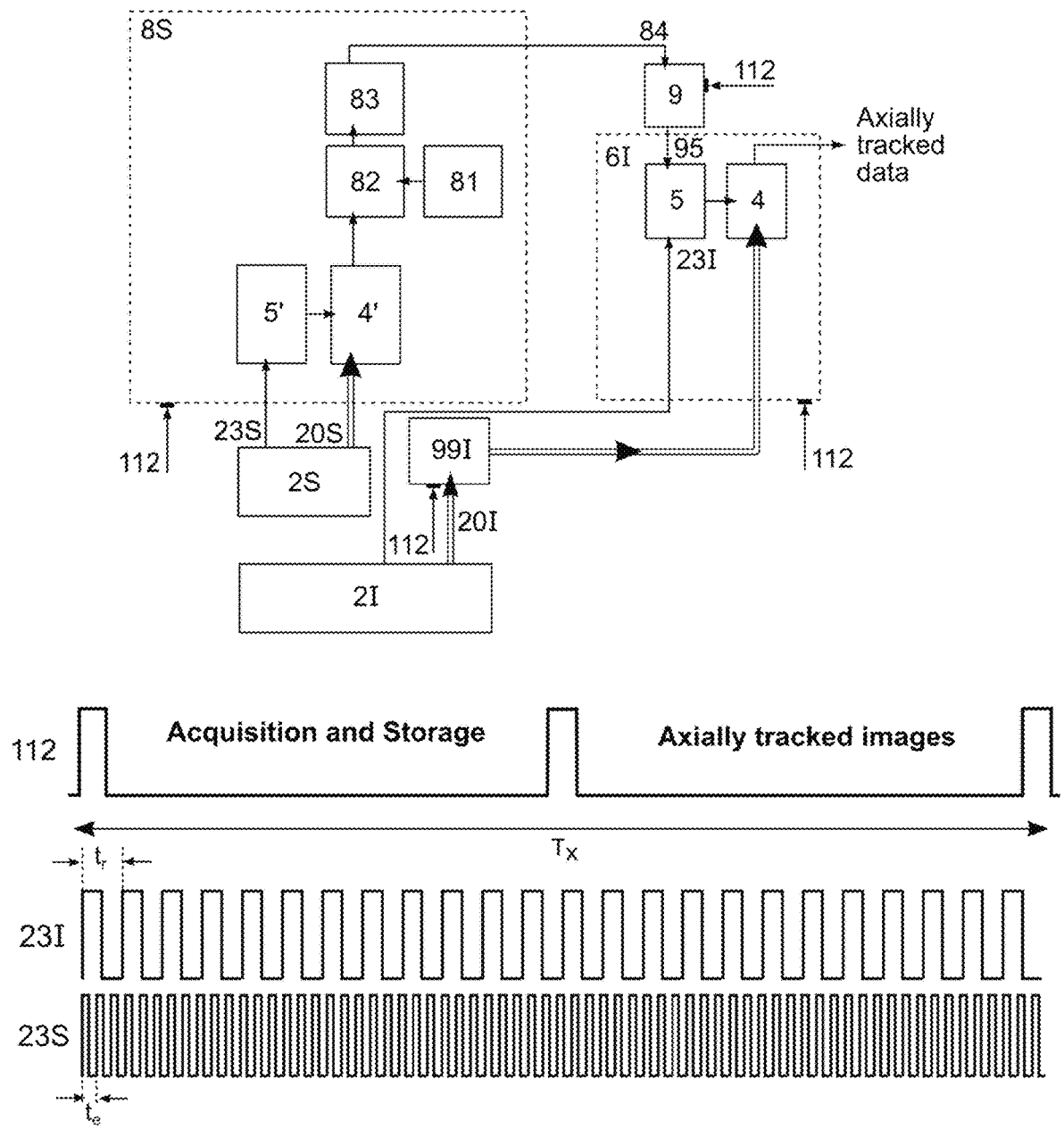
FIG. 12a shows in diagrammatic form details of the sensor in FIG. 11 and of the MS-processor where the sensor employs signal from a $2^{nd}$ interferometer and implements axial sensing via MS.
Figure 12A:
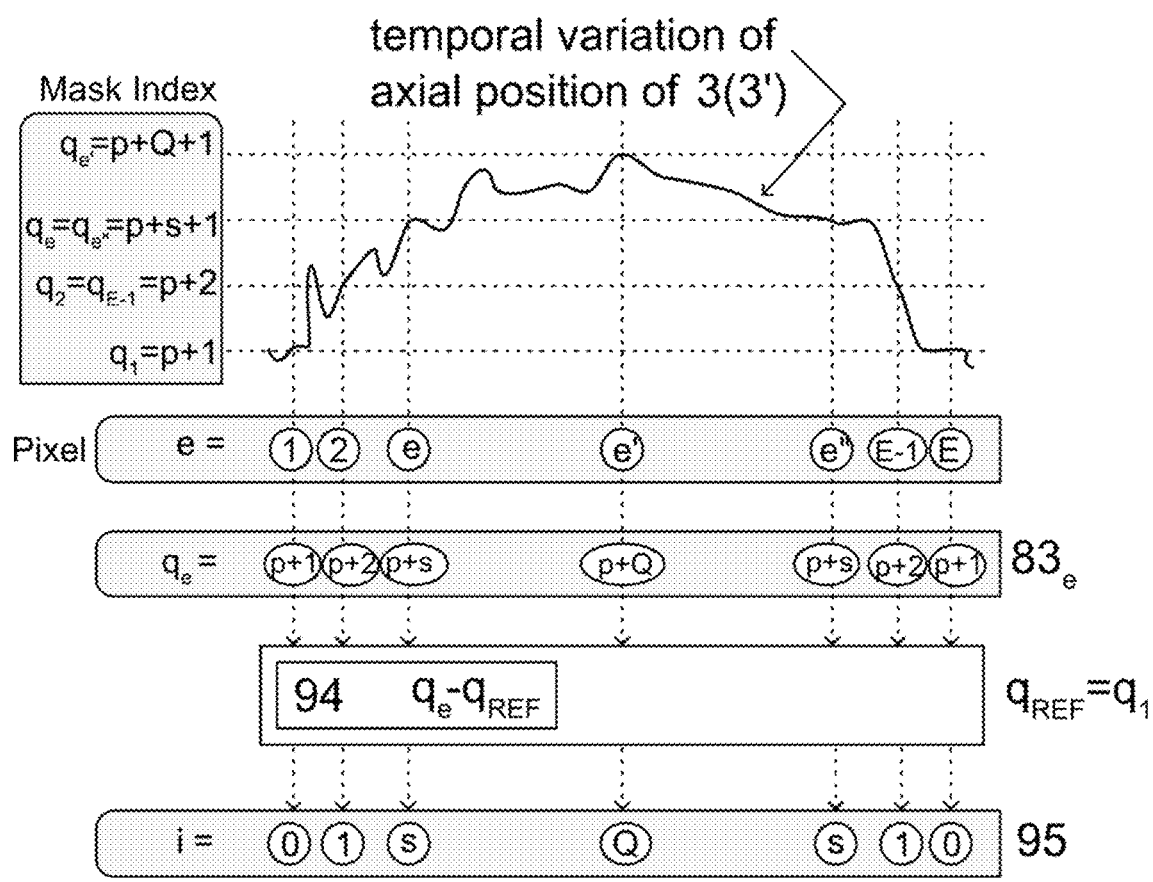
Figure 12B:
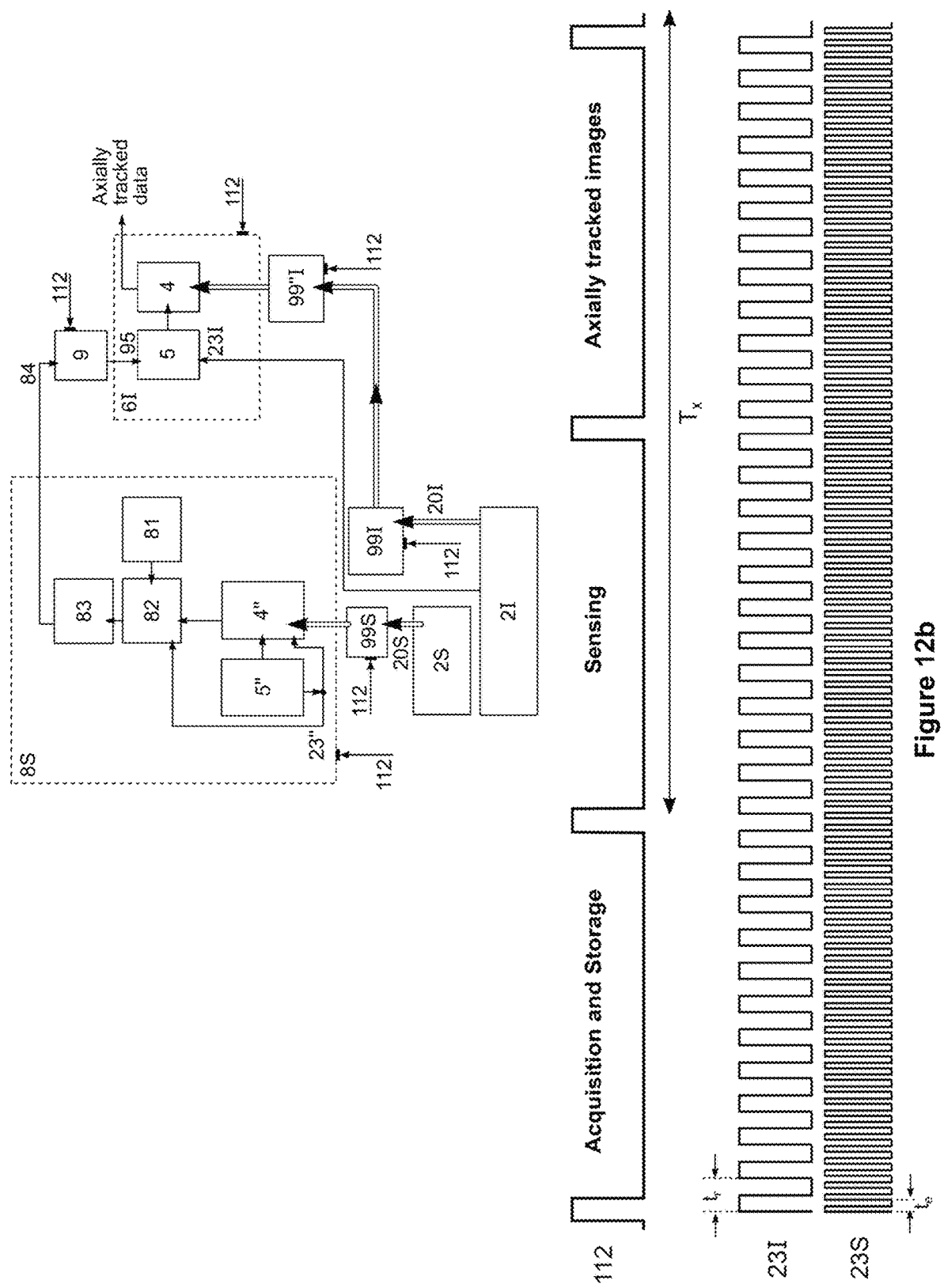
Figure 12B:
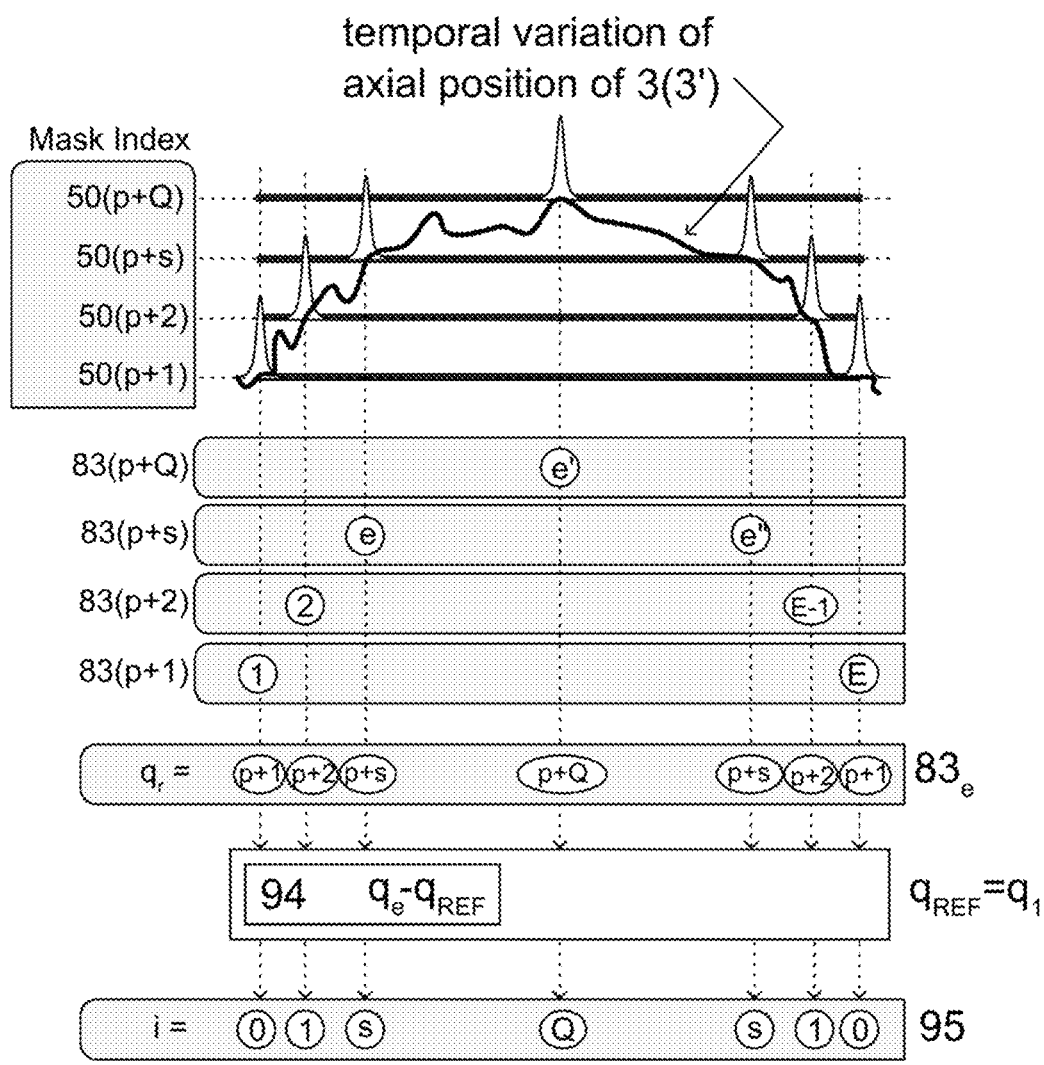
Figure 12C:
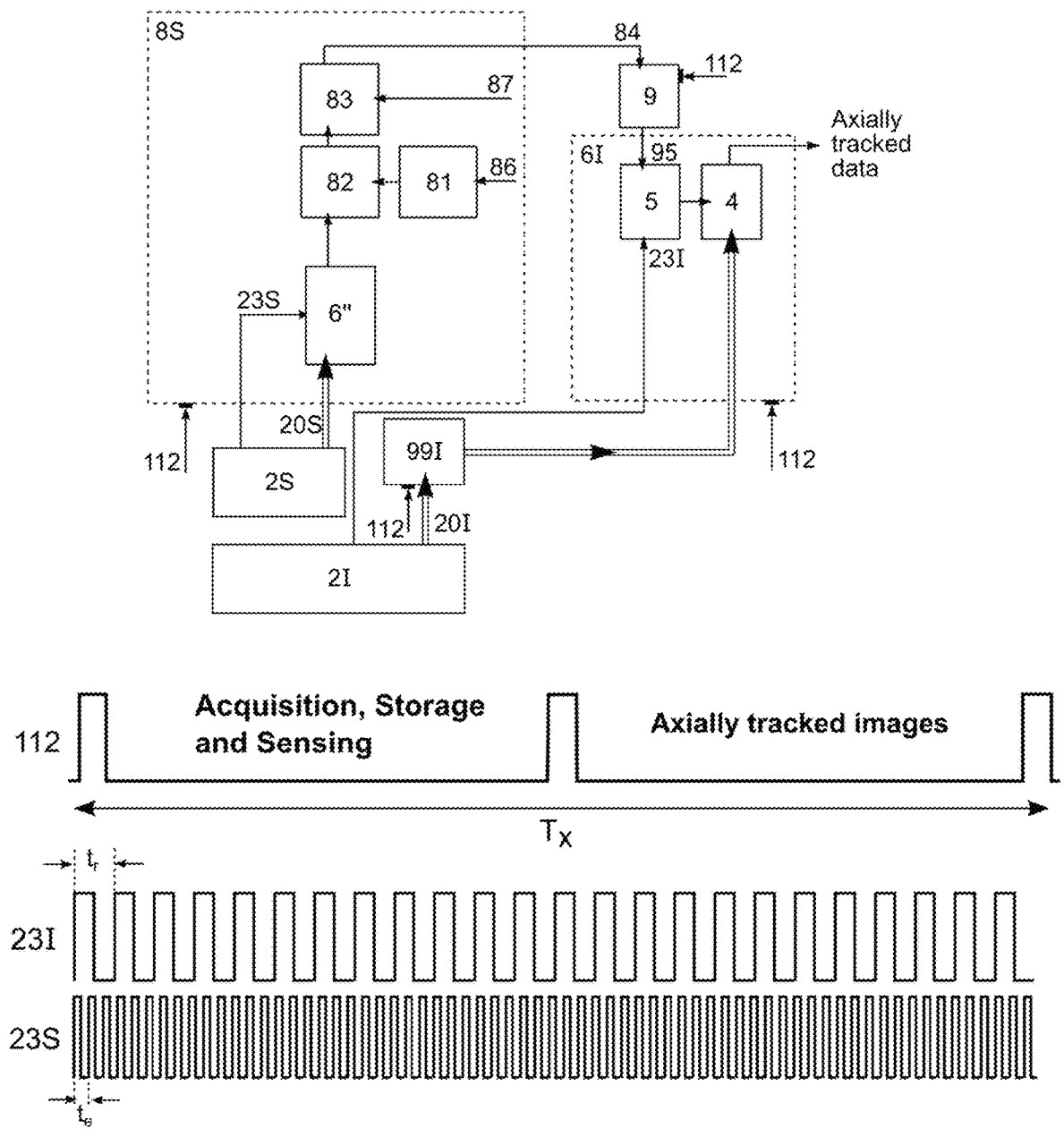
FIG. 12c shows in diagrammatic for, another version of the sensor in FIG. 11, that implements axial sensing via FFT.
Figure 12C:
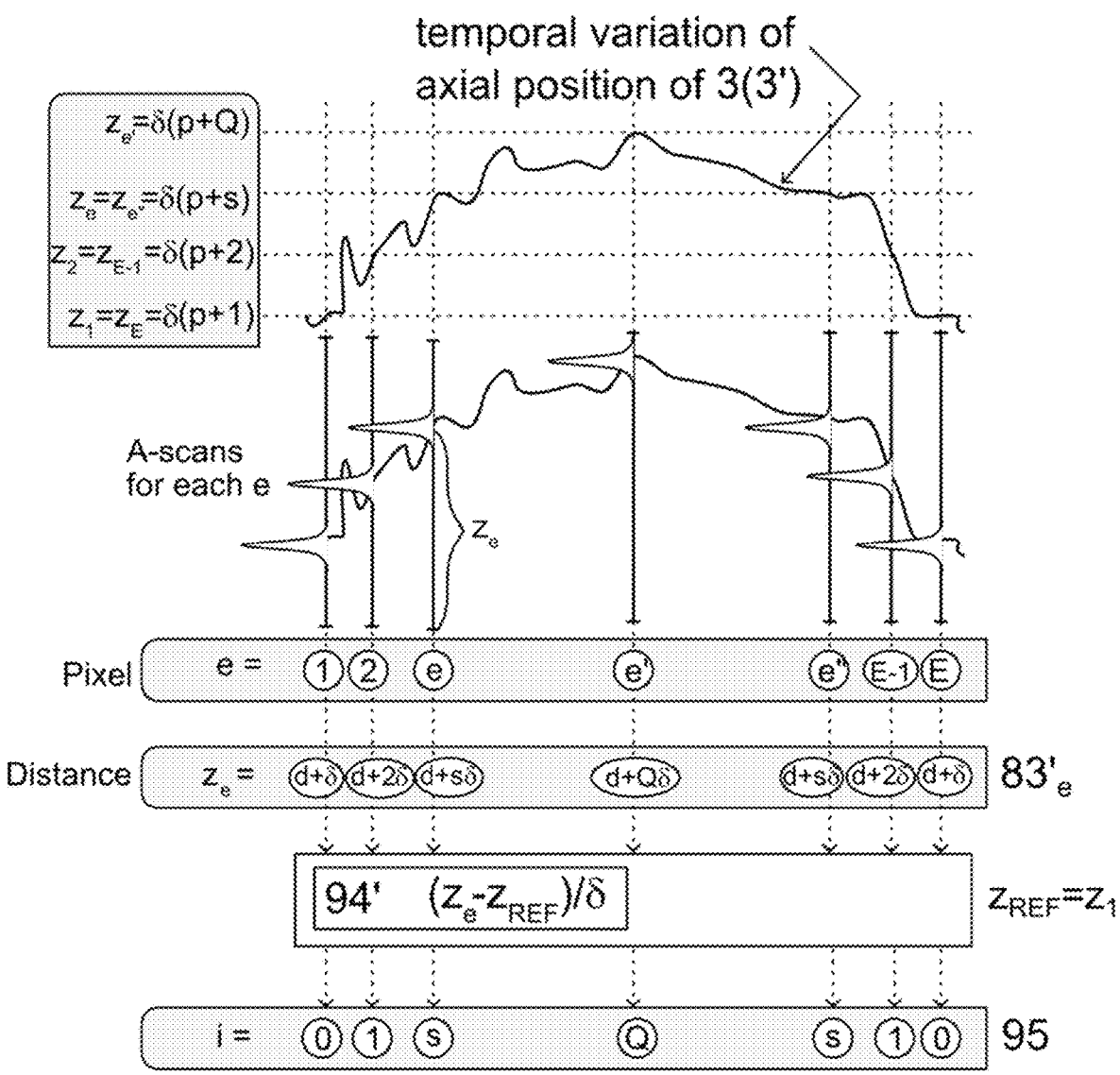
Figure 13:
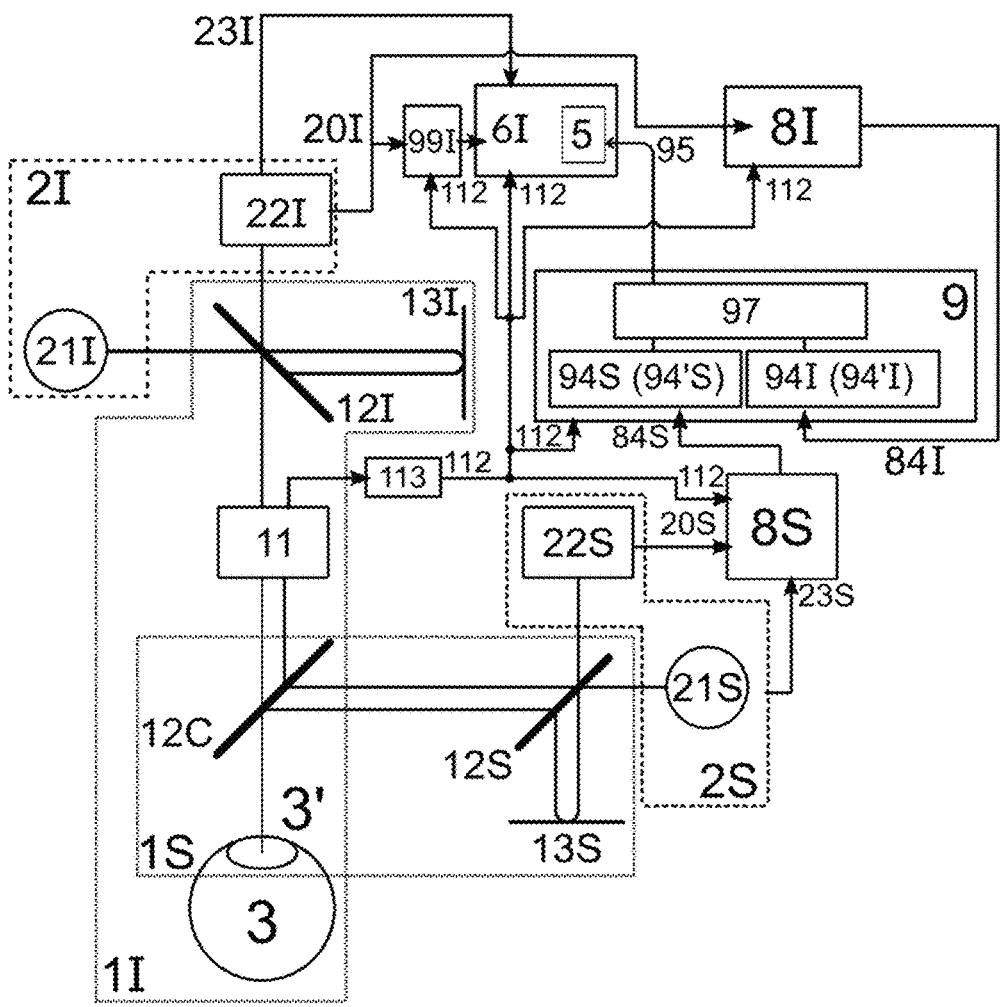
FIG. 13 illustrates another embodiment of an imaging OCT apparatus using two sensors.

The sensor can use signal 20 from the imaging interferometer 1, as in the embodiments shown in FIG. 7a, FIG. 7b and FIG. 7c or can use a separate interferometer, as in the embodiments in FIG. 11 and FIG. 13. The sensors can use for segmentation either MS, such as in FIGS. 7a, 7b, 12a and 12b or FFT as disclosed in FIGS. 7c and 12c.

As disclosed further below, different embodiments of the MS-processor are possible adapted to optimize the time of response to different tasks, depending on the need to generate C-scans or B-scans.

Figure 6A:
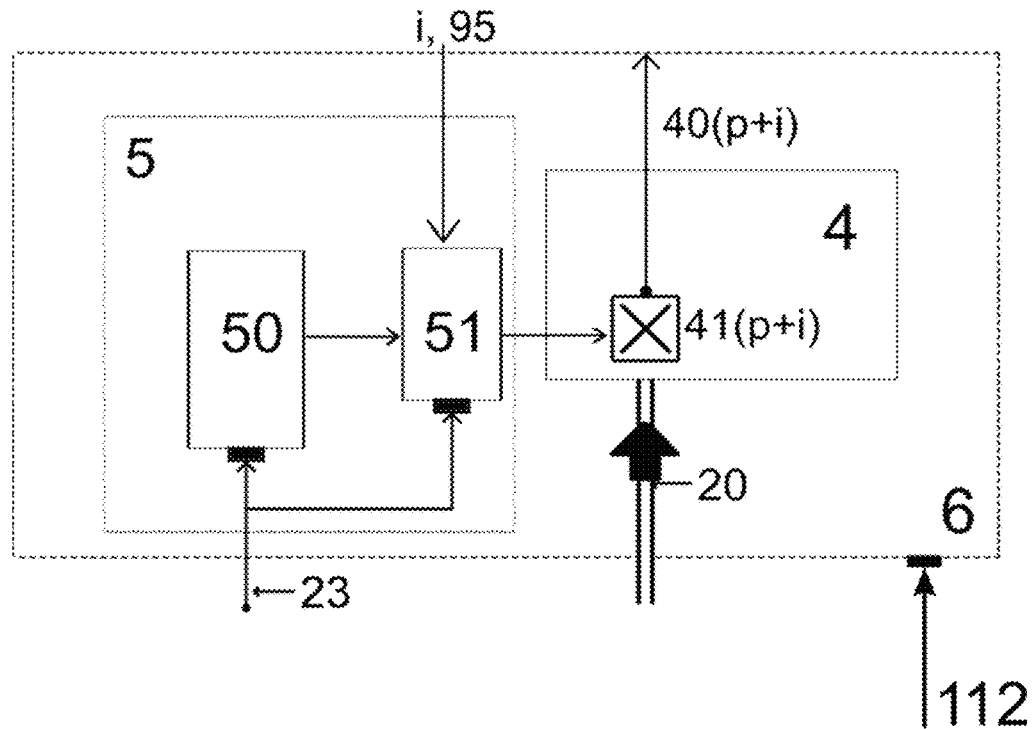
FIG. 6a shows in diagrammatic form, a first embodiment of the MS-processor to be used by the OCT apparatus in FIG. 6.

FIG. 6a details a first embodiment of the MS-processor 6, where a single mask is calculated by calculator 51 based on functions g and h (please see section 2.2.1) stored in storage 50, hence a single comparator 41 is needed in the Dynamic MS comparator 4. This embodiment is to be used for flattening of C-scans. When C-scans OCT images are generated, a single mask or a few only are needed for each spectral event selected by 23. This performs in synchronism with the optical beam scanned by the scanner 11 over each pixel r.

Because a single mask is necessary or a few only, it is more advantageous to avoid transfer of data between a storage and MS-calculator 41(q) and faster operation is achieved by calculating the mask needed on the fly, as disclosed in this embodiment. For each pixel r, input 95 provides a correction of the mask index p, from p to p+i to produce via the MS protocol the complex reflectivity 40 for the depth of the mask p+i, 40(p+i).

Figure 6B:
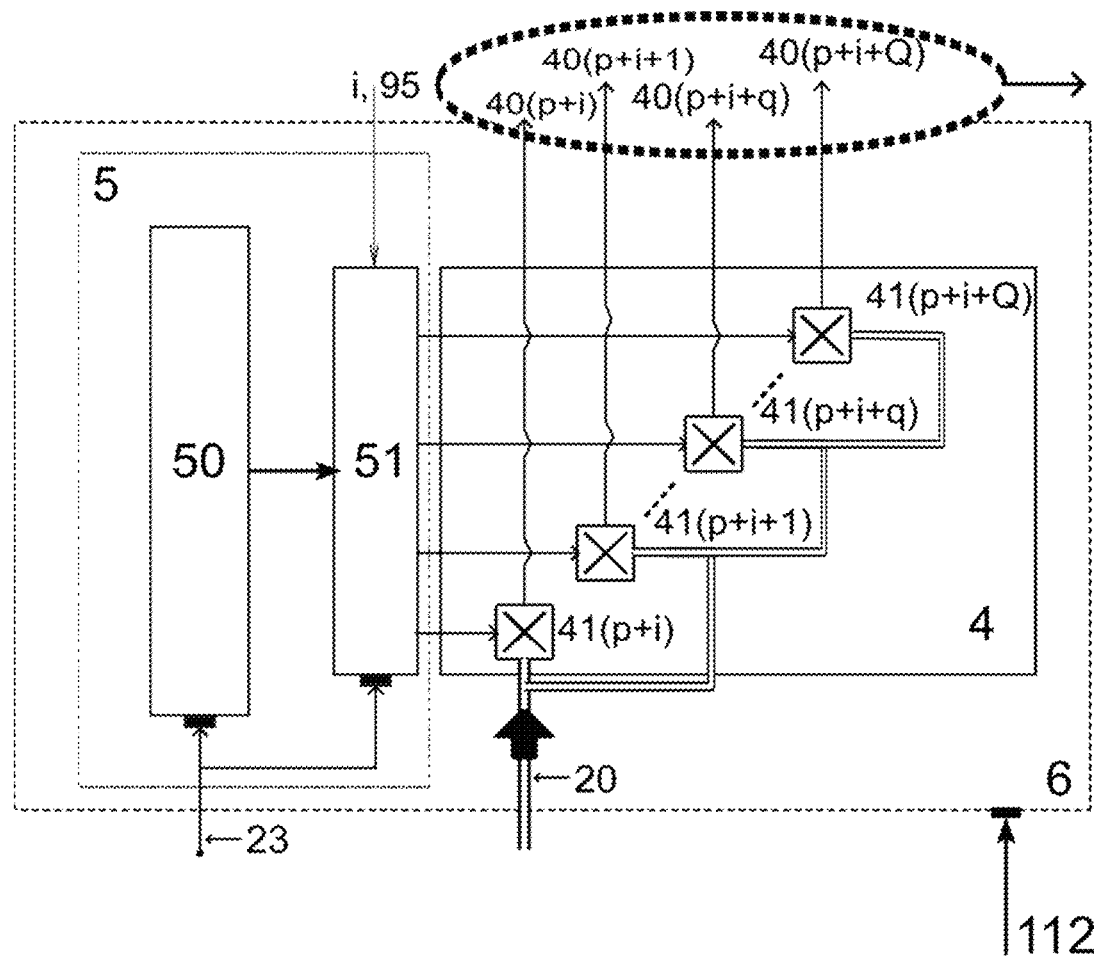
FIG. 6b shows in diagrammatic form, a second embodiment of the MS-processor to be used by the OCT apparatus in FIG. 6.

FIG. 6b details a second embodiment of the MS-processor 6, where Q masks are calculated on the fly, using calculator 51 based on functions g and h stored in storage 50. This embodiment is to be used for correction of axial movement in B-scans or in those situations where a small number of Q masks is needed in which case it is more advantageous to calculate the masks than transferring them from a storage of masks.

Dynamic changes of many masks used in a single spectral scan may be slow in case a large number Q of masks are used or their number of sampling points, M is high. In a FPGA environment this may not be a problem, but for a graphic cards environment often transfers from memories take time. This issue is addressed in the embodiment of the MS processor in FIGS. 6a and 6b where the single mask needed in FIG. 6a and the Q masks needed in FIG. 6b are calculated as they are needed for each spectral scan event r, synchro 23. A single reflectivity, 40(q) is obtained per spectral scan event, r in FIG. 6a, or a set of Q reflectivity values, 40(q) in FIG. 6b. For each pixel r, input 95 provides correction of the mask indices to be used from p+q to p+i+q, to produce via the MS protocol the complex reflectivity values 40 for the depths of the masks p+i+q, 40(p+i+q).

Figure 6C:
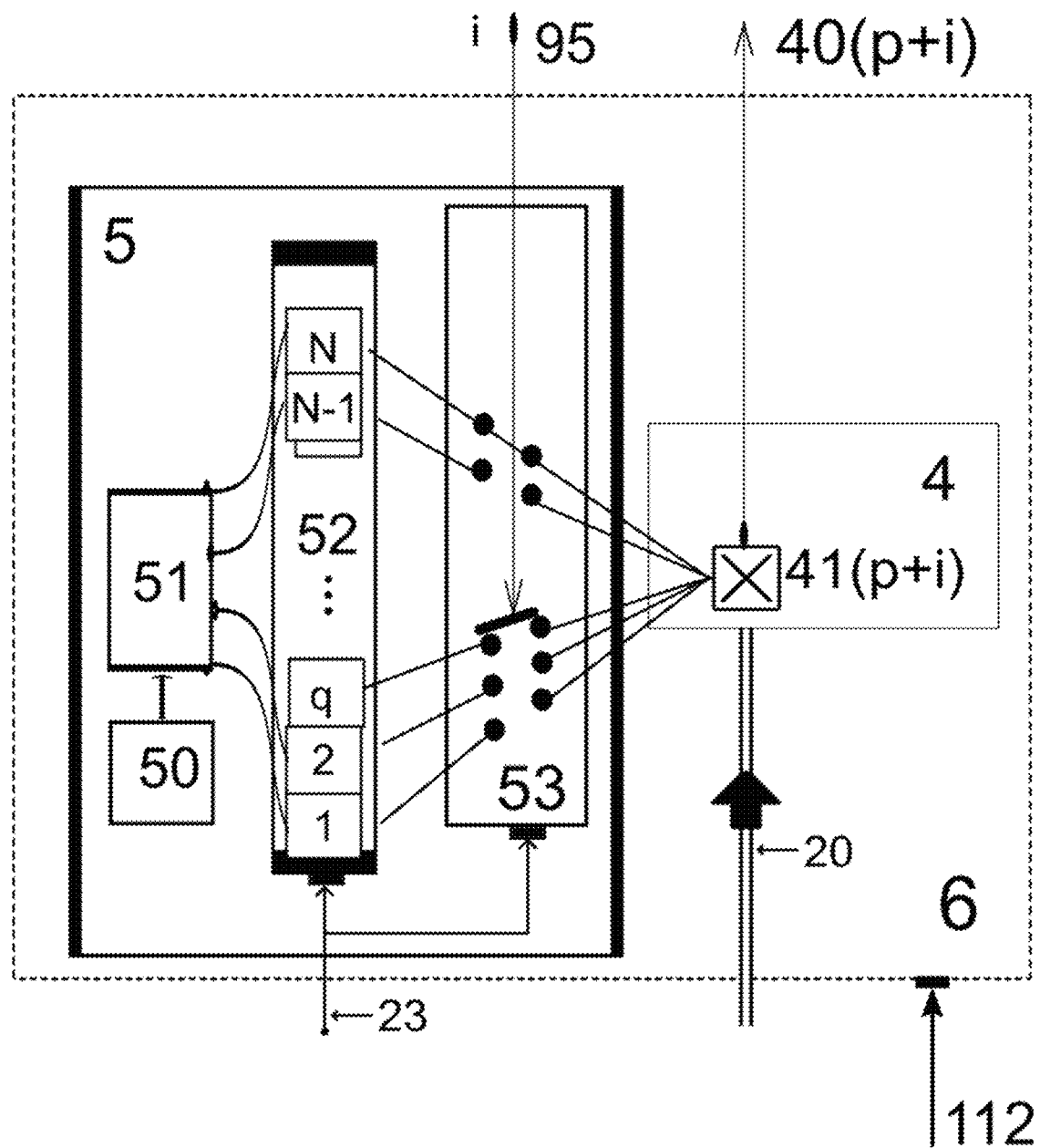
FIG. 6c shows in diagrammatic form, a third embodiment of the MS-processor to be used by the OCT apparatus in FIG. 6.

FIG. 6c details a third embodiment of the MS-processor 6, employing stored masks. The Mask Selector 5 contains two storages 50 and 52 and a calculator 51. The storage 50 stores the functions g and h. Using these functions, N masks are calculated by the block calculator, 51, according to the procedure described in the US patent D2, and placed to be used at the slave stage in the storage, 52, of N masks. This is interfaced with the Dynamic MS comparator 4 via a Distributor 53. A single mask from the storage 52 is selected by the distributor 53, under the control of the corrector 9 that delivers the correction, i, for the sensed axial position via line 95. This embodiment is to be used for flattening of C-scans. For each spectral scan triggered by 23, a single multiplication operation is needed, of the channeled spectrum 20 with a single mask selected by distributor 53. A single MS-calculator 41 is needed in the Dynamic MS comparator 4 as well.

When a single en-face image is needed only, such as in rapid investigations in ophthalmology and surgery, flattened, irrespective of the tissue curvature and axial movement, the MS-processor 6 in FIG. 6a and FIG. 6c performs correction faster than the prior art based on FFT.

Figure 6D:
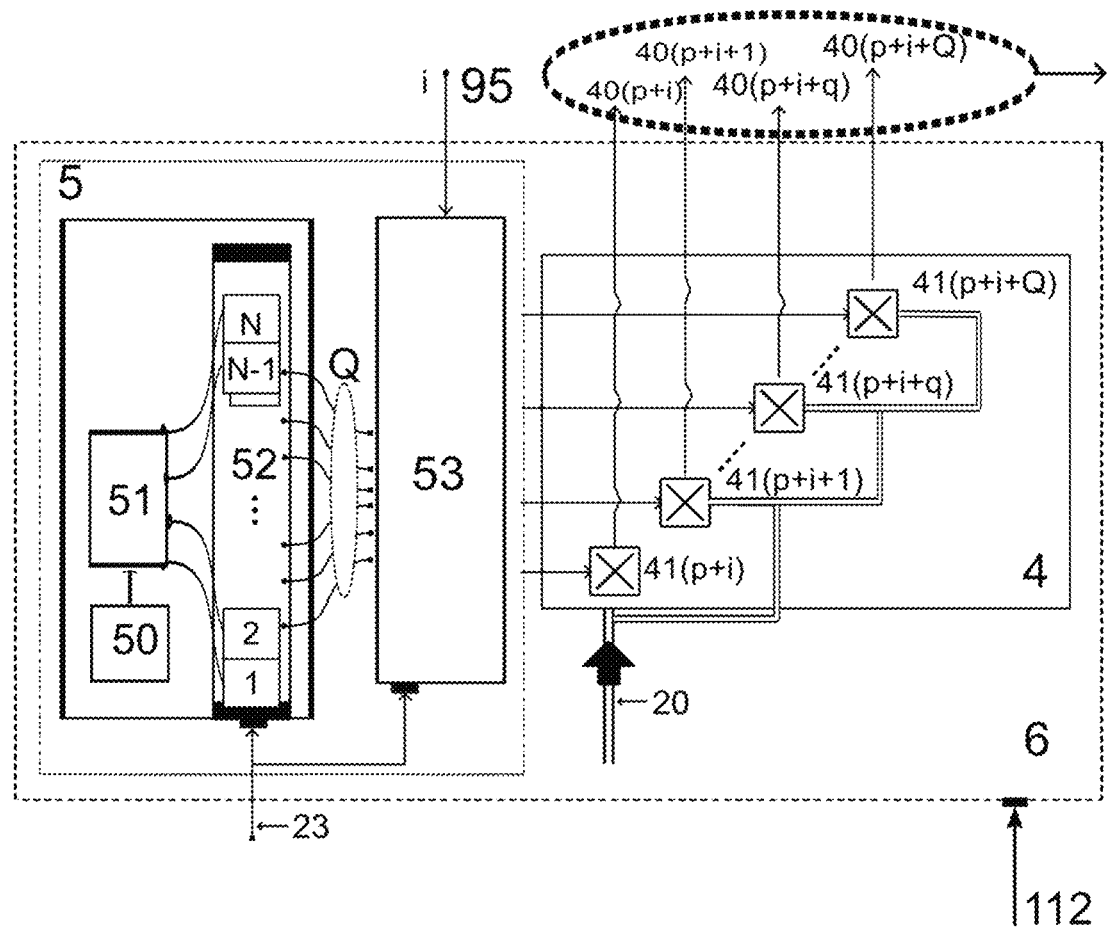
FIG. 6d shows in diagrammatic form, a fourth embodiment of the MS-processor to be used by the OCT apparatus in FIG. 6.

FIG. 6d details a fourth embodiment of the MS-processor 6, employing stored masks and performing dynamic swap of Q masks. This embodiment is to be used for correction of axial movement in B-scans. Distributor 53 operates differently than for the function in FIG. 6c. The Dynamic MS comparator 4 consists in several two-input MS-calculators 41 that receive channeled spectrum signal 20 from decoder 2. The other inputs receive mask signals from the Mask selector 5. The swap of sets of masks is performed under the signal coming from the corrector 9, that delivers the correction i, for the sensed axial position via line 95.

The range of masks, N, calculated in FIG. 6b or stored in the storage 52 in FIG. 6d is adjusted depending on two initial settings, characteristic for the task of dynamic correction: (i) maximum axial range given by N, versus (ii) the axial range for tracking and imaging, given by Q. For instance, let us consider a maximum axial range covered by N masks of 2.048 mm, i.e. N mask indices, with N=2048 for an axial resolution interval of the OCT of δ=1 micron. To allow for drifts, the tracking rage is less or much less than the tracking range, therefore Q is less or much less than N, for instance Q=1024, i.e. covering a tracking range of 1.024 mm inside the system axial range capability of 2.048 mm. But if the object exhibits better axial stability than plus minus 0.512 mm in the example above, for instance, within a much reduced interval of plus minus 5.12 microns axial variations, then only Q~10 masks will be necessary to track the object. The lower Q number, the faster the system response, implementing axial tracking, as a lower number of digital operations is necessary, in which case embodiment in FIG. 6b may be adopted.

To cover an axial range of N depth points, the FFT utilizes 2N samples and performs ~2N $\log_2$(2N) operations, according to Cooley-Tukey radix-2 implementation.

The MS protocol requires ~$2N^2$ operations to generate reflectivity values in N axial slots.

To cover an axial range of Q<<N depth points, MS requires 2NQ operations. In the example above, where Q=10 and N>512=$2^9$, 2NQ is smaller than 2N $\log_2$ N, i.e. processing is faster than performing Fourier transformations. The comparison above does not include the time required for data resampling required before calculating the FFT, in which case MS becomes comparatively faster than a FFT for a larger Q value. Calculations above are only illustrative, if complex master slave process is compared with complex FFT, then other coefficients should be used in terms of the number of operations required by MS and FFT.

Figure 3:
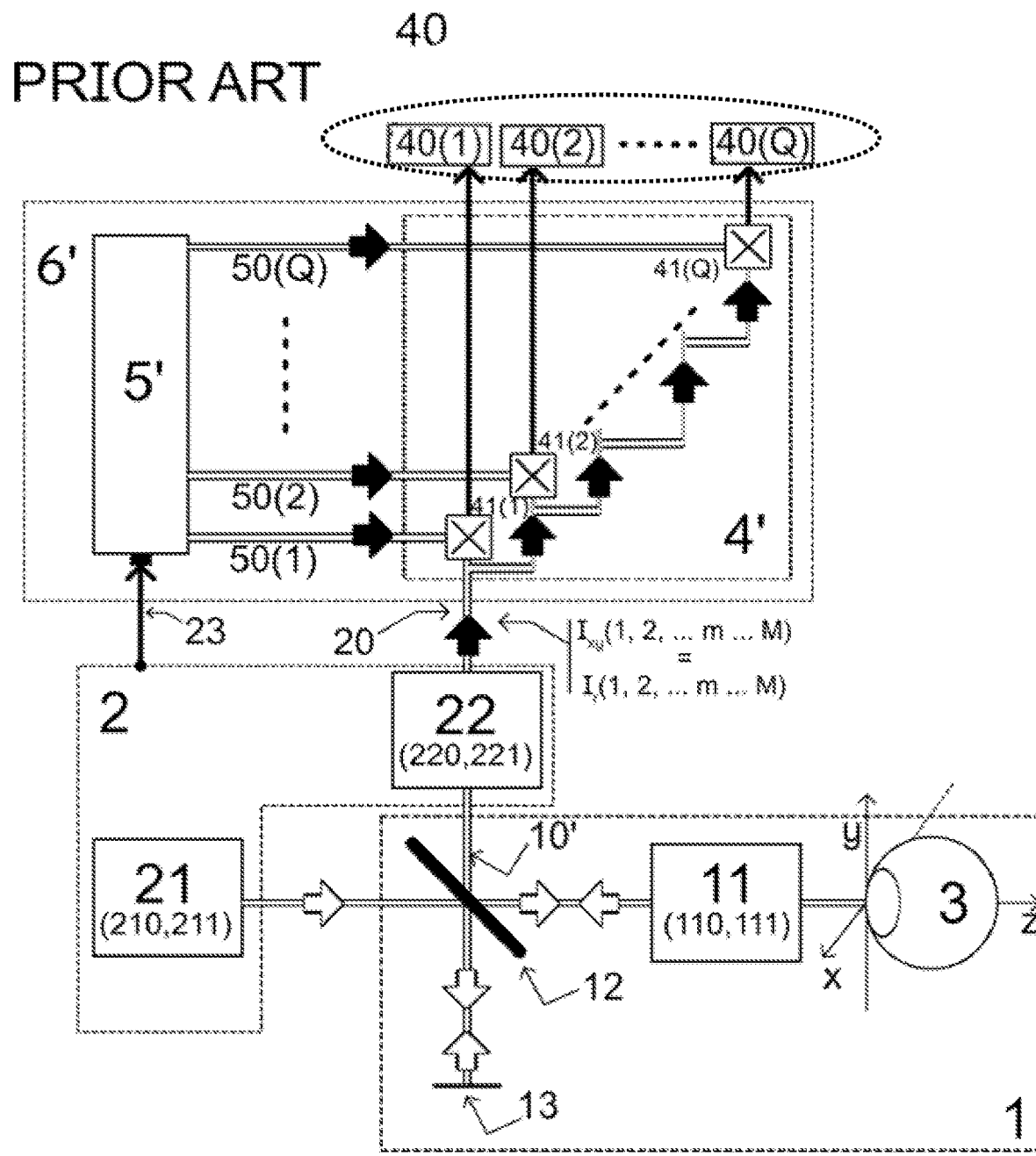
FIG. 3 shows a more detailed configuration of the MS-OCT method according to prior art.
Figure 4:
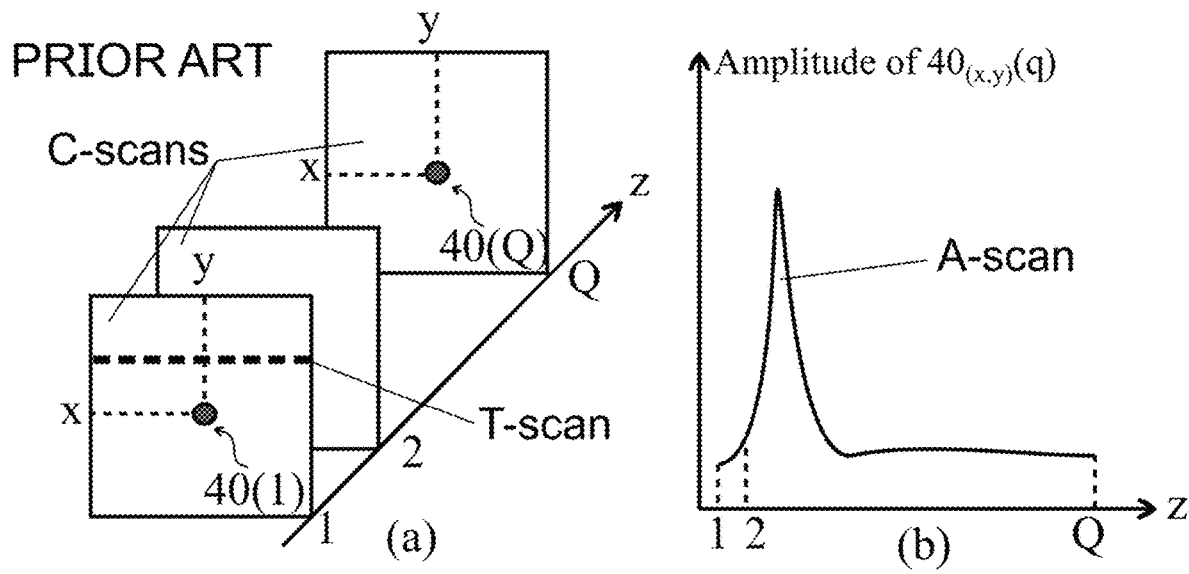
FIG. 4, illustrates the terminology of scanning in OCT, to be used throughout the disclosure.

In comparison to the prior art in FIG. 3, the MS-processor according to the embodiments in FIGS. 6a, 6b, 6c, 6d performs dynamic allocation of a mask or masks to the Dynamic MS comparator 4. As another distinction is that in prior art, for imaging, the number of masks in the storage of masks 5' in FIG. 3 was equal to that of MS-calculators 41. Also, for imaging, the number of masks used could exceed the minimum number 2N determined by the spectral purity of the decoder 2, i.e. having more than a MS points over each resolution interval δ, along the depth. If the decoder outputs M spectral pixels for each spectral readout, r, the maximum number of resolvable OPD (depth) values is M/2=N in storages 52. So the number of maximum orthogonal masks is M/2. In the practice of MS-OCT, the number of masks used can exceed M/2 for phase calculations, for speckle reduction, with the disadvantage of lengthening the calculation time. For the scope of axial tracking, a smaller number of masks can be employed, and this number should be kept at a minimum to enable quick reaction to corrections, aimed by the embodiments described herein, of either curvature of object or axial movement of the object. Dynamic allocation of masks allows for a large number of masks to be employed for imaging when the axial position is stable, with reduction during axial position fluctuations.

Therefore, in FIG. 6c and FIG. 6d, N means the minimum number M/2 of masks needed to cover the axial range, as determined by the spectral purity of the decoder 2, i.e. for M number of pixels in the camera of the spectrometer or M number of spectral distinguishable slots of the swept source.

In different implementations as disclosed below, the MS-processor 6 may be used in different scenarios in terms of selection of masks from the Mask selector 5. A set of Q masks from within the set of N masks is used to generate cross section OCT (B-scans), where the indices in the set used are from p, to p+Q in FIG. 6b and FIG. 6d. When generating en-face OCT (C-scan) images, a few masks or a single mask may be used, such as in FIGS. 6a and 6c. For displaying a few C-scans, two or more masks are used, in which case their indices may not be in continuous succession, but any number out of the Q set. For instance, the user may display an en-face OCT image from the inner limiting membrane, from the ganglion layer or from the RPE, when imaging the retina. These layers are separated by tens to hundreds of microns, hence three different mask indices will be used. This is a clear advantage for the MS processing, distinct from applying a FFT that calculates all layers followed by selection of those useful. Here, a smaller number of operations are needed as calculations are done for the layers required only.

For instance, let us consider simple examples, such as the storage of masks 52 equipped with N=10 masks, indices 1, 2, 3, ... 10. For continuous depth ranges, such as needed in B-scans, a set of Q=5 masks are used, such as 4, 5, 6, 7, 8, or 3, 4, 5, 6, 7, i.e. mask indices are in continuous succession in the set selected and slid around under control 95.

For two C-scans, embodiments may use only mask index q=3 and q'=7, for two distanced targeted layers in the object, i.e. not necessarily next to each other within the set of N mask indices.

When performing a C-scan, a single MS-calculator 41(q) is used. When performing a B-scan, Q MS-calculators 41(p), 41(p+1), ... 41(p+Q) are used, where mask index p determines a reference depth wherefrom the tracking axial range starts.

The four embodiments in FIGS. 6a, 6b, 6c and 6d of the MS-processor are enabled in synchronism with the lateral scanning, trigger 112 delivered by the switch mode 113, sequentially or in parallel with the operation of other blocks, such as the sensor 8, corrector 9 or storing processes of signals as further disclosed below, depending on the speed of acquisition and resources available in terms of separate assembled blocks, FPGAs or GPUs, engaged sequentially or in parallel.

Flattening

To perform flattening, the embodiment in FIG. 6 is used as disclosed below. In a first lateral scan, curvature of object is sensed and using such information, an array of correction for mask indices i are prepared to be employed by the corrector 9 during a subsequent scan, to flatten the image.

Schematic diagrams of the sensor 8 (left) and MS-processor 6 (right) are presented in FIG. 7a, FIG. 7b and FIG. 7c. In these embodiments the sensor 8 employs the electrical signal 20 due to the channeled spectrum delivered by the same imaging interferometer employed to deliver the OCT image. The sensor 8 in these figures aims to detect the axial position of each lateral pixel of the object 3, addressed by lateral scanning.

The sensor in FIGS. 7a and 7bs employs a MS algorithm whilst that in FIG. 7c, a FFT.

Variations of signals 40 over depth in FIGS. 7a and 7c and variations of signal 40 over lateral coordinate in FIG. 7b are compared in a block Thresholder, 82, to threshold levels set by a Conditioner 81.

Performing segmentation via the MS protocol is possible via two possible scenarios.

(i) As shown in FIG. 7a, using all Q masks for each event r, of channeled spectrum scan (or read) In performing segmentation via the MS protocol as shown in the left of FIG. 7a, for each r, controlled by 23, Q masks are subject to the MS algorithm in parallel, with each channeled spectrum 20 at that r, in Q MS-calculators 41 to produce an equivalent A-scan and then using the threshold 82 retain the mask index in 83 where the peak is registered. This requires comparing the levels for each depth, q. Such a procedure retains the mask index $q_r$ where the peak is, when:

Modulus difference of {[modulus of complex signal $40(q_r)$]-[modulus of complex signal $40(q_r-1)$]}>Threshold (1)

Each spectral scan controlled by 23 ends for each r with the index $q_r$ of the mask where the change in amplitude from mask q-1 to mask q exceeded the threshold established for that r, $81_r$. Retention of mask index is shown in FIG. 7a'.

Let us suppose that the object is a metal sphere, i.e. a single surface object, as shown by the contour 3 (3') in FIG. 7a'. In this case, there is a single peak in the A-scan. At each lateral pixel, the thresholder 82 will return the index of the mask that corresponds to the mask that delivered a variation signal over the depth, larger than the threshold, for that r lateral pixel. The threshold levels $81_r$ can all be the same or using prior knowledge of levels, these are set accordingly, via line 86. The sphere contour extends in depths over an axial range Qδ, from an initial depth corresponding to mask index p to a maximum depth given by mask index p+Q, where δ is the axial resolution interval. For each spectral scan event, r, trigger 23, an array 83 of mask indices is produced. For each r, the array 83 of Q elements contains a single index $q_r$ different from zero with all others set to zero. If the threshold is set right, a single element of the array 83r is different from zero and all others are set to zero. This is shown in FIG. 7a' by values $83_r$ given by $q_r$=p+1, p+2, p+s, p+Q, p+s, p+2, p+1 for respective lateral pixels r=1, 2, ... r, ... r', ... r", ... R-1 and R. The set of such indices for all spectral readings within the lateral scan, for each lateral pixel, r, associated to each spectral scan, trigger 23, represent the segmentation of the object shape in the OCT cross section. In this way, a contour of mask indices, $q_r$, is generated by the MS algorithm using the sensor in FIG. 7a. If the channeled spectrum is delivered nonlinearly along the wavenumber, the FT based method demands resampling that takes time. Using the MS protocol, a simpler operation is performed. As shown in FIG. 7a', the masks indices $q_r$ are then used by the corrector 9 to create an index variation i in respect to a reference index, in the memory 94, selected as $q_1$ in FIG. 7a'. The index variation i is suitably used via control input 95 to shift the Q masks in the Mask selector 5, within the range of masks N, to flatten the top of the B-scan, i.e. to produce the output signal at the sensor output to the corrector 9. The index variation i can also be used to shuffle, dynamically alter, the mask index used delivered by Mask selector at each spectral scan, r, when producing a single C-scan image.

(ii) As shown in FIG. 7b, another possibility consists in using a set of R stored channeled spectra 20 for each mask: In a first lateral scan interval $T_x/2$ of the fast scanner 110, R channeled spectra are stored in memory 99 to be later used for segmentation, transferred to storage 99' and to storage 99" for correction. During the next lateral scan, all R channeled spectra stored are distributed to a Dynamic MS comparator 4", where R channeled spectra are processed based on the MS algorithm with a single mask 50(q) at a time, from the Mask selector 5". What is now retained for each mask 50(q), is the lateral pixel r when:

Modulus difference of {[modulus of complex signal $40_r(q)$]-[modulus of complex signal $40_{r-1}(q)$]}>Threshold (2)

The process is repeated for all Q masks under control repetition trigger 23". As each time the mask index delivered by 5" is known, in this scenario is not the depth (mask index thought after) but the pixel index r. This is equivalent on placing a T-scan along the contour of a curved single layer object 3 as shown in FIG. 7b', where a T-scan is advanced in depth for each q, and collecting the pixel r where equation (2) is accomplished. In this case, the peak is associated to the lateral pixel r where the modulus change in amplitude from pixel r−1 to pixel r exceeds the threshold in thresholder 82. Along the same T-scan, another change may be detected at another pixel r', where the modulus of change of MS calculated strength between pixel r'−1 to pixel r' exceeded the threshold. In this way, at the two lateral pixels, a change in strength is recorded over the threshold and mask index of the 50($q$) is q, known and r' is also retained. An interesting modality to speed up the sensing is that, based on a prior knowledge of the object, such as its contour being contiguous, once the top layer is intercepted, less MS calculations are needed. Let us refer to the T-scan immediately below the T-scan 50(p+Q), in FIG. 7b', here inside the object no calculation should be done for the pixel r', i.e. MS calculation should use R−1 stored channeled spectra. Progressing more in depth, using mask 50(p+s), a whole range of channeled spectra can be excluded from the MS calculations, for the range between pixels r and r" and so on.

As shown in FIG. 7b', the masks indices $q_r$ are then used by the corrector 9 to create an index variation i in respect to a reference index, in the memory 94, selected as $q_1$ in FIG. 7b'.

FIG. 7c shows in diagrammatic form, another embodiment of the sensor 8. In cases where a large number of sampling points, M, is employed, then the FFT is faster than the MS, as long as no resampling of data is performed. To perform fast, FFT operations are performed using uncorrected, not resampled data. For this operation, let us say that the FFT can extend up to N=M/2 depth range values and the tracked axial range corresponds to Q such values. In this case, changes are thought along the depth coordinate in the A-scan amplitude. A FFT processor 6" processes the channeled spectrum 20 and produces A-scans, as shown in FIG. 7c', that are sent to the thresholder 82. In this case, amplitudes 40($q$) represents A-scan strength. For each spectral scan trigger 23, i.e. for each r, when:

Modulus difference of [Modulus of $A$-scan at depth ($z_r$+δ)−Modulus of $A$-scan at depth $z_r$]>Threshold (3)

the depth $z_r$ of the A-scan peak is retained. In this case, what is retained after thresholding is the distance $z_r$, of the A-scan peak position, considering that by adjusting the threshold value, each A-scan reduces to a single peak. What is now input to the array 83' are not the mask indices such as in 83, but the depth position, $z_r$, where the strength of A-scan variation from a depth slot to the next exhibited the peak. As shown in FIG. 7c', the distances retained are d+δ, d+2δ, d+sδ, d+Qδ, d+sδ, d+2δ and d+δ for respective position of the pixels 1, 2, r, r', r", R−1 and R. Let us consider the initial distance where tracking starts, d=δp, where p is the mask index corresponding to d. Intersection of the contour 3 (3') with peaks of A-scans at distances $z_1=z_R=\delta$ (p+1), $z_2=z_{R-1}=\delta$(p+2), $z_r=z_{r'}=\delta$(p+s), $z_r=\delta$(p+Q) are shown, where δ is the axial resolution interval. The corrector 9 operates by establishing a reference value, in the example shown in FIG. 7c', set at the beginning of the lateral scan, at r=1, where distance is d, in which case differences $z_r-z_{REF}$ are placed for each r in the R locations of the storage 94'. When divided by δ equivalent mask indices are obtained, as shown in FIG. 7c'.

For better clarity in the different modes of operation of sensors in FIGS. 7a, 7b and 7c, the array 83 of mask indices and of distances 83' produced have dimensions (Q,R), of Q lines and R columns. For FIGS. 7a and 7b, the elements $83_r(q)$ are shown in the matrix (4), where the embodiment in FIG. 7a populates the columns of the matrix 83 for each event r, i.e. for each spectral scan 23, while the embodiment in FIG. 7b populates the matrix 83 for each depth q, line by line.

$$\begin{bmatrix} 83_1(p+1) & 83_2(p+1) & \cdots 83_r(p+1)\ldots & 83_R(p+1) \\ 83_1(p+1) & 83_2(p+2) & \cdots 83_r(p+2)\ldots & 83_R(p+2) \\ \cdots & & \cdots & \cdots \\ 83_1(p+1) & 83_2(p+q) & \cdots 83_r(p+q)\ldots & 83_R(p+q) \\ \cdots & & \cdots & \cdots \\ 83_1(p+Q) & 83_2(p+Q) & \cdots 83_r(p+Q)\ldots & 83_R(p+Q) \end{bmatrix} \quad (4)$$

Am equivalent matrix can be written for 83', by multiplying the matrix in (4) by δ. Similar to the embodiment in FIG. 7a, the embodiment in FIG. 7c populates the equivalent matrix 83' for each event r, i.e. for each spectral scan 23, column by column. For R events, MS is employed in the embodiment in FIG. 7a whilst FFT is employed in the embodiment in FIG. 7c.

In FIG. 7b, the matrix 83 is populated line by line by a Mask selector 5", that via 23" demands Q repetitions of calculations in the compound comparator 4" of MS reflectivity values for all R channeled spectra stored in 99' each time with another mask 50($q$), for Q repetitions.

For flattening of a T-scan, the embodiments in FIGS. 7a, 7b and 7c are used for R=H spectral scan events, i.e. for the total number of lateral pixels in the one dimensional lateral scan. For flattening of C-scans, the embodiments in FIG. 7a, 7b, 7c can also be used for R=HV spectral scan events, 23, i.e. for the total number of lateral pixels in the bidimensional lateral scan.

The arrays 83 are sent via 84 to the corrector 9, that in its storage 94 will contain the mask indices, values from p+1 to p+Q as well as difference of indices, starting from a reference value, such as $83_r-83_{REF}=q_r-q_{REF}$. For reference taken from the first pixel, r=1, $q_{REF}=q_1$, in which case $q_r-q_1$ are stored. Reference can also be taken not from the first pixel but from the pixel in the middle of the T-scan line, or in the middle of the C-scan, at R/2 (in which case the storage 94 stores $q_r-q_{R/2}$ values) as well or from the pixel where maximum or minimum mask index was retained.

To generate a single C-scan, the MS-processor 6 in the right-hand side of FIGS. 7a, 7b and 7c uses a single MS-calculator in the Dynamic MS comparator, as illustrated in FIGS. 6a and 6c. If B-scan images are generated, then the MS-processor 6 engages a Dynamic MS comparator 4 with Q MS-calculators, such as in FIG. 6b or 6d, hence the two output possibilities shown out of the Dynamic MS comparator 4 in FIG. 7a, 7b, 7c.

The differences i, from a reference index, either first index or that in the middle of T-scan or in the middle of the C-scan, depending the case, are used for the correction function, delivered by 9, to dynamically change the mask used for MS operation for each lateral pixel r, by the Mask selector 5.

To allow for timely correction of the acquired set of electrical signals corresponding to the channeled spectra, they are stored in the storage 99 and are transferred to be used with the required delay in memory 99", synchronized by trigger 112.

In the corrector 9, irrespective of the segmentation (edge detection) method used for sensing, using MS of FFT, the output, i, shown in FIG. 7a', FIG. 7b' and FIG. 7c' is similar. Storage 94 and respectively 94', stores differences of numbers that are similar. Storage 94 in FIGS. 7a and 7b stores differences of mask indices while storage 94' in FIG. 7c stores differences of depth slots. By dividing them by δ, a similar number, i, is obtained at the corrector output 9. The masks are separated in their OPD (depth), by an axial resolution element 6, the same as in the FFT.

At the bottom of each FIG. 7a, 7b, 7c, possible scenarios of sequential regimes of operation are shown, controlled by 112 in synchronism with the lateral scanning. The duration and parallelism of possible regimes depend on the time taken by each process of sensing and correction for achieving flatness.

Let us consider H=V=200 pixels along horizontal and vertical directions. Using a swept source at 100 kHz, for H=200, a lateral scan of R=200 pixels lasts 2 ms, this represents the duration of one ramp signal applied to the fast lateral scanner 110. Two ramps would mean a triangular shape of the signal applied to 110 of period $T_X$=4 ms. (For resonant scanners, due to their sinusoidal displacement, elimination of fly-backs requires $T_X$ slightly longer).

In some cases, as shown in FIGS. 7a and 7c, two lateral scans, each of $T_X/2$ of the fast scanner 110, for sensing the curvature followed by its correction are sufficient, in some other cases, as illustrated in FIG. 7b, 3 such intervals are used, where the $1^{st}$ interval is allocated to acquisition and storage of channeled spectra, $2^{nd}$ interval to edge detection of axial position for each pixel r, followed by correction and flattening on the $3^{rd}$ interval. The scenario shown at the bottom of FIG. 7b is also more suitable for fast lateral scanning, when $T_X$ is shorter than the duration required for the different operational modes. Practical implementation, depending on digital resources, may demand separation of acquisition from any action, that may demand an extra lateral scanning interval.

The intervals shown at the bottom of FIGS. 7b, 7b and 7c could also refer to periods of a saw-tooth signal applied to the fast lateral scanner 110, in which case, with the numerical examples above, $T_X$=2 ms and period measured from one pulse 112 to the next. In this case, at the bottom of FIG. 7b, the 3 cycles of 112 pulses last for 6 ms, for 3 periods $T_X$.

In case of acquisitions of stationary curved objects, the data does not vary in time, so in this case there is no need for memory 99" to store the channeled spectra. In such cases, correction can be applied to a new set of channeled spectra acquired. Otherwise, if object is subject to movement, the R channeled spectra 20 are stored for one or more sub-periods or periods of the fast lateral scanner 110. In this way, corrected, flattened T-scans are delivered with delays of a few milliseconds only. Considering the embodiment in FIG. 7a for instance, operating in two stages, for a square image of 200 pixels along X and Y, for a triangular signal of period Tx=4 ms applied to the fast lateral scanner 110, a full en-face image is obtained in 0.8 s with a delay of only $T_X$=4 ms, i.e. quasi-real time. Using a saw-tooth signal of Tx=2 ms, a full en-face image is obtained in 0.4 s with a similar delay of only 4 ms.

Overall operation can be made faster using parallel processing, by engaging parallel processing, using multiple CPUS, GPUs or FPGAS. By storing R channeled spectra, Q MS-calculators 41 can be engaged in R batches to operate in parallel in the sensor 8 in FIG. 7a in the time needed for Q MS calculations for a single pixel r. Similarly, R MS-calculators 41 can be engaged in Q batches to operate in parallel in FIG. 7b in the time needed for R MS calculations for a single depth index q. Also, R FFT processors 6" can be engaged to operate in parallel in FIG. 12c in the time for a single apodization and a single FFT required for segmentation by the sensor 8.

For simplicity, the sketches in FIGS. 7a', 7b' and 7c' above are based on a single layer object.

In case of tissue, such as cornea, retina, there is more than a single peak in the A-scan. Targeting to edge detect the interface between the retina and vitreous, the inner limiting membrane exhibits a small reflectivity and therefore the threshold in 82 is set low. Targeting to edge detect the RPE that is more reflective, the threshold is set higher. If the object imaged 3 is cornea, that is curved and returns a lot in its center and less from edges, some knowledge of the lateral variation of the signal amplitude is needed to set the values of thresholds along the lateral coordinate, X and r, via line 86.

Figure 8A:
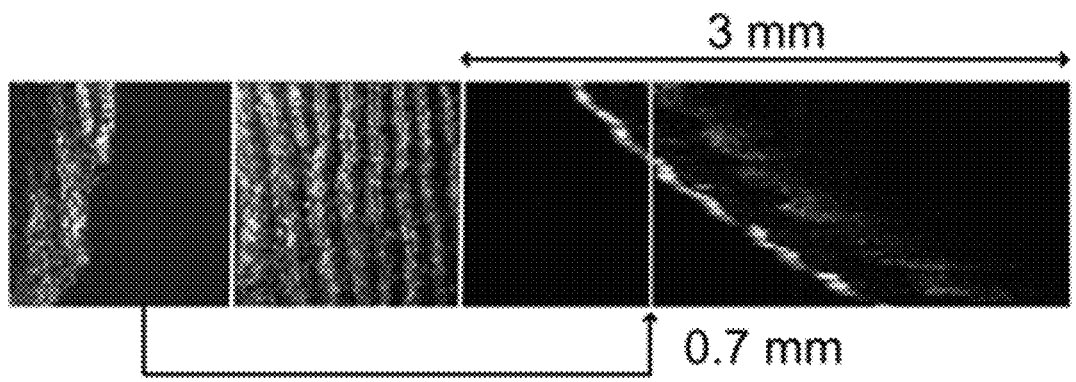
FIG. 8a illustrates en-face OCT images from finger skin using the imaging interferometer for both sensing and imaging.
Figure 8B:
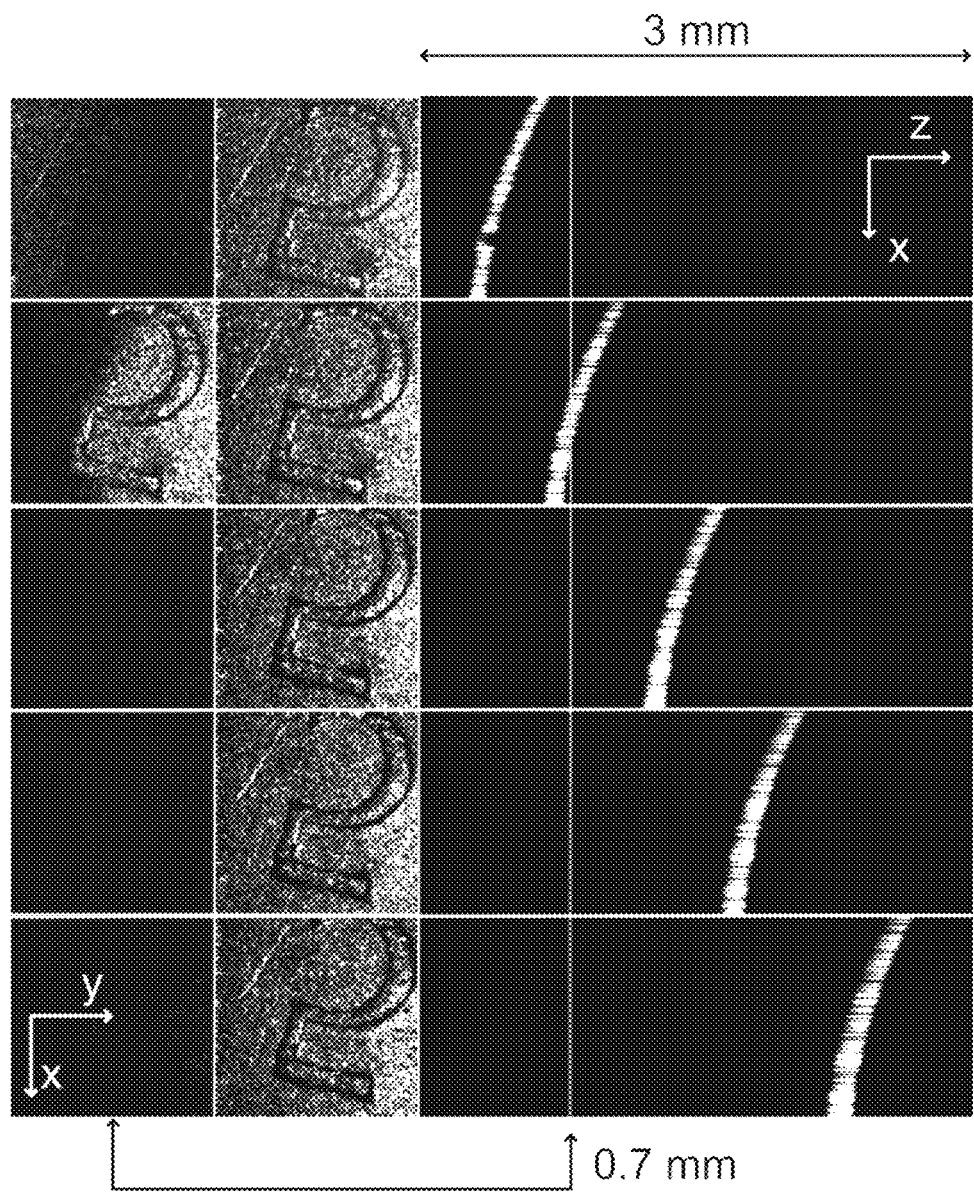
FIG. 8b illustrates images from a tilted coin using the imaging interferometer for both sensing and imaging.
Figure 8C:
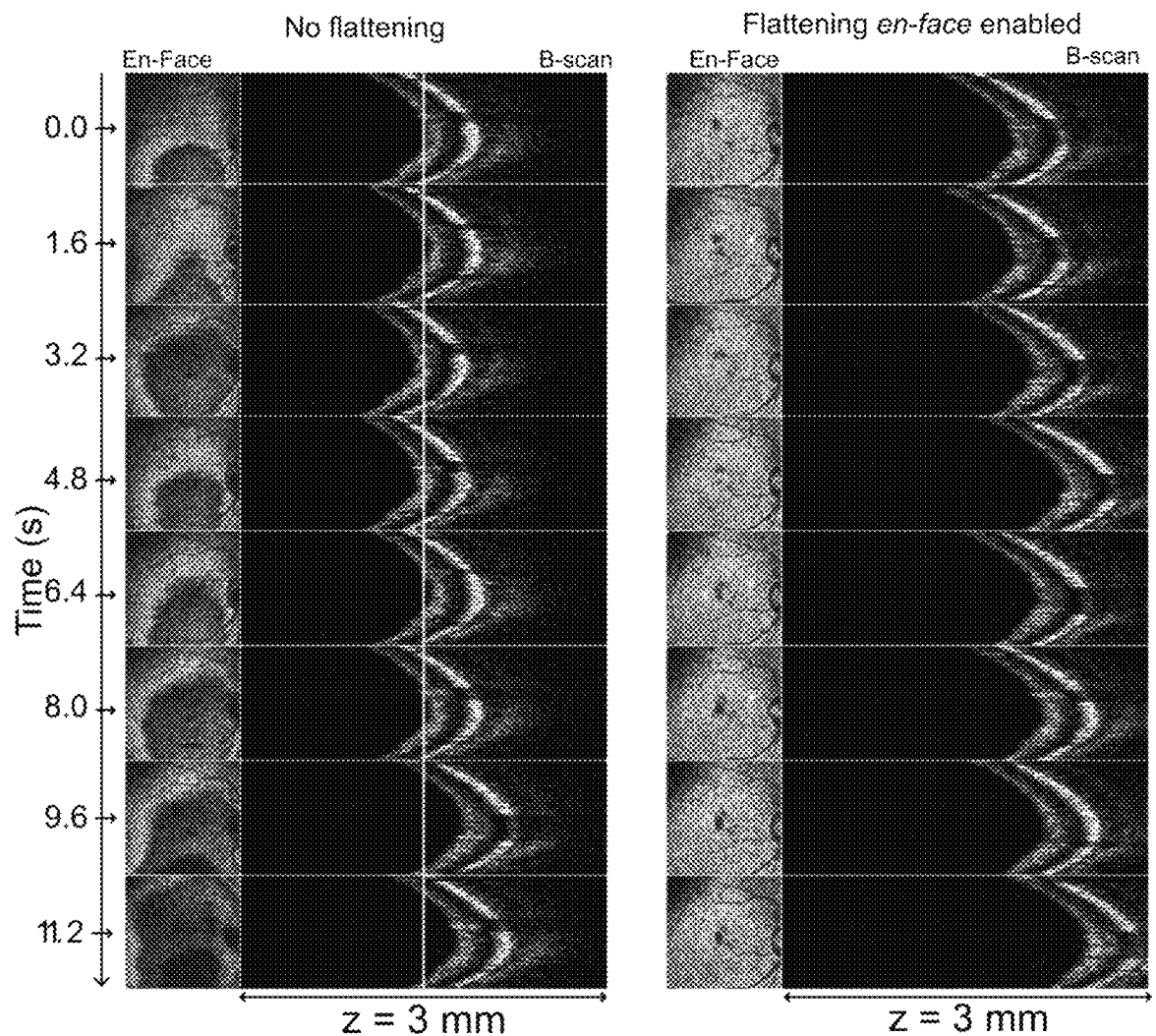
FIG. 8c illustrates images from the retina of a volunteer using the imaging interferometer for both sensing and imaging.

Results obtained with a proof of concept system are presented in FIGS. 8a, 8b and 8c. They illustrate flattened images obtained from several objects. These were obtained by engaging a system assembled based on the embodiment in FIG. 7c, with a triangular signal applied to the fast lateral scanner of Tx=4 ms and where the MS-processor 6 employs an embodiment such as in FIG. 6a, with a single MS-calculator used sequentially for R=200 lateral pixels along the T-scan, to deliver a single flattened en-face OCT image made from 200×200 pixels (i.e. image created from one ramp of the triangular signal only).

FIG. 8a shows images from finger skin. The left and middle image are C-scans, the image on the right is the B-scan image. Because the tissue is tilted, as shown in the B-scan image on the right, and also due to finger curvature, the en-face image on the left is fragmented and displays a small area, intersecting air and several layers in depth in the object 3, the finger. The vertical line shows where the image on the left is selected from. Enabling the flattening, the C-scan image in the middle is produced, using as target layer from the object, the top layer of the skin. The display is quasi real time, where each T-scan in the en-face image is delayed by a period, Tx=4 ms.

FIG. 8b illustrates quasi real time axial tracking and tilting for a single layer object, a coin. The third column shows B-scans from the coin displaced axially. The depth where the C-scan images are collected from in the first column is given by the vertical line. In the top row, the coin is above the depth where the C-scan image is collected from. In the second row, the coin was pushed to a depth where it intersects the vertical line. Because the coin is tilted, the C-scan image is fragmented showing pixels within its area from air as well as pixels from the coin, i.e. from different OPDs. In the second column, the flattened en-face images are shown. Tilt is eliminated, as well as the axial distance tracked. Even if the coin is displaced axially in depth in the $3^{rd}$, $4^{th}$ and $5^{th}$ row, the apparatus continues to displays the en-face OCT image of the coin, flattened (eliminating the coin tilt), irrespective of its depth position (axial tracking proven).

FIG. 8c show images collected from the retina of a subject. The images on the left show C-scan images collected from the eye with the feedback loop open, i.e. correction and flattening disabled. FIG. 8c on the right show C-scan flattened OCT images obtained with the feedback loop closed. While images acquired with the feedback loop open show both curvature of the retina as well as time variation of the axial position of the retina, the images obtained with the feedback loop closed deliver corrected images for both curvature and axial position. These not only show larger contiguous areas in the en-face section, due to flattening, but stability to axial fluctuation of the eye along the depth axis. Sequences are shown at every $2^{nd}$ acquisition collection, i.e. at 1.6 s, to allow accumulation of larger disturbances than in $t_F$=0.8 s.

For the computer used to produce the images in FIG. 8a, b, c, an Axsun swept source at 100 kHz, 1060 nm, images of H=V=200 pixels, and a 12 core CPU PC were used.

For the segmentation (edge detection) operation based on A-scans obtained by FFT (i.e. using FIG. 7c with the MS-processor 6 from FIG. 6a), for M=1024, N=512 distinct depth slots and R=200, apodizations and FFTs repeated for R=200 times takes 1.2 ms, i.e. less than 2 ms=R×sweeping period $t_r$ of 0.01 ms. A single apodization and FFT takes 0.1 ms, however when performing 200 of them, due to parallel processing on the 12 core PC, time taken was 1.2 ms only, much less than 200×0.1 ms=20 ms.

These examples of times are important in establishing engagement of parallel resources. The disclosure refers to such option for the developer to engage MS or FFT in the sensor depending on the object imaged and digital resources available, while at the correcting stage, MS in the final imaging procedure employs dynamic allocation of masks.

If the layer in question has weak contrast and an automated segmentation fails, embodiments described herein protect the solution where it is possible to also accept manual segmentation. An user can manually introduce a manual contour approximating a layer selected on the image via input 87. No thresholder 82 is used in this case in FIG. 7a, 7b or 7c. Instead, the mask indices generated by the manual contour are used. In addition, such a contour may be comprised of fewer points than those in the lateral scan, i.e. less than R, therefore, a linear or spline interpolation (or other similar method) can be used in between points, so that the array 83 in FIG. 7a, FIG. 7b or 83' in FIG. 7c still possesses R elements.

Figure 9:
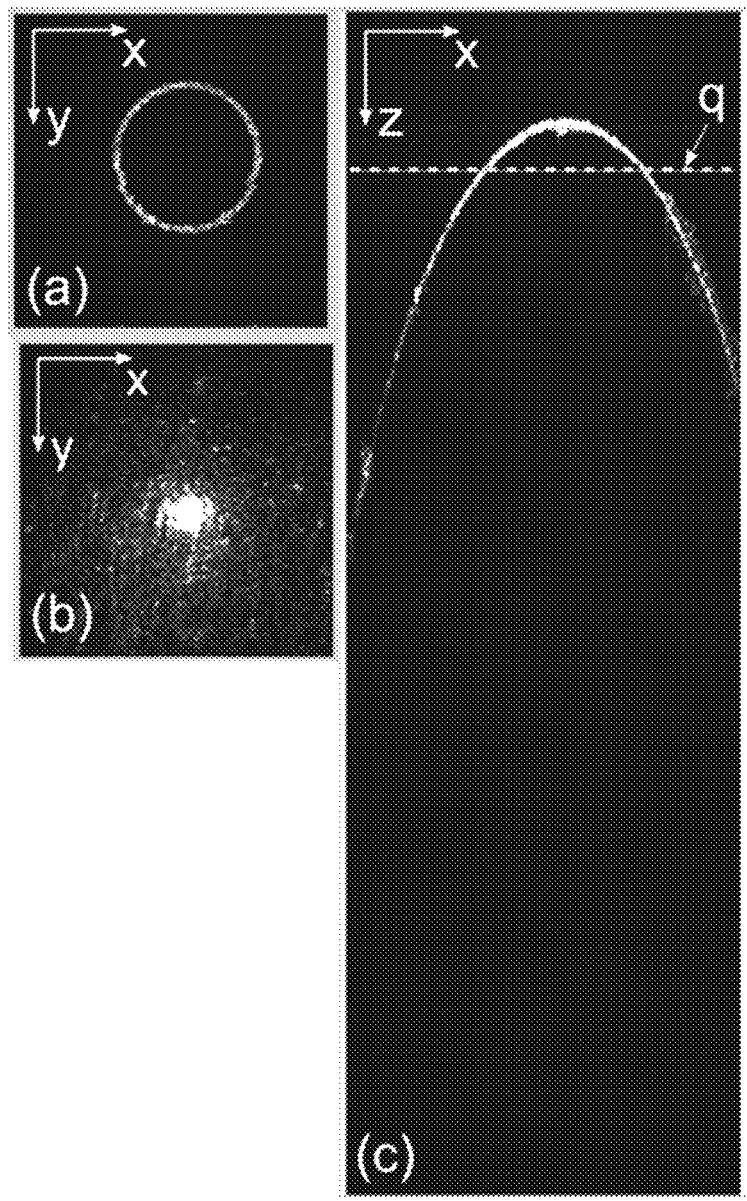
FIG. 9 shows images of a sphere prior to obtaining flattened images in FIG. 10.

Preliminary results using manual input 86 are presented for a metallic sphere as object 3. In FIG. 9, conventional visualizations of both B-scan and C-scan images are presented, (a) displays the signal 40(q) leading to a C-scan taken along a single depth q, which is represented as a line overlay at depth q in the B-scan display (c). This cuts through the surface of the spherical metal object, yielding a circle in the C-scan representation 40(q) in (a). The confocal representation in (b) is a summation of C-scans from all depths, therefore the top of the sphere is fully visible.

Figure 10:
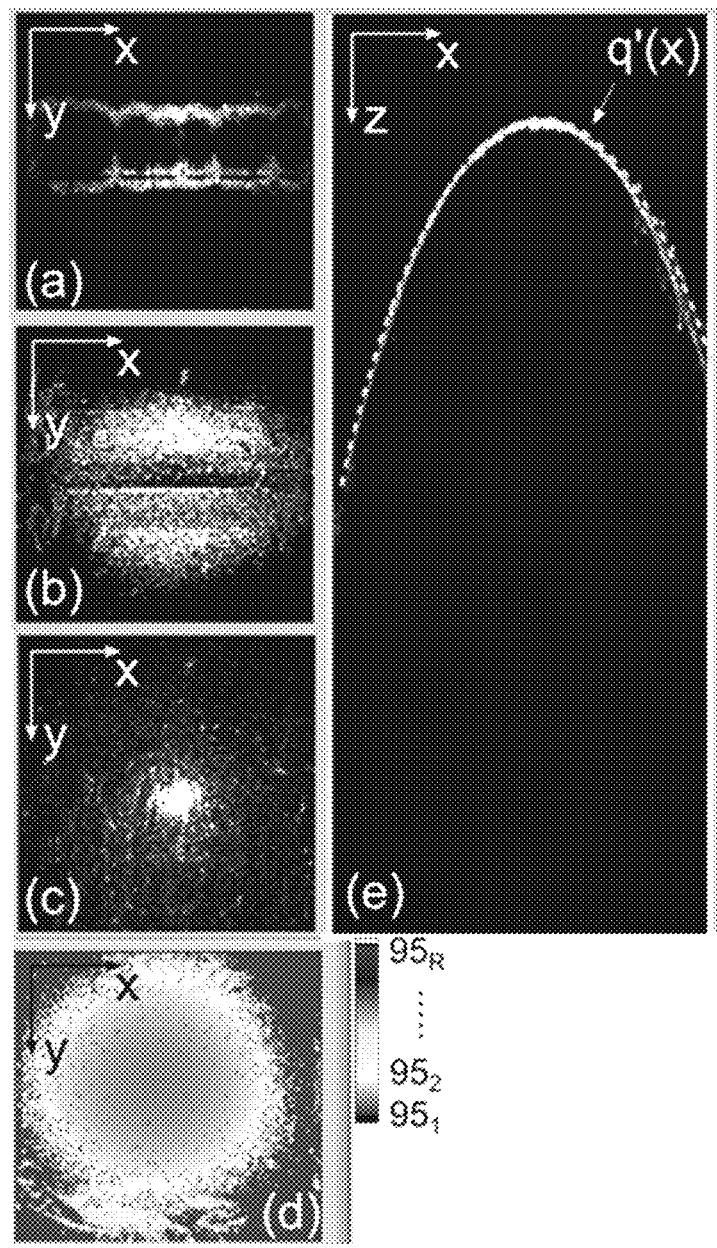
FIG. 10 shows images of a sphere using two flattening procedures.

In FIG. 10(e), a manually drawn region of interest q'(x), with x along the lateral coordinate, x, is drawn over the pixels r=1, 2, . . . R. This is overlaid on the B-scan image of the sphere, which dictates the selection of masks $83_r$ from storage 83 (in any of FIG. 7a, 7b, 7c) for each lateral position x=r, at a fixed y at which the B-scan image was produced. The data from the manually drawn contour is input via line 87. A C-scan constructed by employing such mask subset is shown in (a). Since the sample presents curvature on both x and y directions, the image is only flattened along the mid-section of the frame, effectively only flattened along the x direction.

In FIG. 10(b), a fully flattened image is presented, employing the sequential procedure described previously, and already proven by images in FIG. 8. In this case, 200×200 A-scans were obtained using MS in FIG. 7a and Q=600 masks, during an initial stage, where a complete frame was acquired. Then, at a second stage, Sensing, the surface of the object is sensed, by use of a thresholding algorithm of edge filtering applied to the whole volume of A-scans over 3 mm as explained in FIG. 7a'. Using a matrix 83 (FIG. 7a) for all R scans, where R=40,000, corrections were created as a function of both x and y and after they have been applied, color-coded heat map in (d) was obtained. The set of corrections is then used at the next step, Flattening, to render a fully flattened en-face OCT image, as shown in (b).

In comparison with FIG. 8 however, here, because the object is stationary, stages of operation were applied after a complete frame was obtained, close to a second and not "on the fly", as in FIGS. 8a, 8b and 8c.

Axial Tracking Using a Second Interferometer

FIG. 11 discloses in diagrammatic form, a second embodiment of an imaging OCT apparatus, that further comprises a second interferometer. Here the sensor 8S is disconnected from the imaging interferometer and connected to the second interferometer. The sensor 8S is fed by the electrical counterpart 20S of the optical channeled spectrum 10'S from the decoder 2S of the second interferometer. The embodiment of the apparatus in FIG. 11 performs axial tracking and is favored when the reflectivity from any object layer may not be sufficiently strong to be reliably used by any sensing method. A typical example is the retina, that has superficial layers of low reflectivity followed by a highly reflective layer, the RPE, that can induce errors in the chosen targeted layer. Better for edge detection would be to use cornea 3', that can secure a stronger reflectivity signal. The apparatus can be made more tolerant to axial movements of the object, 3 (3'), based on a stronger signal to be used by the sensor. Similar to the embodiment in FIG. 6, the imaging system consists in a decoder 2I, incorporating a source 21I and a reader 22I, where the imaging interferometer consists in a beam-splitter 12I, the lateral scanner 11, shared splitter 12C, reference mirror 13I and object 3, a MS-processor 6I, in the spirit of the embodiments described herein, as disclosed in any of FIG. 6a, FIG. 6b, FIG. 6c or FIG. 6d. The apparatus could also incorporate a memory 99I or more, for the channeled spectra as presented in conjunction with embodiments in FIGS. 7a, 7b and 7c.

The second interferometer consists in a splitter 12S, reference mirror 13S shared beamsplitter 12c and part of the object 3'. Supplementarily, the apparatus also consists in a decoder 2S that incorporates a source 21S and a reader 22S. The second interferometer collects signal from the top of the organ in surgery, or when imaging the anterior chamber in an eye, from cornea, where in both examples 3 and 3' coincide. When imaging the retina 3 of an eye, light in the second interferometer is collected from the cornea 3', as shown in FIG. 11. It is also possible in surgery for instance that the two portions of the object, 3 and 3' are different. In this case, the shared splitter 12C becomes un-necessary.

When imaging the retina 3 and using cornea as 3' for sensing, the interface optics to collect optical signal from either cornea or retina is not shown, but utilization of focusing elements to either cornea or retina is obvious for the person skilled in the art as disclosed in U.S. Pat. No. 8,678,594 "Apparatus and method of monitoring and measurement using spectral low coherence interferometry", by A. Gh. Podoleanu and M. Leitner. The two decoders 2I and 2S preferentially should employ optical sources 21I and 21S of different wavelengths in order to enable a dichroic filter as the shared beamsplitter 12c, in this way reducing the losses at both wavelengths.

The sensor 8S outputs data on the axial position of the part of the object 3', along line 84S to a corrector 9. This information can be obtained based on the MS principle as disclosed in FIG. 12a and FIG. 12b, where differences of indices of masks are stored for each event, e=1, 2 . . . E, in the Storage 94 of the corrector 9. Distance information can also be obtained using the embodiment in FIG. 12c where the sensor 8S employs FFT and A-scans, in which case 94'S stores distance information from a reference depth.

This axial information can be used post acquisition, as well as in real time, or quasi real-time, as explained more below.

Sensing the Axial Position of the Object Along a Stationary Beam and Correcting for Axial Distance the Images Generated Schematic diagrams of the sensor 8S (left) and MS-processor 6I (right) used in the embodiment in FIG. 11 are presented in FIG. 12a, FIG. 12b and FIG. 12c. The sensors 8S in FIGS. 12a and 12b employ the MS protocol, and are similar respectively to the sensor embodiments in FIGS. 7a and 7b. The sensor 8S in FIG. 12c employs FFT, and is similar to the sensor embodiment in FIG. 7c. The operation of these sensors is detailed in respective FIGS. 12a', 12b' and 12c'.

The main differences in the FIGS. 12a, 12a', 12b, 12b', 12c and 12c' in comparison to the respective FIGS. 7a, 7a', 7b, 7b', 7c and 7c' are the facts that: (i) The optical beam of the sensor 8S targets a single pixel of the object 3(3') and that (ii) the sensor 8S can operate at rates 23S, $1/t_e$, faster than the rate of imaging scans 23I, $1/t_r$. Event e represents the spectral scan of the decoder 2S initiated via control line 23S. Events r in FIGS. 7a, 7a', 7b, 7b', 7c and 7c' are replaced by temporal events, e in FIGS. 12a, 12a', 12b, 12b', 12c and 12c'. In these figures, e=1, 2, . . . E represent spectral scan events in the sensor 8S, at time intervals of period $t_e$. The different repetition sequences of 23I and 23S are shown at the bottom of FIGS. 12a, 12b and 12c.

It is now possible to have several sensing events e, along line 23S from decoder 2S, per each spectral scan, r, event synchronized along line 23I by decoder 2I. For example, the imaging can use a swept source 211I at 1060 nm for retina at 100 kHz sweeping rate, $t_r$=10 microseconds and the sensor 8S to employ a swept source 211S at 1300 nm at 1 MHz, $t_e$=1 microsecond, in which case sensing is updated 10 times for each lateral pixel, r. In this way, 10 axial distance values are measured per each imaging spectral scan, r, that can allow obtaining an average distance position to be used for the i-correction delivered via 84 to corrector 9. In case there are variations in the axial distance during the imaging spectral scan, i.e. if the 10 measurements differ considerably, that scan r is discarded and another set of sensing scans (in this example 10) for the same r can be repeated. Sensing acquisition events, e, are synchronized by trigger 23S, but sensing information can only be accepted by 5I at the rate imprinted by trigger 23I.

Sensing the axial position of the object 3(3') using FIG. 12a is based on:

Modulus difference of {[modulus of complex signal $40(q_e)$]−[modulus of complex signal $40(q_e−1)$]}>Threshold (5)

For each sensor spectral scan event e, a single index, $q_e$, in the array $83_e$ of Q elements is different from zero, that is retained.

As shown in FIG. 12a, at the 1$^{st}$ stage, Sensing (edge detection), for a number of R pixels, R channeled spectra are acquired and stored in memory 99I to be used later at the correction stage. At the 2$^{nd}$ stage, mask indices are sent by the corrector 9 to the Mask selector 5I, to be used by the Dynamic MS comparator 4 to produce axially corrected reflectivity values.

For each spectral scan event, e, trigger 23S, an array 83 of mask indices is produced. For each e, the array 83 of Q elements contains a single index $q_e$ different from zero with all others set to zero. If the threshold is set right, a single element of the array 83e is different from zero and all others are set to zero. This is shown in FIG. 12a' by values $83_e$ given by $q_e$=p+1, p+2, p+s, p+Q, p+s, p+2, p+1 for respective events e=1, 2, . . . e, e', e'', . . . E−1 and E. The set of such indices for all spectral readings within the sequence of E scans, trigger 23S, represents the edge detection of the axial position of the object. In this way, a set mask indices, $q_e$, is generated by the MS algorithm using the sensor in FIG. 12a.

Sensing the axial position of the object 3(3') using FIG. 12b requires, like in FIG. 7b, to store the channeled spectra, in this embodiment for E events in a separate memory, 99S. Channeled spectra from the imaging interferometer are also stored in 99I to be used during correction, using storage 99'''I. The edge detection is based on:

Modulus difference of {[modulus of complex signal $40_e(q)$]−[modulus of complex signal $40_{e−1}(q)$]}>Threshold (6)

What is now retained when equation (6) is accomplished is the index of the event e, for each mask $50(q)$, as the mask index q now is known, as a difference to the procedure in FIG. 12a.

The process is repeated for all Q masks under control repetition trigger 23''. As each time the mask index of the mask delivered by 5'' is known, in this scenario is not the depth (mask index thought after) but the index of the event, e. This is equivalent on placing a T-scan above the contour of the axial variation in time of the object, in FIG. 12b', where a T-scan is advanced in depth for each q, and collecting the index e where equation (6) is accomplished. In this case, the peak is associated to e, where the modulus change in amplitude from event e−1 to event e, exceeds the threshold in thresholder 82. Along the same T-scan, another change may be detected at another event, e', where the modulus of change of MS calculated strength between e'−1 to e' exceeded the threshold, and e' is also retained. In this way, the mask index of the $50(q)$, q, that is known, is associated to the two events.

Sensing the axial position of the object 3(3') using FIG. 12c is based on:

Modulus difference of [Modulus of A-scan at depth $d+\delta$)−Modulus of A-scan at depth $d$]>Threshold (7).

In this case, what is retained after thresholding is the distance from a start depth of the A-scan peak position, considering that by adjusting the threshold value, each A-scan reduces to a single peak. What is now placed in 83' are not the mask indices such as in 83, but the depth position, $z_e$, where the strength of A-scan variation from a depth slot to the next exhibited the peak. A FFT processor 6'' processes the channeled spectrum 20S and produces A-scans that are sent to the thresholder 82. As in FIG. 7b, data is not resampled, to enable fast edge detection. In this case, fast production of approximate amplitudes $40(q)$ are employed to deliver the amplitudes $40(q)$ to the thresholder 82 for each spectral scan trigger 23S, i.e. for each temporal event e. For the case illustrated in FIG. 12c, the distances retained in FIG. 12c' are d+δ, d+2δ, d+sδ, d+Qδ, d+sδ, d+2δ and d+δ for respective sensor scan events 1, 2, e, e', e'', E−1 and E. Intersection of the axial edges of the object 3 (3') with peaks of A-scans at distances $z_1$=δp, $z_2$=$z_{E−1}$=δ(p+1), $z_e$=$z_{e''}$=δ(p+e), $z_e$=δ(p+Q) are shown, where δ is the axial resolution interval.

For all embodiments in FIGS. 12a, 12b and 12c, a similar matrix 83 to the matrix of mask indices in (4), but of size (Q, E), can be written by replacing the subscripts r=1, 2, . . . r, . . . R with respective subscripts e=1, 2 . . . E. The procedures of edge detection in FIGS. 12a and 12c populate columns of such matrix while the procedure implemented in FIG. 12b populates the rows of the matrix.

The sensor 8S sends data on the axial position of the object 3(3'), along line command 84 that controls the operation of the MS processor 6I. The Mask selector 5 in the MS-processor 6I, receives such information, i, from the corrector 9.

The sensors in FIG. 7a, FIG. 7b, FIG. 12a and FIG. 12b are based on the MS protocol. A feature of the embodiments presented is that if axial interval extension is known, then the edge detection may proceed faster than using FFT due to a reduced set of masks. For instance let us say that the axial position may vary only plus or minus a few axial resolution intervals, i.e. represented by plus or minus 5 mask indices in either direction away. The whole axial range delivered by FFT is not needed.

Another possibility to track a continuous drift, is to use a reduced number of masks around the new axial position if it is known that sudden big jumps are excluded from one correction to the next. Dynamic search in depth can be performed initially with a large number of masks, which after the contour is detected, the number of masks is reduced to maintain tracking.

Obviously, for ultra-fast sensing and parallel processing, it is possible to reduce delay between sensing and tracking to the time taken by a spectral scan, i.e. to perform the sequence of the two modes of operation for each r, sensing and axially tracking in a time interval matching the spectral scan duration. For instance, sweeping at 10 kHz would mean 0.1 ms per each imaging scan, event line 23I, and in this time, it would allow ultra-fast sensing at larger frequency rates to provide the mask indices in the array 83 within sensor 8S (FIG. 12a, 12b, 12c) in a fraction of this time and for the imaging to use the new mask or sets of masks to produce the images. In this respect, depending on the number of digital resources harnessed to work in parallel, and the imaging scan interval (period of moving from r to next lateral pixel in the imaging system $t_r$) and sensing scan interval (period of events $t_e$), the delay between sensing to axial tracking can be adjusted from the time of an imaging sweep, to the time taken to scan H number of pixels along the fast lateral scanning T-scan, $T_X/2$. As mask indices are stored in 83 and 9 and channeled spectra 20 in 99I, correction can also be done after the time of the raster (volume of data is acquired), i.e. the embodiments allow different solutions of correcting data for axial movement, from quasi real time to post acquisition long after both data were collected.

FIG. 13 describes a third embodiment of the apparatus that employs two sensors for better inference and processing of axial movements effects over the OCT images. A $1^{st}$ sensor, 81, as in FIG. 7a, 7b and FIG. 7c, uses the electrical signal due to the same channeled spectrum signal as that of the imaging interferometer, 201. A $2^{nd}$ sensor, 8S, uses a different interferometer, delivering channeled spectrum 20S, as in FIG. 11 and detailed in FIGS. 12a, 12b and 12c. The two interferometers use different optical sources as illustrated in FIG. 11 and they may acquire signal from the same part or different parts of the object, 3 and 3' as commented in this respect in connection to the $2^{nd}$ embodiment of the apparatus in FIG. 11.

Figure 13A:
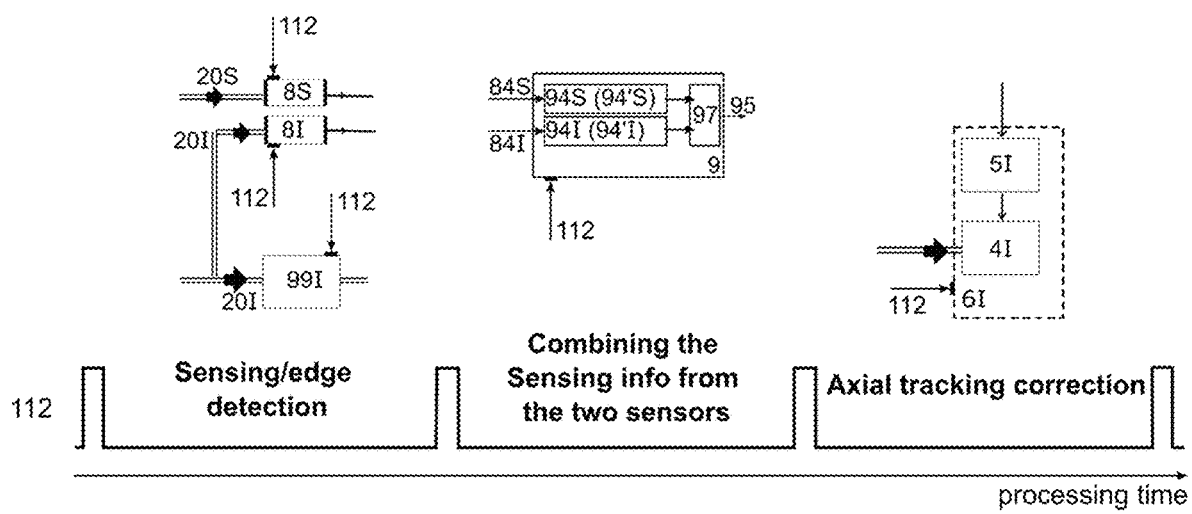
FIG. 13a illustrates the sequential use of blocks in FIG. 13.

As detailed in FIG. 13a, at a first stage, electrical signal corresponding to the channeled spectrum 201 from the imaging interferometer is stored in a storage 99I for each r along a T-scan over the object as object 3 and also, for each r, axial distance is sensed by the sensor 81 while sensor 8S operates at a sequence given by sensor spectral scans in 8S, $1/t_e$, at a faster sequence than spectral scanning rate, $1/t_r$ in the imaging interferometer, dictated by time events r. The results of sensing are placed in their respective memories 83 (not shown) in each of the two sensors.

As further detailed in FIG. 13a, at a second stage, the axial displacements delivered by the two sensors, represented as mask indices and their differences are stored in respective memories 94I and 94S, when using MS in the sensing. When using FFT for sensing, distances divided by the value of axial resolution interval, δ, are deposited into memories 94'I and 94'S. These are then combined by a calculator of distances 97. Let us say that the retina moves axially with the patient head. By deducting the two axial distances measured by the two sensors, the bulk axial movement is eliminated and the correction retained in corrector 9 is that due to the pulsatile blood flow in the retina only. This can be used for elasticity measurements and for diagnosis. In this way, dual functionality is achieved: (i) for en-face OCT images, correction from 81 is used only, in order to remove both the bulk and blood pulsatile axial movements, (ii) for measurement of the heart rate, activity in embryos, or measurements under a stimulus, such as air puff to evaluate tissue elasticity, such as in surgery or diagnosis via palpation, combined data from the two sensors are used for diminishing disturbances of measurements due to the bulk movement of the retina or tissue.

Figure 13B:
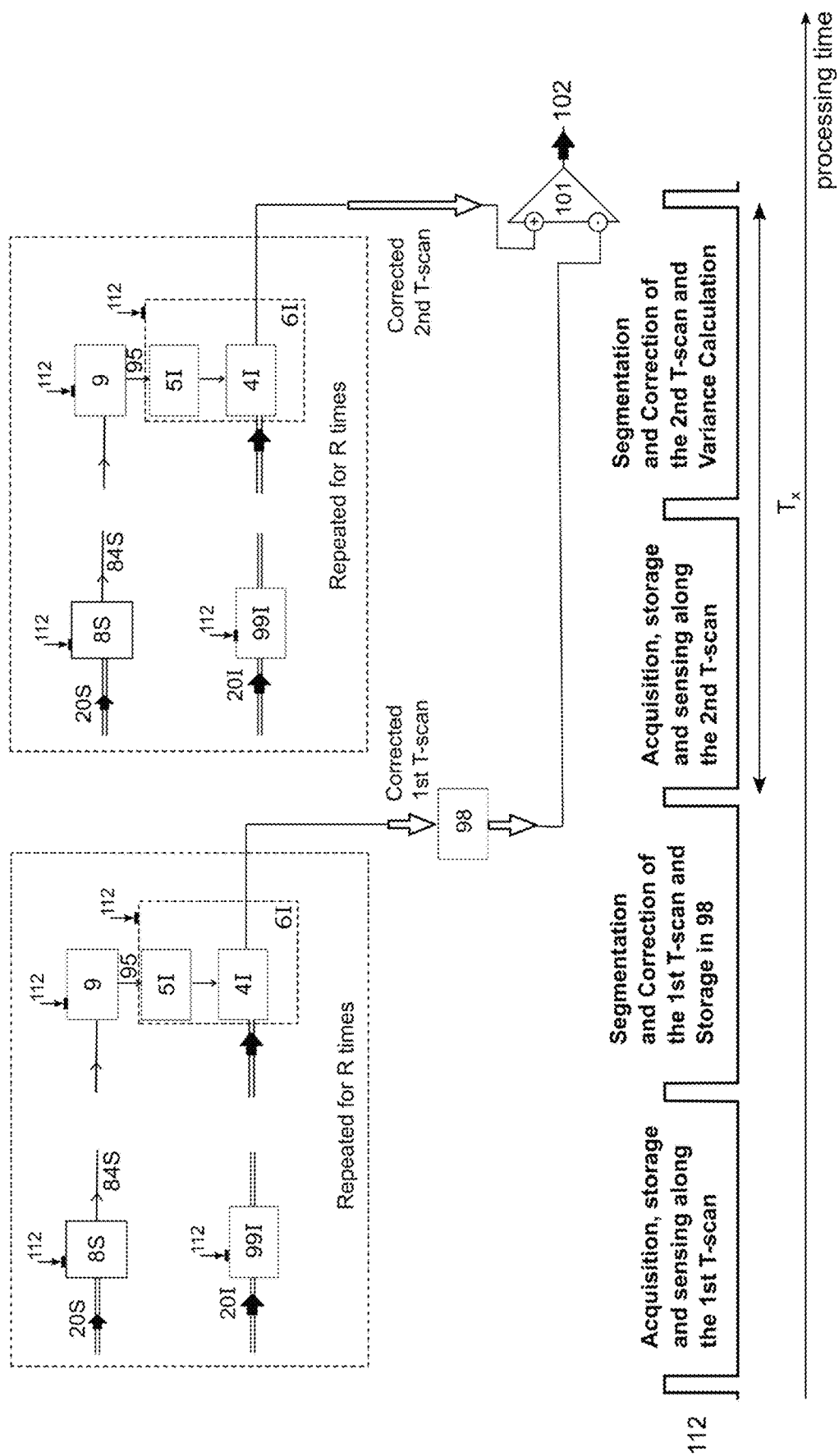
FIG. 13b discloses the production of variances of T-scans.
Figure 13C:
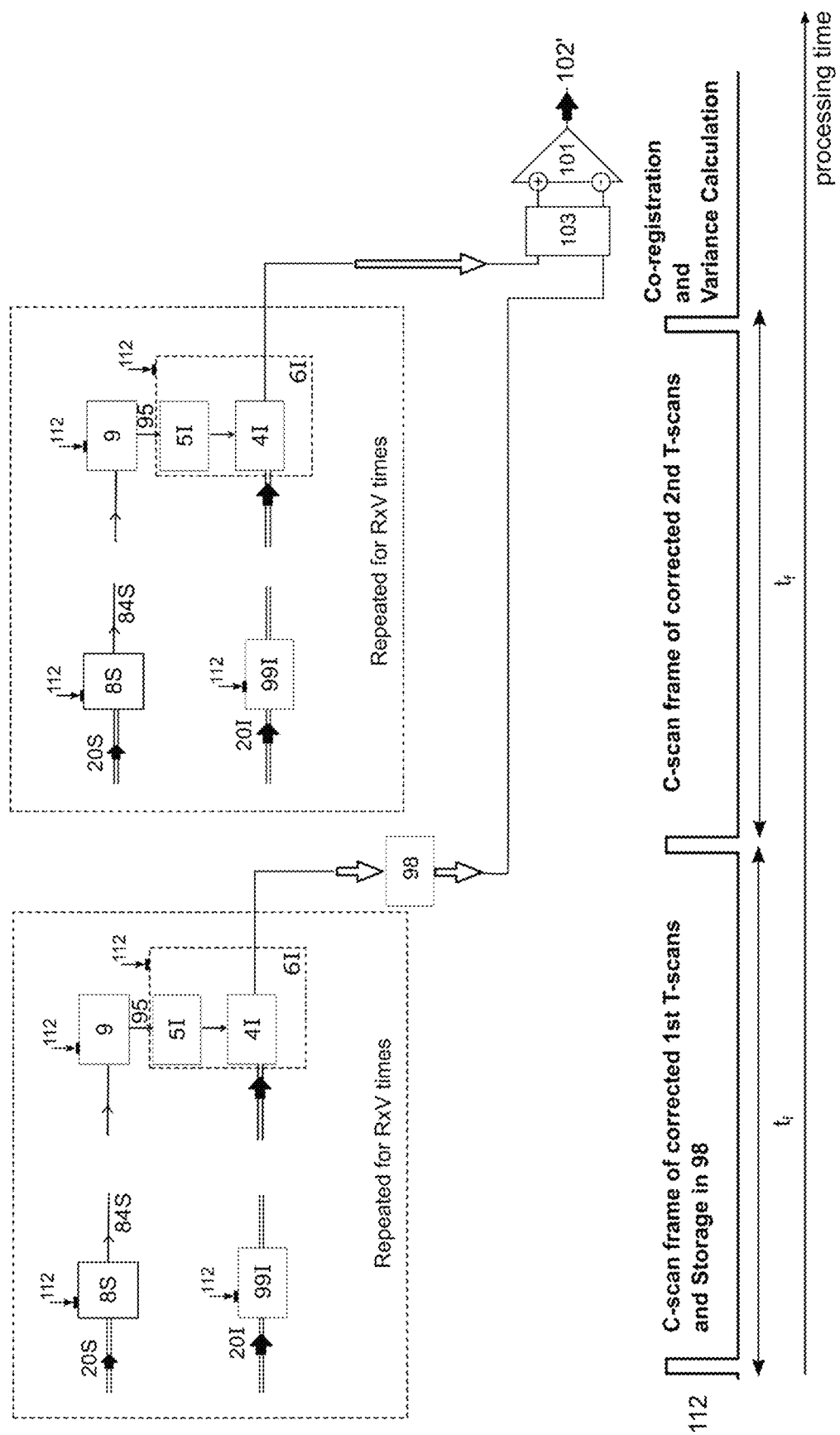
FIG. 13c discloses the production of a C-scan OCTA image.
Figure 13D:
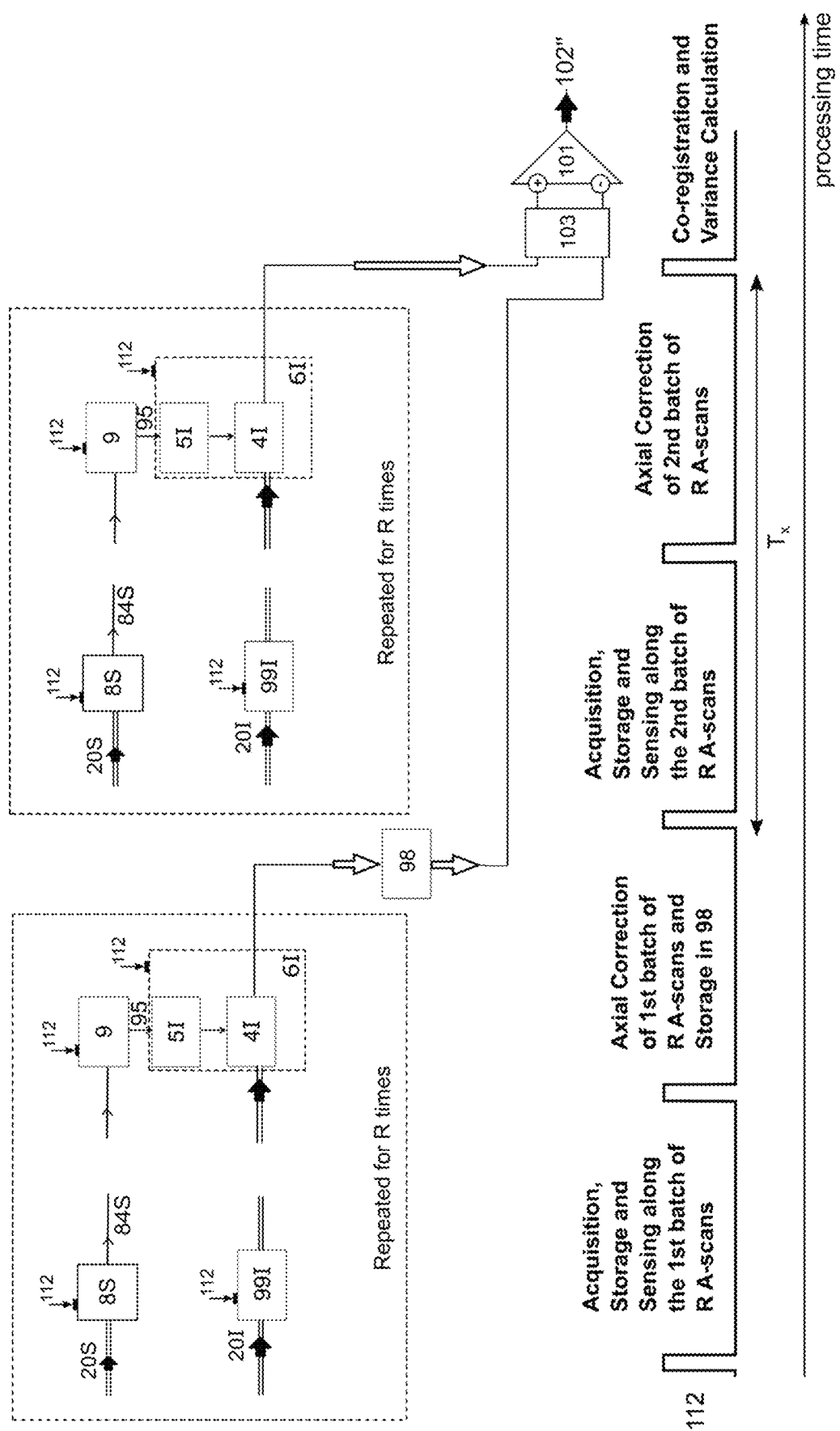
FIG. 13d discloses the production of a B-scan OCTA image.

FIGS. 13b, 13c and 13d illustrate the utilization of the embodiments of the apparatus in FIG. 6, 11 or FIG. 13 to deliver in quasi real time, OCTA images. In this case, the slow (frame) lateral scanner 111, is driven by a stepwise signal varying in stairs, where the voltage applied is maintained on each step for as long as necessary for acquiring at least two T-scans. As shown in FIG. 13b, two corrected T-scan profiles are obtained at two moments in time, differing by a period Tx of the lateral fast scanner 110. Two T-scans are collected at the same vertical coordinate, y. Then a speckle variance calculation of the two corrected T-scans for curvature and axial movement leads to a T-scanA profile that should retain only features that manifested variance in the intervening time. This is useful in detecting blood flow. The $1^{st}$ T-scan profile is stored in memory 98 until data for a $2^{nd}$ T-scan is processed. Then a $2^{nd}$ T-scan profile is produced and their variance is calculated in the Variance calculator 101. The output 102 represents a variance T-scan, T-scanA, at the vertical coordinate y. Two T-scans are collected from the same vertical coordinate, y, while applying a saw-tooth signal to the lateral scanner 110, in which case the delay between the two T-scans is $T_X$, as shown.

To avoid the flyback due to switching back a scanner in a short time, when using a sawtooth signal, a triangular signal can be used, in which case each T-scan is bidirectional. In this case, 4 unidirectional T-scans are acquired for each y, two on the ascending ramps and two on the descending ramps, to perform variance calculation between the information collected during deflection events in the same direction (variance applied to the acquired data on the $1^{st}$ and $3^{rd}$ ramps, both ascending, and variance applied to the acquired data on the $2^{nd}$ and the 4th ramps, both descending). In this case, $1^{st}$ Tscan and $2^{nd}$ T-scan in FIG. 13b both refer to a complete lateral scan, left-right followed by right left, i.e. obtained for both raising and falling ramps applied to the fast scanner 110.

The resulting TscanA is made from an OCTA scan for left-right deflection and continuing with an OCTA scan for right-left deflection. An overall TscanA at the coordinate y is obtained by superposing one with the other one flipped horizontally.

Different other scenarios are possible, where more than two T-scans are used in calculation of the variance. It is also possible to apply variance between the two signals acquired during opposing deflections, obtained from the two ramps of a triangular signal. In this case, the time intervals between the pulses 112 in FIG. 13b is not $T_X/2$ but $T_X/4$, i.e. a 1st T-scan is acquired on the increasing ramp of the triangular signal and the $2^{nd}$ T-scan is collected on the decreasing ramp of the triangular signal, each ramp lasting $T_X/2$. The R calculations for R lateral pixels are now done in a $T_X/2$ interval. However it should be noticed that in this case, for a pixel r in the final TscanA profile, the delay for which the variance is evaluated varies between 0 and $T_X/2$, i.e. the contrast of OCTA information will vary along the direction of the fast scanner. In our example, this is along X (horizontal). This could advantageously be used in displaying OCTA information from regions with slow and high speed flow along the direction of the lateral scan.

By repeating the process in FIG. 13b, at the next vertical position y+1, i.e. for another stepped voltage applied to the slow scanner 111, another TscanA is obtained from two or more T-scans. By repeating the process for all V lines, and grouping all such T-scanA profiles into a frame, after V repetitions, a 2D map of OCTA en-face images is synthesized, corrected for curvature and axial movement. This method can produce a complete en-face OCTA image in the time of a frame, $t_F$. This method avoids any transfer of data to software calculations to co-register images to reduce their axial movement effects and to flatten them, that takes time in prior art.

The method can be repeated for many other depths, Q, to produce Q C-scans. By parallel processing, these can be obtained in the same time of a frame, $t_F$. It should be noticed, that for repeating calculations for other depths, the same information of axial correction is used in all, i.e. the same difference of indices i delivered by the corrector 9. These indices are being advanced by one for each new C-scan, to obtain a flattened C-scan image below the previous C-scan, all flattened. This means that sensing, as a process is required only once and not repeated Q times, in order to obtain volumetric data of OCTA information in Q C-scans.

As the masks are complex, variance calculation for the two images can involve modulus and phase of the complex signal, according to means known in the art for evaluating amplitudes and phase variance from one image to next. Calculation of differences is similar to that used in the paper by S. Caujolle, R. Cernat, G. Silvestri, M. J. Marques, A. Bradu, T. Feuchter, G. Robinson, D. K. Griffin and A. Podoleanu, "Speckle variance OCT for depth resolved assessment of the viability of bovine embryos", Biomed. Opt. Express 8, 5139-5150 (2017). This refers to squared differences of amplitudes for each r pixel across two T-scans acquired, delivering the variance signal:

$$SV(r) = \frac{1}{P}\sum_{r=1}^{P}\left[A(r) - \frac{1}{P}\sum_{r=1}^{R}A(r)\right]^2 \quad (8)$$

for each r, where P is the number of images in the calculation of variance, with P=2 in FIG. 13b. and could be larger. Other formulae can be used known in the art, such as measuring decorrelation mapping, as explained in several papers on OCTA such as in "Comparison of amplitude-decorrelation, speckle-variance and phase-variance OCT angiography methods for imaging the human retina and choroid," by Iwona Gorczynska, Justin V. Migacz, Robert J. Zawadzki, Arlie G. Capps, and John S. Werner, published in Biomed. Opt. Express 7, 911-942 (2016).

In prior art OCTA, co-registration of images is used to eliminate the movements between OCT slices prior to flattening and then slicing the volume of OCT data to obtain en-face OCTA images. Performing flattening and axial tracking as disclosed here, the en-face OCT images so generated are easier to be subsequently co-registered, as major components marring the presentation of 3D OCTA signal, curvature and axial movement, are reduced or eliminated. Such a method, made possible by the present embodiments, is disclosed in FIG. 13c. As a difference to FIG. 13b, here a complete C-scan is assembled from all $1^{st}$ T-scans and another complete C-scan is assembled from all $2^{nd}$ T-scans. Then the two images are co-registered in the co-registration processor, 103. This involves taking data out and processing it in software. In this case, what are sent to a similar Variance calculator as 101 are two maps of co-registered, already corrected for curvature and axial movement en-face OCT images. This method simplifies the task of co-registration. In prior art, co-registration is used, by software means, to reduce the effects of both axial and lateral movements. Here software co-registration is only used for lateral movements. The method utilizes two C-scan images, each made from V T-scans, each corrected for curvature and axial displacement. However 98 operates after the whole frame of the $1^{st}$ C-scan is assembled, i.e. $t_F$, where $t_F=VT_X$. Using the numerical values above, with V=200 lines, using a sawtooth signal driving the fast lateral scanner 110, and Tx=2 ms, with H=200 pixels along each T-scan, $t_F$=0.4 s. For each vertical coordinate y, two T-scans are acquired, with a delay interval Tx. The two C-scans are: a $1^{st}$ C-scan made from corrected $1^{st}$ T-scans and a $2^{nd}$ C-scan made from corrected 2nd T-scans. The variance calculation accumulates over $T_X$=2 ms. The co-registration reduces the lateral movement of pixels in the two, already flattened and corrected C-scans for axial displacements, leading to a C-scan OCTA image, 102'.

For the procedures described in FIGS. 13b and 13c, flattened C-scan images are produced by engaging MS-processors as disclosed in FIGS. 6a and 6c, where a single MS-calculator 41 is engaged in the compound comparator 4.

Alternatively, embodiments allow similar processes engaging the MS-processors 6 in FIGS. 6b and 6d engaging multiple MS-calculators generating an A-scan for each r. Such a method is described in FIG. 13d. In this case, variance is calculated between corrected assemblies of B-scans, $1^{st}$ B-scan made from $1^{st}$ collection of R A-scans at a coordinate y and a $2^{nd}$ B-scan made from $2^{nd}$ collection of R A-scans at the same coordinate y. The delay between the two A-scans for each r in the two B-scans, for each y vertical coordinate, important in determining the strength of the variance calculation is again $T_X$. The two B-scans so obtained are first subjected to co-registration in 103, done by software, so in post acquisition, and then subject to variance calculation on 101, to obtain a B-scanA image, 102".

Not shown, pairs of B-scans could be generated for the whole set of V coordinates, i.e. repeating generation of B-scans for V times, for the number of lines in the frame. They could be on pairs, subject to co-registration as in FIG. 13d or they could be assembled in two volumes, followed by co-registration and then variance calculation over the volume data. The output will be now a volume of B-scanA images, i.e. a volume of B-scanA images made from A-scans corrected axially by the embodiments complemented by co-registration between the two volumes in post-acquisition.

To produce a volume angiography information, the process in FIG. 13c is repeated for many other depths and the resulting C-scanA images superposed. Similarly, all B-scanA images for all V coordinates using the method in FIG. 13d can be used to assemble a volume of OCTA data. Then, by software, C-scan OCTA slices can be obtained from this volume, or the whole volume of data collapsed in an overall C-scan OCTA image.

Another advantage of the embodiments described herein is adaptability to variation of the axial resolution, for instance by reducing the tuning bandwidth that leads to an increase in the axial depth interval, $\delta$, with advantage in in the time demanded for the calculations. For an A-scan with M=1024 points, M/2=N=512 depth points are needed. Considering an axial resolution of $\delta$=5 microns, this correspond to a thickness of tissue of ~2.5 mm. This involves ~M $\log_2$ M FFT calculations. For better stability and improved consistency of vessels produced in the OCTA image, averages over the axial range are performed to reduce the axial resolution, let us say by a factor of 4, to 20 microns. This reduces the number of depth resolved points for both MS and FFT, that reduces the FFT advantage in terms of speed in comparison with the MS technology. With MS, a single multiplication of a mask of M points is needed for each depth. A MS-calculator for each depth can be configured in a FPGA, where each has to do a single multiplication. MS is ideally suited using poorer resolution spectrometers or wider linewidth swept source, where for a retina tissue of 0.5 mm, with 20 micron resolution, 25 such MS processors as in FIGS. 7a and 7b may suffice, working in parallel, instead of performing FFT over 1024/4=250 points. Each such processor performs a single multiplication of the channeled spectrum 20 with the selected mask corresponding to a corrected depth, delivered by the Mask selector in each depth channel.

Superposing the en-face OCTA images of the output of all such processors, for all depths, leads to an overall OCTA image.

Figure 14:
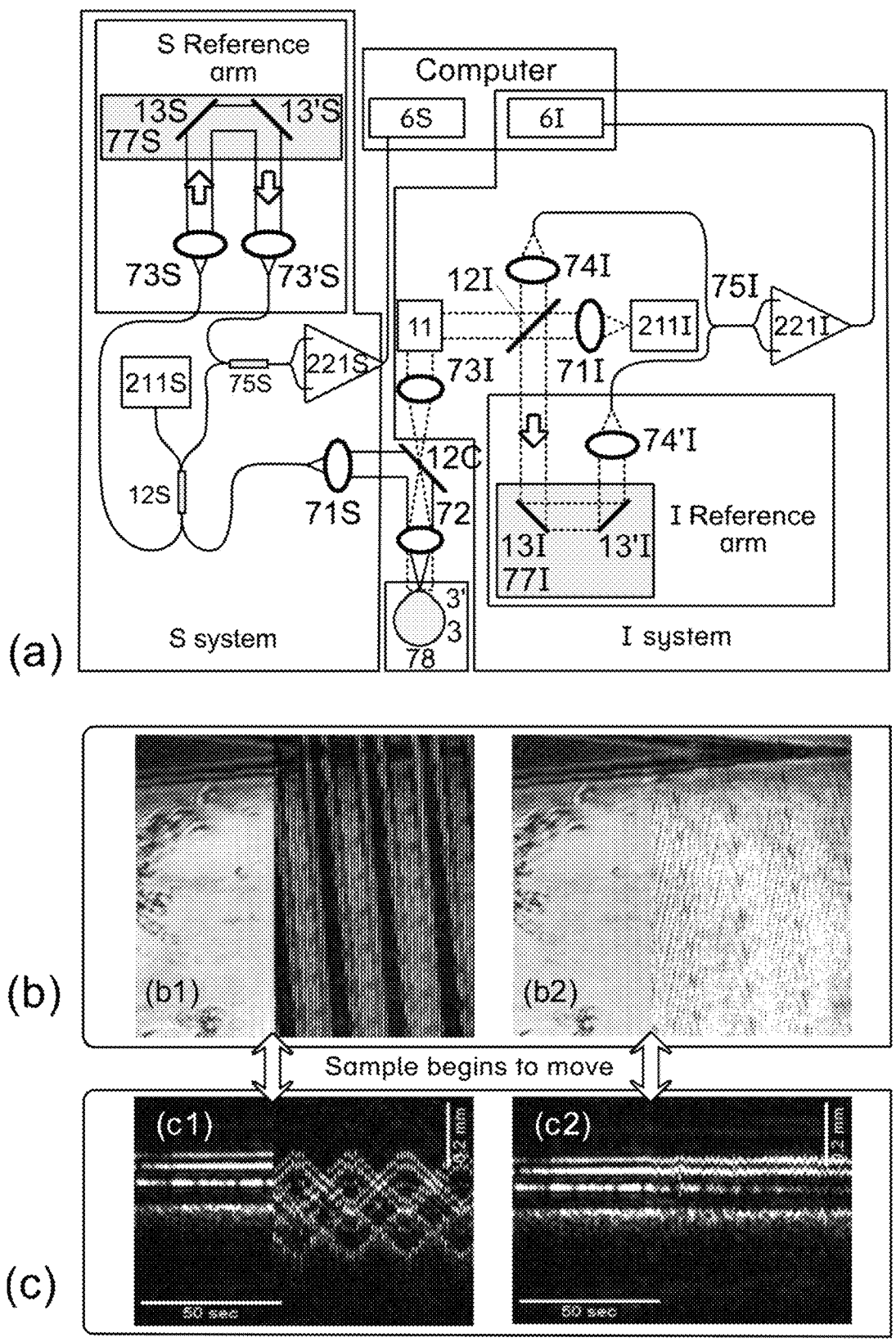
FIG. 14 illustrates images obtained from an eye model using a system based on the embodiment in FIG. 11, without axial tracking and with axial tracking enabled.

A proof of concept of axial tracking with a sensor based on the second embodiment in FIG. 11 is presented in the following. This is based on the embodiment of the apparatus, acquiring OCT images under correction from a sensor 8S using a swept source 211S, where the system implements real time OPD correction via non mechanical correction according to embodiments. This is based on the embodiment of the MS-processor in FIG. 6 and the embodiment of the apparatus in FIG. 11, with details as shown in FIG. 14. Here an imaging system capable of compensating axial movements of the object, retina 3, by the joined action of the two systems, one performing imaging and the other sensing, is schematically represented in FIG. 14(a): a system employed for imaging, referred as imaging system, I, and another system employed for axial sensing, referred as S. The sensor 8S employs an interferometer illuminated by a 1300 nm swept source, as 211S, with a 10 kHz sweeping frequency (Santec HSL-2000-12-MDL). The object beam is focused on the object 3, an artificial eye (Rowe Technical Design OCT Model Eye), mounted on a translation stage, 78, (Newport VP-25XA) to exercise controlled movement of the object (3 and 3', the front lens as cornea and the phantom retina 3) to test the OCT apparatus tolerance to movement.

The resulting channeled spectra are detected by a balanced photo-detector, Santec BPD-200, 200 MHz cutoff frequency, as 221S, and the corresponding electrical signal is sent to a processor 6S, performing FFT, consisting in a National Instruments PCI5124 card with a 25 MS/s sampling rate, mounted in a PC (Intel Core i7-77700K 4.20 GHz, 16 Gb RAM, Windows 10 64 bit, GPU NVIDIA GeForce GT 710). For the imaging system, a swept source 211I was used, with a 2 kHz sweeping frequency, 850 nm central wavelength and a tuning range of 50 nm (IS source, Superlum BroadSweeper 840). The resulting channeled spectra are detected by a custom-made band pass photodetector, 221I (1 MHz cutoff frequency) and the corresponding electrical signal is sent to the MS processor 6I, consisting in an AlazarTech ATS9350 acquisition card sampling at 2 MS/s. By setting appropriate spectral tuning ranges, both systems have a similar axial resolution in air of ~6.7 µm. The position of the peak of maximum amplitude, due to the top of the eye model 3', within the A-scan, along the OPD coordinate, is used to select the starting index of the subset of masks employed in the MS imaging processor 6I. The compensation is applied to individual A-scans, allowing it to operate both inter- (FIG. 14 (b1-b2)) and intra-B-scan (FIG. 14 c1-c2).

Figure 5:
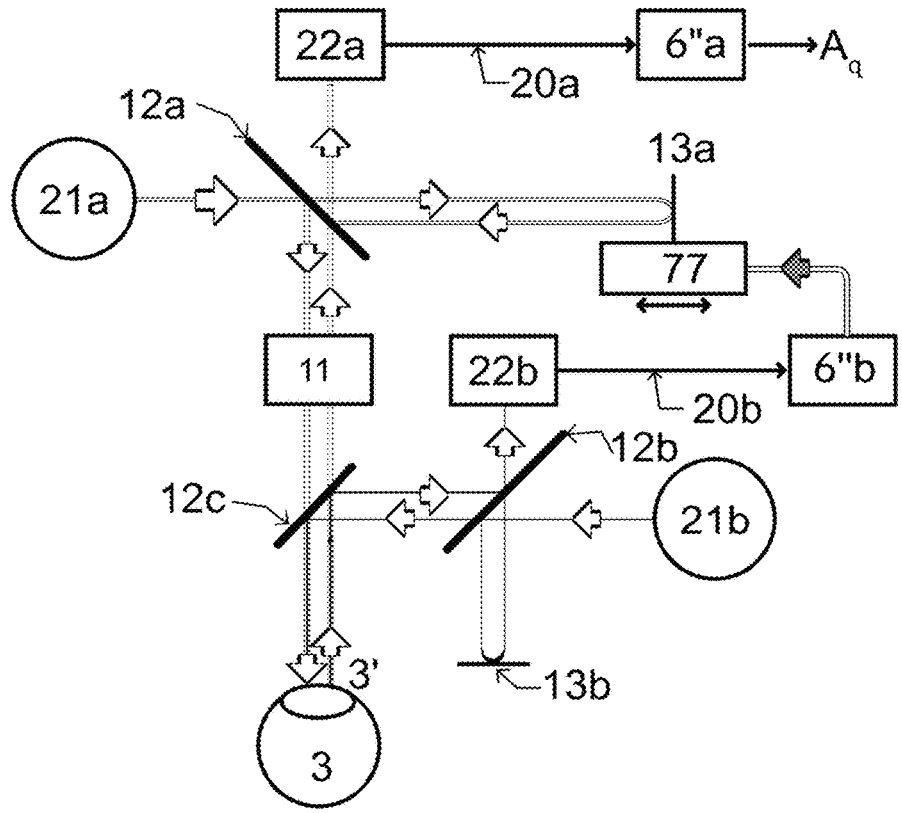
FIG. 5 shows in diagrammatic form an axial tracker of a moving object according to prior art.

In the sensor S system, light from the swept source 211S is sent to a coupler 12S 20/80, with 20% power sent to the object arm, via collimator 71S, and then to a splitter 12C (Dichroic Thorlabs DMSP950L) and lens 72. Light from the top of the object, the lens of the eye model, 3', returns via the lens 72, splitter 12C, lens 71S and coupler 12S towards the balanced coupler 75S, 50/50, towards the balanced photodetector 221S. The other input of the balanced coupler is fed via the reference arm of the sensor S, via lenses 73S and 73'S. The OPD in the $2^{nd}$ interferometer is adjusted via reference mirrors 13S and 13'S placed on a translation stage 77S. Mechanical correction in prior art in FIG. 5, is replaced with sliding mask indices to be used by 6I.

In the I system, light from the swept source 211I is sent to a splitter 12I via lens 71I, 20/80, with 20% power sent to the object arm, via dual head galvoscanner 11, via collimator 73I, and splitter 12C and lens 72. Light from the object 3 (mimicking the retina) returns via the lens 72, splitter 12C, collimator 73I, galvoscanner 11, towards splitter 12I, followed by the collimator 74I and then to the balanced coupler 75I, 50/50, towards the balanced photodetector 221I. The other input of the balanced coupler 75I is fed via the reference arm, via reference mirrors 13I and 13'I and lens 74'I placed on a translation stage 77I.

FIG. 14 (b) shows en-face C-scan images acquired without (b1) and with (b2) axial motion compensation and in (c) Images acquired without (c1) and with (c2) axial motion compensation.

A moving subset of Q=150 masks, equivalent to a 1 mm of axial interval measured in air was used, over a range of N=500 masks, equivalent to 3.35 mm, to process each A-scan. Therefore, axial movements up to ±1.175 mm could be compensated. The stage 78 was controlled with linear motion amplitudes of 0.2 mm, 0.5 mm and 1 mm, and speeds of 0.5 mm/s, 1 mm/s and 2 mm/s. The resulting images were corrected both in real-time and in post-acquisition. Using the set-up in FIG. 13(a), motion artefacts were reduced; to quantify this reduction, the numerical cross-correlation between B-scan frames was computed. Prior to the start of the sample movement, the normalized correlation value between B-scans was ≈0.9 (on average). With the introduction of the object motion, the cross-correlation value between B-scans drops to ≈0.26 with no correction applied; with the feedback loop enabled, this figure increases to ≈ 0.75. The drop from 0.9 to 0.75 may be attributed to residual lateral vibrations from the stage, since only axial compensation was applied.

The embodiments presented are not exhaustive, have been presented as a matter of example and modifications and other possibilities exist without departing from the spirit of the embodiments described herein.

The use of one, two or three $T_s/2$ intervals at the bottom of FIGS. 7a, 7b, 7c, 12a, 12b, 12b, 13a, 13b, 13c and 13d is shown for the illustration only and depending on the parallel resources allocated other scenarios can be implemented with the same structure of embodiments presented. If sufficient parallel digital resources are allocated, all processes can be done with minimum delay between them implementing a quasi real time correction.

It should also be obvious for those skilled in the art, that where a compact 2D lateral scanner is mentioned, this can equally be implemented using separate lateral scanners incorporating interface optics between them.

Adjustment of OPD was shown by using means in the reference path of the interferometers, however equally they can be applied into the object paths according to similar means, as known in the art.

As a matter of preference, embodiments are using refractive elements, but this is not a limitation of the embodiments described herein and any such element can be equally replaced with reflective elements.

Fiber splitters and plate beamsplitter have been shown as a 2 input by 2 output splitting elements, but equally, other splitting elements can be employed such as cube beamsplitters, and where a fibre or bulk optics splitter was employed, a bulk splitter and respectively a fibre element can be employed instead.

The invention claimed is:

1. An optical coherence tomography (OCT) apparatus, comprising:

an optical imaging source launching a beam of light into a two arm imaging interferometer, and wherein due to interference of light returning from the two arms, an optical spectrum at an output of the two arm imaging interferometer is modulated to produce an optical channeled spectrum, wherein the optical imaging source is a swept source, an arm of the two arm imaging interferometer comprises a lateral scanner and an object to be imaged, and the lateral scanner scans the beam of light from the source towards the object in two lateral directions over r=1, 2 . . . R lateral pixels, where R is an integer, where the OCT apparatus further comprises:
an imaging detector,
a corrector,
a sensor,
an imaging Master Slave (MS) processor comprising a mask selector and a dynamic MS comparator with at least two inputs and, where the mask selector delivers at least one mask signal at its output, to the dynamic MS comparator, wherein for each lateral pixel, r, addressed by the lateral scanner, the OCT apparatus performs a spectral scan, comprising scanning the optical channeled spectrum at the two arm imaging interferometer output and where due to the spectral scan, the imaging detector delivers an electrical signal due to the optical channeled spectrum at the output of the two arm imaging interferometer, wherein the dynamic MS comparator comprises at least one MS-calculator, the at least one MS-calculator comprising two inputs, wherein one of the two inputs is for receiving the at least one mask signal delivered by the mask selector and the other input is for receiving the signal delivered by the imaging detector, wherein the mask selector comprises a store for two system functions g and h, the function g incorporating a chirp of the optical channeled spectrum due to nonlinear sweeping of the swept source and the function h incorporating the chirp of the optical channeled spectrum due to dispersion in the interferometer, and a mask-calculator, and where the mask selector is under a control input, where the mask signal represents an electrical replica of the optical channeled spectrum at the imaging interferometer output for a specific depth in the object $z=m\delta$ where $\delta$ is an axial resolution interval of the OCT and m is a mask index, where the mask-calculator in the mask selector operates a Master Slave algorithm that, based on the functions g and h, calculates any mask signal for any specific mask index determining any specific depth in the object, where a choice of mask indices of the mask signals to be calculated is controlled by signal received from the control input, where the sensor further comprises a sensor storage of mask indices, where the sensor measures an axial distance up to a part of the object, where that part coincides with the part being imaged by an optical beam from the imaging interferometer or is different than the part being imaged by the optical beam from the imaging interferometer, and where the axial distance measured is converted into the mask index, that is deposited in the sensor storage of mask indices, wherein mask indices for each r are converted by the corrector into a difference of mask indices in respect to a reference mask index that the corrector sends to the control input of the mask selector, wherein, based upon the difference of mask indices received at its control input, the mask selector calculates the at least one mask signal, and where the MS-calculator operates based on a Master Slave algorithm to deliver a reflectivity value from a depth z inside the object, that is the specific depth of the mask signal delivered by the mask selector to the dynamic MS comparator.

2. The OCT apparatus according to claim 1, where the mask selector further comprises a storage of masks calculated by a mask calculator and a distributor comprising a plurality of outputs, that under the control input distributes at the plurality of outputs of the distributor, the at least one mask signal from the storage of masks, towards the dynamic MS comparator.

3. The OCT apparatus according to claim 1, where the optical imaging source is a swept narrowband source and the imaging detector is a photodetector or a balanced photodetector and where the spectral scan means sweeping the optical spectrum emitted by the swept source at each r pixel, or where the optical imaging source is a broadband source and the imaging detector is a spectrometer and where the spectral scan means reading content of the spectrometer at each r pixel.

4. The OCT apparatus according to claim 1, where the sensor further comprises:
a thresholder, and
a sensor Master Slave processor whose input is connected to the output of the imaging detector, comprising Q two input MS-calculators, where the sensor storage of masks indices is organized as a matrix of Q rows and R columns, where Q is an integer, and where the thresholder delivers an array of mask indices to the sensor storage of masks indices for each r, populating its columns for each r at a time, where all indices in the column are set to nil, apart from a single index q of that mask that determined a variation of: the Master Slave signal strength along the depth in the object from mask index q to mask index q−1 larger than a threshold value in an array of set threshold values, with a value for each lateral pixel r.

5. The OCT apparatus according to claim 1, further comprising:

R storages of signals representing optical channeled spectra, a storage for each r, acquired from the imaging detector, where the sensor further comprises:
a storage of masks containing Q mask signals,
a thresholder,
a sensor Master Slave processor comprising R two input MS-calculators, whose first inputs are connected each to the storage of each signal representing an optical channeled spectrum r and where all second inputs are tied up to a common entry receiving a mask signal at a time from the storage of masks signals, where the sensor storage of masks indices is organized as a matrix of Q rows and R columns, where Q is an integer, and where for each mask delivered by the storage of masks signals to the common entry connected to the second input of the R two input MS-calculators, the R two input MS-calculators deliver R Master Slave reflectivity strengths to the thresholder, where the thresholder contains a level comparator, and where the thresholder delivers an array of mask indices to the sensor storage of masks indices for each index q, where q=1, 2 . . . Q, populating its rows for each q at a time, where all indices in the rows are set to nil, and apart from those lateral pixel indices, where a variation of: the Master Slave signal strength along the lateral pixel r, from pixel r to pixel r-1 is larger than a threshold value in an array of set threshold values, with a value for each lateral pixel r.

6. The OCT apparatus according to claim 1, where the sensor comprises:
a thresholder,
a Fourier Transform (FT) processor whose input is connected to the output of the imaging detector, that produces an A-scan for each r spectral scan,
where the sensor storage of masks indices is organized as a matrix of Q rows and R columns, where Q is an integer,
where the thresholder delivers an array of mask indices to the sensor storage of mask indices for each r, populating its columns for each r at a time, where all indices in the column are set to nil,
apart from a single index m that determined a variation of: the A-scan signal strength along the depth in the object from distance (m−1)δ to mδ larger than a threshold value in an array of set threshold values, with a value for each lateral pixel r, and
where δ is the axial resolution interval of the OCT and m an integer number.

7. The OCT apparatus according to claim 1, where the sensor targets a layer at a certain depth in the object, and where the OCT apparatus further comprises:

a mode switch synchronized with the lateral scanner, to switch the operation of the OCT apparatus between two operational modes, sensing and flattening, where the OCT apparatus additionally comprises a store of R storages, a storage for each signal representing an optical channeled spectrum r, where the mode switch, during a first lateral scan, switches the OCT apparatus into the sensing operational mode, when signal is acquired from the imaging detector and each signal representing the optical channeled spectrum r is deposited for each r into the store r of the R storages, the sensor determines for each lateral pixel, r, an axial position of that pixel object in respect to the axial distance of a reference pixel, and converts that distance information into a mask index that is deposited into the Sensor storage of mask indices, and where the mode switch, during a next lateral scan, switches the OCT apparatus into flattening operational mode, where depending on information of axial distance received from the sensor storage of mask indices, for each r, the corrector actuates on the mask selector to generate or select a single mask to be provided as input to the sensor Master Slave processor to perform a Master Slave protocol with the r-th electrical signal representing the optical channeled spectrum stored during the sensing mode, to produce the reflectivity of the pixel r in a flattened en-face OCT image at a depth of the mask used, selected in respect to the layer targeted by the sensor.

8. The OCT apparatus according to claim 1, where the sensor targets a layer at a certain depth in the object, and wherein the OCT apparatus further comprises a mode switch synchronized with the lateral scanner, to switch the operation of the OCT apparatus between two operational modes, sensing and flattening, wherein the OCT apparatus additionally comprises a store of R storages, a storage for the electrical signal representing each channeled spectrum r, where the mode switch, during a first lateral scan, switches the OCT apparatus into the operational sensing mode, when signal is acquired from the imaging detector and each signal representing the optical channeled spectrum r, is deposited for each r into the storage r of the R storages, the sensor determines for each lateral pixel, r, an axial position of that pixel object in respect to the axial distance of a reference pixel, and converts that distance information into a mask index that is deposited into the sensor storage of mask indices, and where the mode switch, during a next lateral scan, switches the OCT apparatus into flattening operational mode, where depending on information of axial distance received, the corrector actuates on the mask selector to generate or select Q masks, where Q is an integer, to be provided as inputs to the Imaging Master Slave processor to perform a Master Slave protocol with the stored electrical signal representing the r-th optical channeled spectrum during the sensing mode, to produce an axial reflectivity profile of Q depths at each pixel r in a cross section OCT image, flattened along the depth of the layer targeted by the sensor.

9. The OCT apparatus according to claim 1, where the sensor collects signal from a second two arm interferometer and further comprises a second optical source, where one arm of the second interferometer shares its path with the imaging interferometer to send a second beam of light from the second optical source towards the object and to collect signal from the object, where due to interference, the optical spectrum at an output of the second interferometer is modulated producing a second optical channeled spectrum, where the sensor further comprises:

a second detector producing an electrical signal representing the second optical channeled spectrum at the output of the second interferometer, a sensor thresholder, a sensor Master Slave processor for the signal at the output of the second detector, containing a sensor mask storage, a sensor compound level comparator of N MS-calculators, where N is an integer, wherein in a sensor storage of mask indices for each time event, e=1, 2, . . . E, where E is an integer, during an observation time length, where E is larger than R, and where the sensor thresholder contains a sensor level comparator of the Master Slave signal strength delivered by each MS-calculator in the compound comparator with a threshold value in an array of set threshold values, with a value set for each time event e, and where the sensor level comparator of signal strength delivers an array of mask indices that are placed in the sensor storage of mask indices for each e.

10. The OCT apparatus according to claim 9, where the second optical source is a second swept narrowband source and the second sensor detector is a second photodetector or a balanced photodetector and where the spectral scan means sweeping the optical spectrum emitted by the second swept source at each e event, where e=1, 2, . . . E with E>R or where the second optical source is a second broadband source and the second sensor detector is a second spectrometer and where the spectral scan means reading content of the second spectrometer at each e event, where e=1, 2, . . . E with E>R.

11. The OCT apparatus according to claim 1, where the sensor collects signal from a second two arm interferometer and further comprises a thresholder and a second optical source, where one arm of the second interferometer shares its path with the imaging interferometer to send a second beam of light from the second optical source towards the object and to collect signal from the object, where due to interference, the optical spectrum at the output of the second interferometer is modulated producing a second optical channeled spectrum, where the sensor further comprises:

a second detector producing an electrical signal representing the second optical channeled spectrum at the output of the second interferometer, a sensor thresholder, in a Fourier Transform (FT) processor for the signal at the output of the second detector, and in a sensor storage of mask indices for each lateral pixel r, where the thresholder contains a level comparator of an FFT signal strength with a threshold value in an array of set threshold values, with a value for each time event e=1, 2, . . . E, where E>R, and where the level comparator of the FFT signal strength delivers an array of distance positions in depth, that after division of such distance by δ, where δ is the axial resolution interval of the OCT, the results are placed in the sensor storage of mask indices for each e.

12. The OCT apparatus according to claim 1, where the sensor is connected to the output of the imaging detector and where the OCT apparatus further comprises a second sensor, where the corrector admits signal from a second input and where the second sensor senses an axial position of the object and the output of the second sensor drives the second input of the corrector.

13. A method for imaging a curved, axially moving object, the method comprising:

using a Master Slave-OCT protocol applied to two electrical signals, one electrical signal represented by a mask signal and the second electrical signal represented by a signal delivered by an imaging detector, at the output of a two beam imaging interferometer producing interference of light, from light collected from an object arm and from a reference path, wherein the object arm comprises a lateral scanner;

associating the mask signal to a mask index that represents a depth in the object;

performing a spectral scan on each lateral pixel of the object to deliver the second electrical signal;

for each lateral pixel addressed by the lateral scanner, using a sensing method to sense a variation of depth of the lateral pixel of a targeted layer, that is translated into a variation of the mask index, where the variation of depth is due to a cumulated effect of object curvature and object axial movement, wherein the sensing method operates in synchronism with the lateral scanner; and using a correcting method to prepare the mask index of the mask signal selected to be used by the Master Slave-OCT protocol to generate a signal reflectivity from the depth in the object as represented by the mask index of the mask signal selected, wherein the correcting method comprises dynamically varying the mask signal used by the Master Slave-OCT protocol according to the sensing method.

14. The method according to claim 13, wherein the sensing method uses the same signal collected by the imaging interferometer to sense an axial position of each pixel laterally scanned using the Master Slave-OCT protocol, and based on axial distances measured, establishes an array of correcting indices placed in a corrector, where the method further comprises dynamically changing the mask indices used by the Master Slave-OCT protocol for creating the OCT images using the array of correcting indices.

15. The method according to claim 13, where the sensing method uses the same signal collected by the imaging interferometer to sense an axial position of each pixel laterally scanned using Fourier Transform processing, and based on axial distances measured, establishes an array of correcting indices placed in a corrector, where the method further comprises dynamically changing the mask indices used by the Master Slave-OCT protocol for creating images using the correcting indices.

16. The method according to claim 13, where the sensing method comprises:

using a second interferometer to collect scattered light from the same or a different part of the object than a part used by the imaging interferometer;

using the scattered light to sense an axial position of the object;

based on axial distances measured, establishing an array of correcting indices and placing the array of correcting indices in a corrector; and dynamically changing the mask indices used by the Master Slave-OCT protocol for creating images using the correcting indices.

17. The method according to claim 16, where the correcting method employs results of the sensing method using both signals from the imaging interferometer and from the second interferometer, each targeting a different part of the object, to reduce effects of object bulk axial movement while conserving a measurement of relative axial movements between the two different object parts.

18. The method according to claim 13, where for each spectral scan, a single mask is chosen by the sensing method to be used by the Master Slave-OCT protocol to generate a flattened en-face OCT image of a layer targeted by the sensing method.

19. The method according to claim 18, further comprising:
producing at least two en-face OCT images of the layer targeted by the sensing method at different times;
performing a variational method on the two en-face OCT images to obtain an OCTA image that substantiates temporal variations in the layer targeted by the sensing method;
repeating the producing and the performing for different targeted layers in the object, followed by superposition of all OCTA images for each targeted layer to obtain a global OCTA volume of flattened and axially corrected OCTA images.

20. The method according to claim 13, further comprising:
using a set of Q masks as chosen by the sensing method to be used by the MS-OCT protocol to generate for each spectral scan a corrected A-scan, where Q is an integer; and
obtaining, by assembling the A-scans together, a B-scan OCT image flattened along a contour of a layer in the object targeted by the sensing method.

* * * * *